United States Patent
Wang et al.

(10) Patent No.: US 11,186,587 B2
(45) Date of Patent: Nov. 30, 2021

(54) COMPOUND AS ACC INHIBITOR AND USE THEREOF

(71) Applicant: NANJING SANHOME PHARMACEUTICAL CO., LTD., Jiangsu (CN)

(72) Inventors: Yong Wang, Jiangsu (CN); Liwen Zhao, Jiangsu (CN); Yazhou Wang, Jiangsu (CN); Xu Quan, Jiangsu (CN); Chunhuan Jiang, Jiangsu (CN); Hongyan Chen, Jiangsu (CN); Menghua Chen, Jiangsu (CN); Chao Li, Jiangsu (CN); Yexin Liao, Jiangsu (CN); Qi Liu, Jiangsu (CN); Chen Wang, Jiangsu (CN); Hai Wang, Jiangsu (CN); Shengwei Yang, Jiangsu (CN); Guochuang Zheng, Jiangsu (CN)

(73) Assignee: NANJING SANHOME PHARMACEUTICAL CO., LTD., Jiangsu (CN)

( * ) Notice: Subject to any disclaimer, the term of this patent is extended or adjusted under 35 U.S.C. 154(b) by 3 days.

(21) Appl. No.: 16/632,633

(22) PCT Filed: Jul. 25, 2018

(86) PCT No.: PCT/CN2018/096930
§ 371 (c)(1),
(2) Date: Jan. 21, 2020

(87) PCT Pub. No.: WO2019/020041
PCT Pub. Date: Jan. 31, 2019

(65) Prior Publication Data
US 2020/0165265 A1 May 28, 2020

(30) Foreign Application Priority Data
Jul. 26, 2017 (CN) .......................... 201710616033.2

(51) Int. Cl.
| | |
|---|---|
| *C07D 495/04* | (2006.01) |
| *C07D 519/00* | (2006.01) |
| *A61P 1/16* | (2006.01) |
| *A61P 1/00* | (2006.01) |
| *A61P 3/00* | (2006.01) |
| *A61P 35/00* | (2006.01) |
| *A61P 3/04* | (2006.01) |
| *A61P 3/10* | (2006.01) |
| *A61K 31/519* | (2006.01) |
| *A61K 31/5377* | (2006.01) |

(52) U.S. Cl.
CPC .............. *C07D 495/04* (2013.01); *A61P 1/16* (2018.01); *C07D 519/00* (2013.01)

(58) Field of Classification Search
CPC ....... C07D 495/04; C07D 519/00; A61P 1/16; A61P 1/00; A61P 3/00; A61P 35/00; A61P 3/04; A61P 3/10; A61K 31/519; A61K 31/5377
See application file for complete search history.

(56) References Cited

U.S. PATENT DOCUMENTS

2013/0123231 A1  5/2013  Harriman et al.

FOREIGN PATENT DOCUMENTS

| CN | 104105485 | | 10/2014 | | |
|---|---|---|---|---|---|
| CN | 108341830 | | 7/2018 | | |
| WO | WO 2017/075056 | | 5/2017 | | |
| WO | WO 2018/133858 | | 7/2018 | | |
| WO | WO-2018228369 | A1 * | 12/2018 | ........... | C07D 495/04 |
| WO | WO-2019015583 | A1 * | 1/2019 | ........... | C07D 413/14 |

OTHER PUBLICATIONS

English translation of PCT International Search Rerport issued in International Application No. PCT/CN2018/096930, dated Oct. 12, 2018.

\* cited by examiner

*Primary Examiner* — John M Mauro
(74) *Attorney, Agent, or Firm* — Parker Highlander PLLC

(57) ABSTRACT

Disclosed are a class of compounds which are inhibitors of acetyl-CoA carboxylase (ACC) and the use thereof. In particular, provided are compounds as shown in formula I or isomers, pharmaceutically acceptable salts, solvates, crystals or prodrugs thereof, and methods for preparing the same, and pharmaceutical compositions comprising the compounds and the use of the compounds or compositions for treating and/or preventing diseases associated with ACC expression, such as fibrotic diseases, metabolic diseases, cancers or tissue hyperplasia diseases. The compound has a good inhibitory activity against ACC and shows good promise to be a therapeutic drug for fibrotic diseases, metabolic diseases, cancers or tissue hyperplasia diseases.

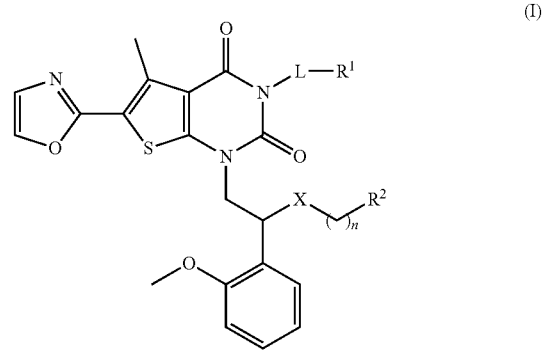

8 Claims, No Drawings

COMPOUND AS ACC INHIBITOR AND USE THEREOF

This application is a national phase application under 35 U.S.C. § 371 of International Application No. PCT/CN2018/096930, filed Jul. 25, 2018, which claims the benefit of Chinse Patent Application No. 201710616033.2, filed Jul. 26, 2017, the entirety of each of which is incorporated herein by reference.

FIELD

The present disclosure relates to the field of medicinal chemistry, and particularly relates to a class of compounds which are inhibitors of acetyl-CoA carboxylase (ACC) or pharmaceutically acceptable salts, isomers, solvates, crystals or prodrugs thereof, and methods for preparing the same, and pharmaceutical compositions comprising the compounds and the use of the compounds or compositions for treating and/or preventing diseases associated with ACC expression, such as fibrotic diseases, metabolic diseases, cancers or tissue hyperplasia diseases.

BACKGROUND

Acetyl-CoA carboxylase (ACC) is a biotinase that catalyzes the reaction of acetyl-CoA to form malonyl-CoA, which is the rate-limiting step that restricts the first stage of fatty acid synthesis. In mammals, ACC exists in the form of two tissue-specific isozymes, of which ACC1 is mainly found in lipid-producing tissues such as liver and fat, while ACC2 is mainly found in oxidized tissues such as liver, heart and skeletal muscle. ACC1 and ACC2 are encoded by independent genes, and although presenting different cell distributions, they share a total of 75% overall amino acid sequence identity. In the liver, the synthesis and elongation of fatty acids (FA) is through malonyl-CoA produced by ACC1-catalyzed acetyl-CoA, thereby promoting triglyceride formation and very low-density lipoprotein (VLDL) production. In the heart and skeletal muscles with limited ability to synthesize fatty acids, malonyl-CoA formed by ACC2 has functions on regulating FA oxidation [Tong L, Harwood H J Jr. *J Cell Biochem.* 2006, 99(6):1476-1788.].

Nonalcoholic fatty liver disease (NAFLD) and nonalcoholic steatohepatitis (NASH) are considered to be two manifestations of abnormal liver metabolism, and are the most common chronic liver disease, and their incidence is increasing year by year. Among them, NASH may further develop into cirrhosis and liver cancer, which may cause death. At present, there is no effective treatment strategy for this type of disease. The existing therapeutic drugs are still insulin sensitizers represented by thiazolidinediones and antioxidants (such as vitamin E), in addition to lipid-lowering drugs and angiotensin receptor antagonist, polyunsaturated fatty acids, etc., and the treatment effect is very limited. In a number of current studies, ACC1 and ACC2 are considered to be potential drug targets for the treatment of NAFLD and NASH [Geraldine Harriman, Jeremy Greenwood, Sathesh Bhat, et al. *Proc Natl Acad Sci U.S.A.* 2016, 113(13): E1796-E1805.].

There has been some progress and research for the study of drug targeting ACC pathways. By inhibiting ACC1 and ACC2, de novo synthesis of liver cell fat can be inhibited. This treatment can significantly reduce liver fat content and sclerosis, and also reduce the level of liver fibrosis markers at an early time. Other studies have shown that simultaneous inhibition of ACC1 and ACC2 reduces the ability to regenerate FA in tumor tissues and has an effect of inhibiting tumor cell growth [Svensson R U, Parker S J, Eichner L J, et al. *Nat Med.* 2016, 22(10): 1108-1119]. However, there is still a need to develop more excellent ACC inhibitors to obtain more active and safer drugs for the treatment of ACC-mediated diseases such as fibrotic diseases, metabolic diseases, tumors and hyperplasia.

SUMMARY

An object of the present disclosure is to provide a compound having an inhibitory activity against ACC, or a pharmaceutically acceptable salt, isomer, solvate, crystal or prodrug thereof,

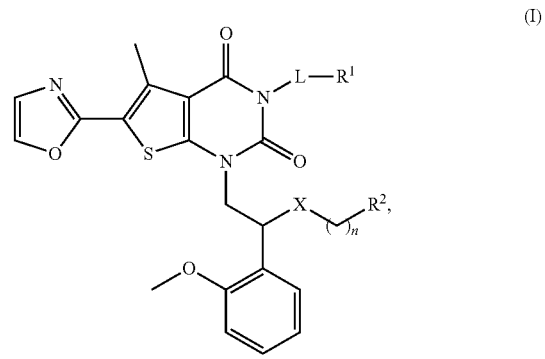

(I)

wherein

L is selected from the group consisting of alkylene, 3-8 membered cycloalkylene, 6-10 membered arylene, 3-8 membered saturated or partially unsaturated heterocycloalkylene containing 1-3 heteroatoms, and 7-13 membered bicyclic heteroarylene containing 1-3 heteroatoms, and each of which is optionally substituted by one or more of hydroxyl, halogen, alkyl, haloalkyl, aminoalkyl, alkylamino, alkoxy, oxo group, alkyl acyl, alkenyl, alkynyl, aryl and heteroaryl;

$R^1$ is selected from hydrogen, halogen, carboxyl, haloalkoxy, $C(O)R^3$ and $S(O)_2R^4$, wherein $R^3$ is selected from the group consisting of alkyl, alkylamino, 3-8 membered cycloalkyl, 6-14 membered aryl, 5-10 membered heteroaryl containing 1-3 heteroatoms and 4-10 membered heterocycloalkyl containing 1-3 heteroatoms, and each of which is optionally substituted by one or more of hydroxyl, alkyl, carboxyl, halogen, haloalkyl, aminoalkyl, alkylamino, alkoxy, oxo group, alkyl acyl, alkenyl, alkynyl, aryl and heteroaryl; and $R^4$ is selected from the group consisting of alkyl, alkylamino, 3-8 membered cycloalkyl, 6-14 membered aryl, 5-10 membered heteroaryl containing 1-3 heteroatoms and 4-10 membered heterocycloalkyl containing 1-3 heteroatoms, and each of which is optionally substituted by one or more of alkyl, halogen, haloalkyl, aminoalkyl, alkylamino, alkoxy, oxo group, alkyl acyl, alkenyl, alkynyl, aryl and heteroaryl;

X is absent or X is oxygen;

$R^2$ is selected from the group consisting of 3-8 membered cycloalkyl, 4-10 membered heterocycloalkyl containing 1-3 heteroatoms and 7-13 membered saturated or partially unsaturated bicyclic heterocyclyl containing 1-3 heteroatoms, and each of which is optionally substituted by one or more of hydroxyl, alkyl, haloalkyl, alkyl acyl, cycloalkyl acyl, alkanoylamino, alkyl sulfonyl, oxo group and 5-8 membered heteroaryl containing 1-3 heteroatoms, and when L is

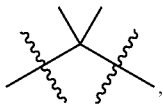 [SMILES: *C(*)(C)C]

$R^2$ is not oxetanyl or tetrahydropyranyl; and n is selected from 0, 1, 2 and 3, and when n is 0, $R^2$ is not hydroxycyclohexyl.

Another object of the present disclosure is to provide a process for producing the compound of formula I of the present disclosure, or a pharmaceutically acceptable salt, isomer, solvate or prodrug thereof.

Another object of the present disclosure is to provide a composition comprising a compound of formula I of the present disclosure, or a pharmaceutically acceptable salt, isomer, solvate or prodrug thereof, and a pharmaceutically acceptable carrier, and a composition comprising a compound of formula I of the present disclosure, or a pharmaceutically acceptable salt, isomer, solvate or prodrug thereof, and another or more ACC inhibitors.

Another object of the present disclosure is to provide use of the compound of formula I of the present disclosure, or a pharmaceutically acceptable salt, isomer, solvate, crystal, prodrug thereof, or the pharmaceutical composition, in the manufacture of a medicament for treating a disease associated with ACC expression in a patient, such as fibrotic disease, metabolic disease, tumor, and proliferative disease.

In view of the above purposes, the present disclosure provides the following technical solutions.

In a first aspect, the present disclosure provides a compound of formula (I),

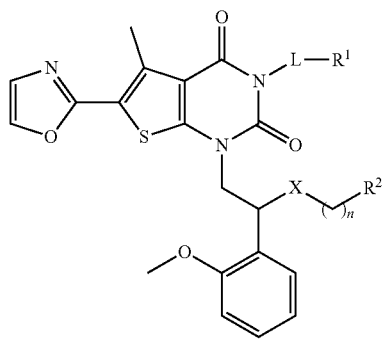

(I)

or a pharmaceutically acceptable salt, isomer, solvate, crystal or prodrug thereof, wherein L is selected from the group consisting of alkylene, 3-8 membered cycloalkylene, 6-10 membered arylene, 3-8 membered saturated or partially unsaturated heterocycloalkylene containing 1-3 heteroatoms, and 7-13 membered bicyclic heteroarylene containing 1-3 heteroatoms, and each of which is optionally substituted by one or more of hydroxyl, halogen, alkyl, haloalkyl, aminoalkyl, alkylamino, alkoxy, oxo group, alkyl acyl, alkenyl, alkynyl, aryl and heteroaryl;

$R^1$ is selected from hydrogen, halogen, carboxyl, haloalkoxy, $C(O)R^3$ and $S(O)_2R^4$, wherein $R^3$ is selected from the group consisting of alkyl, alkylamino, 3-8 membered cycloalkyl, 6-14 membered aryl, 5-10 membered heteroaryl containing 1-3 heteroatoms and 4-10 membered heterocycloalkyl containing 1-3 heteroatoms, and each of which is optionally substituted by one or more of hydroxyl, alkyl, carboxyl, halogen, haloalkyl, aminoalkyl, alkylamino, alkoxy, oxo group, alkyl acyl, alkenyl, alkynyl, aryl and heteroaryl; and $R^4$ is selected from the group consisting of alkyl, alkylamino, 3-8 membered cycloalkyl, 6-14 membered aryl, 5-10 membered heteroaryl containing 1-3 heteroatoms and 4-10 membered heterocycloalkyl containing 1-3 heteroatoms, and each of which is optionally substituted by one or more of alkyl, halogen, haloalkyl, aminoalkyl, alkylamino, alkoxy, oxo group, alkyl acyl, alkenyl, alkynyl, aryl and heteroaryl;

X is absent or X is oxygen;

$R^2$ is selected from the group consisting of 3-8 membered cycloalkyl, 4-10 membered heterocycloalkyl containing 1-3 heteroatoms and 7-13 membered saturated or partially unsaturated bicyclic heterocyclyl containing 1-3 heteroatoms, and each of which is optionally substituted by one or more of hydroxyl, alkyl, haloalkyl, alkyl acyl, cycloalkyl acyl, alkanoylamino, alkyl sulfonyl, oxo group and 5-8 membered heteroaryl containing 1-3 heteroatoms, and when L is

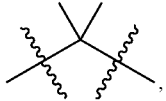 [SMILES: *C(*)(C)C]

$R^2$ is not oxetanyl or tetrahydropyranyl; and n is selected from 0, 1, 2 and 3, and when n is 0, $R^2$ is not hydroxycyclohexyl.

In some preferred embodiments, the compound of the invention is a compound of formula I or a pharmaceutically acceptable salt, isomer, solvate, crystal or prodrug thereof, wherein:

L is selected from the group consisting of $C_{1-8}$ alkylene group, 3-8 membered cycloalkylene, 6-14 membered arylene group, 3-8 membered saturated or partially unsaturated heterocycloalkylene containing 1-4 heteroatoms and 8-12 membered bicyclic heteroarylene group containing 1-4 heteroatoms, and each of which is optionally substituted by one or more of hydroxyl, halogen, $C_{1-6}$ alkyl, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, 6-10 membered aryl and 5-12 membered heteroaryl;

more preferably, L is selected from the group consisting of $C_{1-6}$ alkylene group, 3-6 membered cycloalkylene group, 6-10 membered arylene, 3-6 membered saturated or partially unsaturated heterocycloalkylene group containing 1-3 heteroatoms, and 8-10 membered bicyclic heteroarylene group containing 1-3 heteroatoms, and each of which is optionally substituted by one or more of hydroxyl, halogen, $C_{1-4}$ alkyl, halogenated $C_{1-4}$ alkyl, amino $C_{1-4}$ alkyl, $C_{1-4}$ alkylamino, $C_{1-4}$ alkoxy, oxo group, $C_{1-4}$ alkyl acyl, $C_{2-4}$ alkenyl, $C_{2-4}$ alkynyl, phenyl, naphthyl and 5-8 membered heteroaryl;

even more preferably, L is selected from the group consisting of methylene,

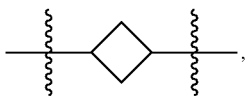

phenylene, azetidinylidene and

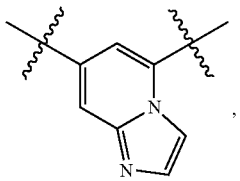 [SMILES: *c1cc(*)n2ccnc2c1]

, and each of which is optionally substituted by one or more of hydroxyl, fluorine, chlorine, bromine, methyl, ethyl, propyl, isopropyl, trifluoromethyl, trifluoroethyl, aminomethyl, aminoethyl, aminopropyl, methylamino, ethylamino, propylamino, isopropylamino, methoxy, ethoxy, propoxy, isopropoxy, oxo group, formyl, acetyl, propionyl, isopropionyl, ethenyl, propenyl, ethynyl, propinyl, phenyl, naphthyl, pyrrolyl, imidazolyl, pyrazolyl, thiazolyl, thienyl, furyl, pyridyl, pyrazinyl and pyrimidinyl.

In some preferred embodiments, the compound of the present disclosure is a compound of formula I or a pharmaceutically acceptable salt, isomer, solvate, crystal or prodrug thereof, wherein $R^1$ is selected from hydrogen, fluorine, carboxyl, halogenated $C_{1-6}$ alkoxy, $C(O)R^3$ and $S(O)_2R^4$; preferably, $R^1$ is selected from hydrogen, fluorine, carboxyl, fluoroethyloxy, chloroethyloxy, bromoethyloxy, fluoropropyloxy, chloropropyloxy, bromopropyloxy, chlorobutyloxy, bromobutyloxy, fluorobutyloxy, $C(O)R^3$ and $S(O)_2R^4$.

In some preferred embodiments, the compound of the present disclosure is a compound of formula I or a pharmaceutically acceptable salt, isomer, solvate, crystal or prodrug thereof, wherein $R^3$ is selected from the group consisting of $C_{1-6}$ alkyl, $C_{1-6}$ alkylamino, 3-6 membered cycloalkyl, 6-10 membered aryl, 5-8 membered heteroaryl containing 1-3 heteroatoms, and 4-8 membered heterocycloalkyl containing 1-3 heteroatoms, and each of which is optionally substituted by one or more of hydroxyl, $C_{1-6}$ alkyl, carboxyl, halogen, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, phenyl, naphthyl and 5-6 membered heteroaryl;

more preferably, $R^3$ is selected from the group consisting of methyl, ethyl, propyl, butyl, isopropyl, isobutyl, tert-butyl, methylamino, ethylamino, propylamino, isopropylamino, cyclopropyl, cyclobutyl, cyclopentyl, cyclohexyl, phenyl, pyrrolyl, imidazolyl, pyrazolyl, thiazolyl, thienyl, furyl, pyridyl, pyrazinyl, pyrimidinyl, azetidinyl, oxetanyl, tetrahydropyrrolyl, tetrahydrofuranyl, piperidinyl, tetrahydropyranyl and morpholinyl, and each of which is optionally substituted by one or more of hydroxyl, methyl, ethyl, propyl, butyl, isopropyl, isobutyl, tert-butyl, carboxyl, fluoro, chloro, bromo, trifluoromethyl, trifluoroethyl, aminomethyl, aminoethyl, aminopropyl, methylamino, ethylamino, propylamino, isopropylamino, methoxy, ethoxy, propoxy, isopropoxy, oxo group, formyl, acetyl, propionyl, isopropionyl, ethenyl, propenyl, ethynyl, propinyl, phenyl, naphthyl, pyrrolyl, imidazolyl, pyrazolyl, thiazolyl, thienyl, furyl, pyridyl, pyrazinyl and pyrimidyl.

In some preferred embodiments, the compound of the present disclosure is a compound of formula I or a pharmaceutically acceptable salt, isomer, solvate, crystal or prodrug thereof, wherein $R^4$ is selected from the group consisting of $C_{1-6}$ alkyl, $C_{1-6}$ alkylamino, 3-6 membered cycloalkyl, 6-10 membered aryl, 5-8 membered heteroaryl containing 1-2 heteroatoms, and 4-8 membered heterocycloalkyl containing 1-2 heteroatoms, and each of which is optionally substituted by one or more of $C_{1-6}$ alkyl, halogen, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, phenyl and 5-6 membered heteroaryl;

more preferably, $R^4$ is methyl, ethyl, propyl, isopropyl, cyclopropyl, cyclobutyl, cyclopentyl, cyclohexyl, phenyl, naphthyl, pyrrolyl, imidazolyl, pyrazolyl, thiazolyl, thienyl, furyl, pyridyl, pyrazinyl, pyrimidinyl, azetidinyl, tetrahydropyrrolyl, tetrahydrofuranyl, piperidinyl, tetrahydropyranyl and morpholinyl, and each of which is optionally substituted by one or more of $C_{1-4}$ alkyl, halogen, halogenated $C_{1-4}$ alkyl, amino $C_{1-4}$ alkyl, $C_{1-4}$ alkylamino, $C_{1-4}$ alkoxy, oxo group, $C_{1-4}$ alkyl acyl, $C_{2-4}$ alkenyl, $C_{2-4}$ alkynyl, phenyl, pyrrolyl, imidazolyl, pyrazolyl, thiazolyl, thienyl, furyl, pyridyl, pyrazinyl and pyrimidinyl.

In some preferred embodiments, the compound of the present disclosure is a compound of formula I or a pharmaceutically acceptable salt, isomer, solvate, crystal or prodrug thereof, wherein $R^2$ is selected from the group consisting of 3-6 membered cycloalkyl group, 4-6 membered heterocycloalkyl group containing 1-2 heteroatoms, and 8-10 membered saturated or partially unsaturated bicyclic heterocyclyl containing 1-2 heteroatoms, and each of which is optionally substituted by one or more of hydroxyl, $C_{1-4}$ alkyl group, halogenated $C_{1-4}$ alkyl group, $C_{1-4}$ alkyl acyl, $C_{1-4}$ alkanoylamino, $C_{1-4}$ alkyl sulfonyl, and 3-6 membered cycloalkyl acyl, oxo group and 5-6 membered heteroaryl containing 1-3 heteroatoms, and when L is

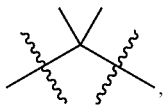 [SMILES: *C(*)(C)C]

, $R^2$ is not oxetanyl and tetrahydropyranyl;

more preferably, $R^2$ is selected from cyclohexyl, azetidinyl, piperidinyl,

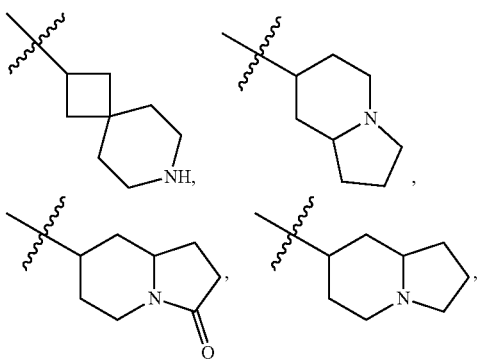

-continued

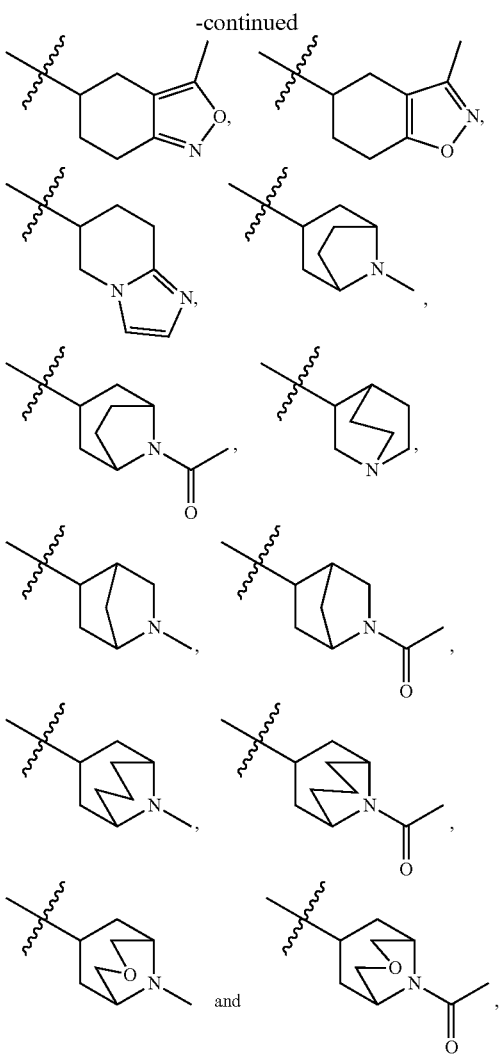

and each of which is optionally substituted by one or more of hydroxy, methyl, trifluoromethyl, trifluoroethyl, acetyl, acetylamino, methylsulfonyl, ethylsulfonyl, cyclohexylformyl, oxo group and imidazolyl.

In some preferred embodiments, the compound of formula (I) of the present disclosure, or a pharmaceutically acceptable salt, isomer, solvate, crystal or prodrug thereof, has a structure as shown in formula (II):

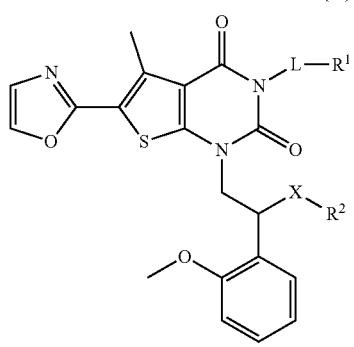

(II)

wherein L, $R^1$, $R^2$ and X are as defined in the above formula (I).

In some embodiments, the compound of formula (I) of the present disclosure or a pharmaceutically acceptable salt, isomer, solvate, crystal or prodrug thereof, has a structure as shown in formula (III):

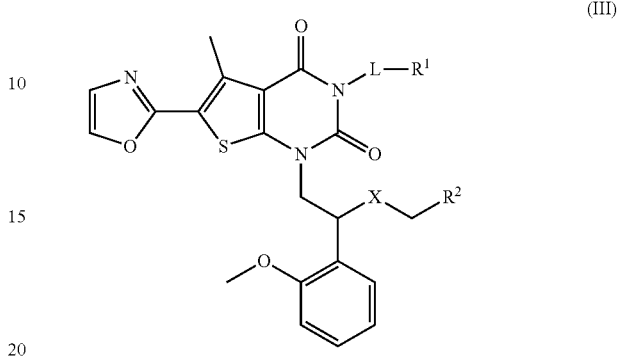

(III)

wherein L, $R^1$, $R^2$ and X are as defined in the above formula (I).

In some embodiments, the compound of formula (I) of the present disclosure or a pharmaceutically acceptable salt, isomer, solvate, crystal or prodrug thereof, has a structure as shown in formula (IV):

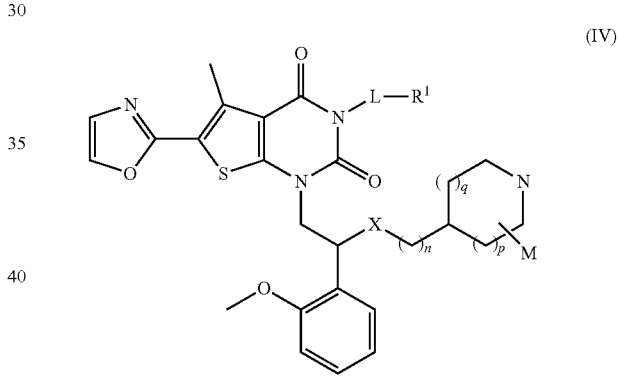

(IV)

wherein,

L is selected from the group consisting of alkylene, 3-8 membered cycloalkylene, 6-10 membered arylene, 3-8 membered saturated or partially unsaturated heterocycloalkylene containing 1-3 heteroatoms, and 7-13 membered bicyclic heteroarylene containing 1-3 heteroatoms, and each of which is optionally substituted by one or more of hydroxyl, halogen, alkyl, haloalkyl, aminoalkyl, alkylamino, alkoxy, oxo group, alkyl acyl, alkenyl, alkynyl, aryl and heteroaryl;

$R^1$ is selected from hydrogen, halogen, carboxyl, haloalkoxy, $C(O)R^3$ and $S(O)_2R^4$, wherein $R^3$ is selected from the group consisting of alkyl, 3-8 membered cycloalkyl, 6-14 membered aryl, 5-10 membered heteroaryl containing 1-3 heteroatoms and 4-10 membered heterocycloalkyl containing 1-3 heteroatoms, and each of which is optionally substituted by one or more of hydroxyl, alkyl, carboxyl, halogen, haloalkyl, aminoalkyl, alkylamino, alkoxy, oxo group, alkyl acyl, alkenyl, alkynyl, aryl and heteroaryl; and R[4] is selected from the group consisting of alkyl, alkylamino, 3-8 membered cycloalkyl, 6-14 membered aryl, 5-10 membered heteroaryl containing 1-3 heteroatoms and 4-10 membered heterocycloalkyl containing 1-3 heteroatoms, and each of which is optionally substituted by one or more of alkyl, halogen, haloalkyl, aminoalkyl, alkylamino, alkoxy, oxo group, alkyl acyl, alkenyl, alkynyl, aryl and heteroaryl;

X is absent or X is oxygen;

n, p, q are respectively selected from 0, 1, 2 and 3;

M is one or more groups selected from hydroxyl, alkyl, aminoalkyl, alkylamino, alkoxy, alkenyl, alkynyl, haloalkyl, alkyl acyl, cycloalkyl acyl, alkanoylamino, alkyl sulfonyl, oxo group and 5-8 membered heteroaryl containing 1-3 heteroatoms, or two M together with the atom(s) to which they are attached form cycloalkyl, heterocycloalkyl, aryl or heteroaryl, and each of which is optionally substituted by one or more of hydroxyl, alkyl, aminoalkyl, alkylamino, alkoxy, alkenyl, alkynyl, haloalkyl, alkyl acyl, cycloalkyl acyl, alkanoylamino, oxo group.

In some embodiments, in the compound of formula (IV) of the present disclosure or a pharmaceutically acceptable salt, isomer, solvate, crystal or prodrug thereof, L is selected from the group consisting of $C_{1-6}$ alkylene, 3-6 membered cycloalkylene, phenylene, 3-6 membered saturated or partially unsaturated heterocycloalkylene containing 1-3 heteroatoms, and 8-10 membered bicyclic heteroarylene containing 1-3 heteroatoms, and each of which is optionally substituted by one or more of hydroxyl, halogen, $C_{1-6}$ alkyl, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, 6-10 membered aryl and 5-12 membered heteroaryl;

more preferably, L is selected from the group consisting of methylene,

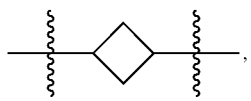

phenylene, azetidinylidene and

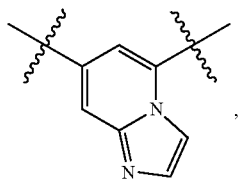 [SMILES: *c1cc(*)n2ccnc2c1]

and each of which is optionally substituted by one or more of hydroxyl, fluorine, chlorine, bromine, methyl, ethyl, propyl, isopropyl, trifluoromethyl, trifluoroethyl, aminomethyl, aminoethyl, aminopropyl, methylamino, ethylamino, propylamino, isopropylamino, methoxy, ethoxy, propoxy, isopropoxy, oxo group, formyl, acetyl, propionyl, isopropionyl, ethenyl, propenyl, ethynyl, propinyl, phenyl, naphthyl, pyrrolyl, imidazolyl, pyrazolyl, thiazolyl, thienyl, furyl, pyridyl, pyrazinyl and pyrimidinyl.

In some embodiments, the compound of formula (IV) of the present disclosure or a pharmaceutically acceptable salt, isomer, solvate, crystal or prodrug thereof, wherein R[1] is selected from hydrogen, fluorine, carboxyl, halogenated $C_{1-6}$ alkoxy, C(O)R[3] and S(O)$_2$R[4], preferably, R[1] is selected from hydrogen, fluorine, carboxyl, fluoroethyloxy, C(O)R[3] and S(O)$_2$R[4], wherein R[3] is selected from the group consisting of $C_{1-6}$ alkyl, $C_{1-6}$ alkylamino, 3-6 membered cycloalkyl, 6-10 membered aryl, 5-8 membered heteroaryl containing 1-3 heteroatoms, and 4-8 membered heterocycloalkyl containing 1-3 heteroatoms, and each of which is optionally substituted by one or more of hydroxyl, $C_{1-6}$ alkyl, carboxyl, halogen, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, phenyl, naphthyl and 5-6 membered heteroaryl; and R[4] is $C_{1-6}$ alkyl, $C_{1-6}$ alkylamino, 3-6 membered cycloalkyl, 6-10 membered aryl, 5-8 membered heteroaryl containing 1-2 heteroatoms, and 4-8 membered heterocycloalkyl containing 1-2 heteroatoms, and each of which is optionally substituted by one or more of $C_{1-6}$ alkyl, halogen, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, phenyl and 5-6 membered heteroaryl.

In some embodiments, the compound of formula (IV) or a pharmaceutically acceptable salt, isomer, solvate, crystal or prodrug thereof, wherein n, p, q are respectively selected from 0, 1 and 2.

In some embodiments, the compound of formula (IV) or a pharmaceutically acceptable salt, isomer, solvate, crystal or prodrug thereof, wherein M is one or more groups selected from hydroxy, $C_{1-4}$ alkyl, amino $C_{1-4}$ alkyl, $C_{1-4}$ alkylamino, $C_{1-4}$ alkoxy, $C_{2-4}$ alkenyl, $C_{2-4}$ alkynyl, halogenated $C_{1-4}$ alkyl, $C_{1-4}$ alkyl acyl, $C_{1-4}$ alkanoylamino, $C_{1-4}$ alkyl sulfonyl, 3-6 membered cycloalkyl acyl, oxo group and 5-6 membered heteroaryl containing 1-3 heteroatoms, or two M together with the atom(s) to which they are attached form 3-8 membered cycloalkyl, 3-8 membered heterocycloalkyl, 3-8 membered aryl or 3-8 membered heteroaryl, and each of which is optionally substituted by one or more of hydroxyl, $C_{1-4}$ alkyl, amino $C_{1-4}$ alkyl, $C_{1-4}$ alkylamino, $C_{1-4}$ alkoxy, $C_{2-4}$ alkenyl, $C_{2-4}$ alkynyl, halogenated $C_{1-4}$ alkyl, $C_{1-4}$ alkyl acyl, $C_{1-4}$ alkanoylamino, oxo group;

more preferably, M is one or more groups selected from hydroxy, methyl, aminomethyl, methylamino, methoxy, ethenyl, ethynyl, trifluoromethyl, trifluoroethyl, acetyl, acetylamino, methylsulfonyl, ethylsulfonyl, cyclohexylformyl, oxo group and imidazolyl, or two M together with the atom(s) to which they are attached form 3-6 membered cycloalkyl, 3-6 membered heterocycloalkyl, 3-6 membered aryl or 3-6 membered heteroaryl, and each of which is optionally substituted by one or more of hydroxy, $C_{1-3}$ alkyl, amino $C_{1-3}$ alkyl, $C_{1-3}$ alkylamino, $C_{1-3}$ alkoxy, $C_{2-3}$ alkenyl, $C_{2-3}$ alkynyl, halogenated $C_{1-3}$ alkyl, $C_{1-3}$ alkyl acyl, $C_{1-3}$ alkanoylamino and oxo group.

In some specific embodiments, in the compound of formula IV) or a pharmaceutically acceptable salt, isomer, solvate, crystal or prodrug thereof, L is

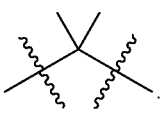

In some specific embodiments, in the compound of formula (IV) or a pharmaceutically acceptable salt, isomer, solvate, crystal or prodrug thereof, R¹ is

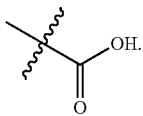 [SMILES: *C(=O)O]

In some specific embodiments, in the compound of formula (IV) or a pharmaceutically acceptable salt, isomer, solvate, crystal or prodrug thereof, n, p, q are 1 respectively.

In some specific embodiments, the compound of formula (IV) or a pharmaceutically acceptable salt, isomer, solvate, crystal or prodrug thereof, wherein the structure

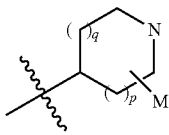

is selected from

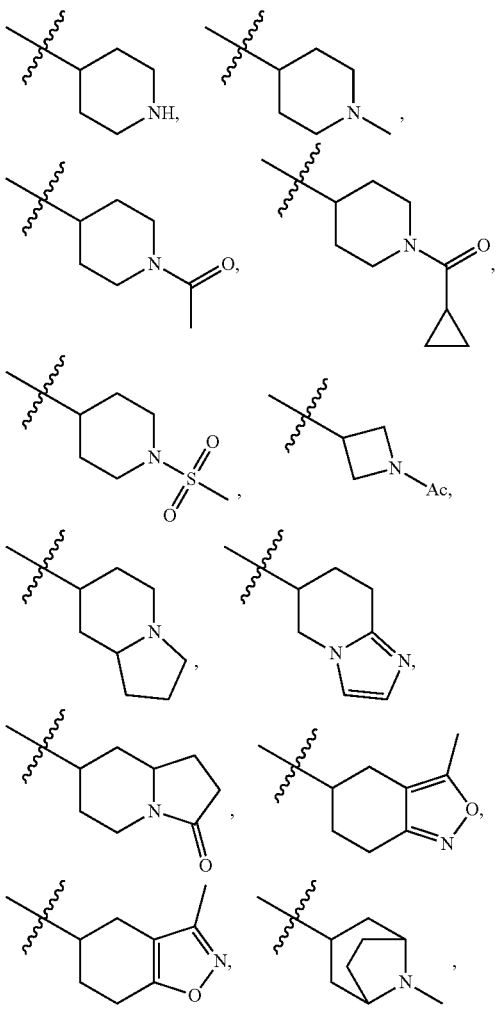

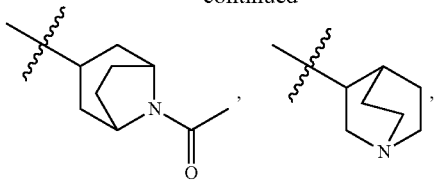

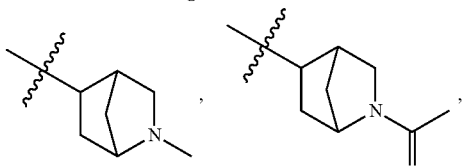

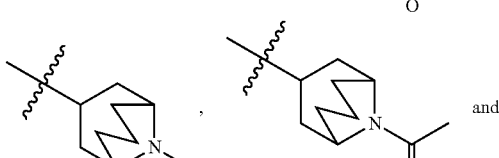

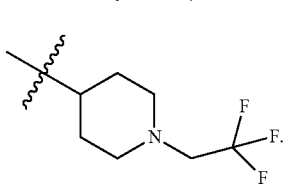

In some specific embodiments, the compound of formula (I) or a pharmaceutically acceptable salt, isomer, solvate, crystal or prodrug thereof, has a structure as shown in formula (V):

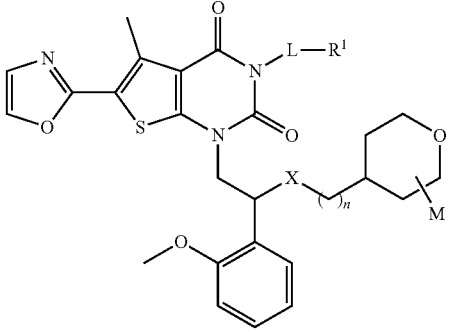

wherein

L is selected from the group consisting of 3-8 membered cycloalkylene, 6-10 membered arylene, 3-8 membered saturated or partially unsaturated heterocycloalkylene containing 1-3 heteroatoms, and 7-13 membered bicyclic heteroarylene containing 1-3 heteroatoms, and each of which is optionally substituted by one or more of hydroxyl, halogen, alkyl, haloalkyl, aminoalkyl, alkylamino, alkoxy, oxo group, alkyl acyl, alkenyl, alkynyl, aryl and heteroaryl;

R¹ is selected from the group consisting of hydrogen, halogen, carboxyl, haloalkoxy, C(O)R³ and S(O)₂R⁴, wherein R³ is selected from the group consisting of alkyl, 3-8 membered cycloalkyl, 6-10 membered aryl, 5-8 membered heteroaryl containing 1-3 heteroatoms and 4-10 membered heterocycloalkyl containing 1-3 heteroatoms, and each of which is optionally substituted by one or more of hydroxyl, alkyl, carboxyl, halogen, haloalkyl, aminoalkyl, alkylamino, alkoxy, oxo group, alkyl acyl, alkenyl, alkynyl, aryl and heteroaryl, $R^4$ is alkyl, alkylamino, 3-8 membered cycloalkyl, 6-14 membered aryl, 5-10 membered heteroaryl containing 1-3 heteroatoms, and 4-10 membered heterocycloalkyl containing 1-3 heteroatoms, and each of which is optionally substituted by one or more of alkyl, halogen, haloalkyl, aminoalkyl, alkylamino, alkoxy, oxo group, alkyl acyl, alkenyl, alkynyl, aryl and heteroaryl;

X is absent or X is oxygen;

n is selected from 0, 1, 2 and 3; and

M is one or more groups selected from hydroxyl, alkyl, aminoalkyl, alkylamino, alkoxy, alkenyl, alkynyl, haloalkyl, alkyl acyl, cycloalkyl acyl, alkanoylamino, alkyl sulfonyl, oxo group and 5-8 membered heteroaryl containing 1-3 heteroatoms, or two M together with the atom(s) to which they are attached form cycloalkyl, heterocycloalkyl, aryl or heteroaryl, and each of which is optionally substituted by one or more of hydroxyl, alkyl, aminoalkyl, alkylamino, alkoxy, alkenyl, alkynyl, haloalkyl, alkyl acyl, cycloalkyl acyl, alkanoylamino and oxo group.

In some embodiments, the compound of formula (V) or a pharmaceutically acceptable salt, isomer, solvate, crystal or prodrug thereof, wherein L is selected from the group consisting of 3-6 membered cycloalkylene, phenylene, 3-6 membered saturated or partially unsaturated heterocycloalkylene containing 1-3 heteroatoms, and 8-10 membered bicyclic heteroarylene containing 1-3 heteroatoms, and each of which is optionally substituted by one or more of hydroxyl, halogen, $C_{1-4}$ alkyl, halogenated $C_{1-4}$ alkyl, amino $C_{1-4}$ alkyl, $C_{1-4}$ alkylamino, $C_{1-4}$ alkoxy, oxo group, $C_{1-4}$ alkyl acyl, $C_{2-4}$ alkenyl, $C_{2-4}$ alkynyl, 6-10 membered aryl and 5-12 membered heteroaryl;

more preferably, L is selected from the group consisting of methylene,

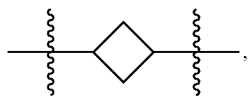 [SMILES: *C1CC(*)C1]

phenylene, azetidinylidene and

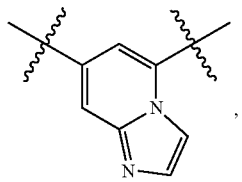 [SMILES: *c1cc(*)n2ccnc2c1]

and each of which is optionally substituted by one or more of hydroxyl, fluorine, chlorine, bromine, methyl, ethyl, propyl, isopropyl, trifluoromethyl, trifluoroethyl, aminomethyl, aminoethyl, aminopropyl, methylamino, ethylamino, propylamino, isopropylamino, methoxy, ethoxy, propoxy, isopropoxy, oxo group, formyl, acetyl, propionyl, isopropionyl, ethenyl, propenyl, ethynyl, propinyl, phenyl, naphthyl, pyrrolyl, imidazolyl, pyrazolyl, thiazolyl, thienyl, furyl, pyridyl, pyrazinyl and pyrimidinyl.

In some embodiments, the compound of formula (V) or a pharmaceutically acceptable salt, isomer, solvate, crystal or prodrug thereof, wherein $R^1$ is selected from hydrogen, fluorine, carboxyl, halogenated $C_{1-6}$ alkoxy, $C(O)R^3$ and $S(O)_2R^4$, preferably, $R^1$ is selected from hydrogen, fluorine, carboxyl, fluoroethyloxy, $C(O)R^3$ and $S(O)_2R^4$, wherein $R^3$ is selected from the group consisting of $C_{1-6}$ alkyl, $C_{1-6}$ alkylamino, 3-6 membered cycloalkyl, 6-10 membered aryl, 5-8 membered heteroaryl containing 1-3 heteroatoms, and 4-8 membered heterocycloalkyl containing 1-3 heteroatoms, and each of which is optionally substituted by one or more of hydroxyl, $C_{1-4}$ alkyl, carboxyl, halogen, halogenated $C_{1-4}$ alkyl, amino $C_{1-4}$ alkyl, $C_{1-4}$ alkylamino, $C_{1-4}$ alkoxy, oxo group, $C_{1-4}$ alkyl acyl, $C_{2-4}$ alkenyl, $C_{2-4}$ alkynyl, phenyl, naphthyl and 5-6 membered heteroaryl;

$R^4$ is selected from the group consisting of $C_{1-6}$ alkyl, $C_{1-6}$ alkylamino, 3-6 membered cycloalkyl, 6-10 membered aryl, 5-8 membered heteroaryl containing 1-2 heteroatoms, and 4-8 membered heterocycloalkyl containing 1-2 heteroatoms, and each of which is optionally substituted by one or more of $C_{1-6}$ alkyl, halogen, halogenated $C_{1-6}$ alkyl, amino $C_{1-6}$ alkyl, $C_{1-6}$ alkylamino, $C_{1-6}$ alkoxy, oxo group, $C_{1-6}$ alkyl acyl, $C_{2-6}$ alkenyl, $C_{2-6}$ alkynyl, phenyl and 5-6 membered heteroaryl.

In some embodiments, the compound of formula (V) or a pharmaceutically acceptable salt, isomer, solvate, crystal or prodrug thereof, wherein n is selected from 0, 1 and 2.

In some embodiments, the compound of formula (V) or a pharmaceutically acceptable salt, isomer, solvate, crystal or prodrug thereof, wherein M is one or more groups selected from hydroxy, $C_{1-4}$ alkyl, amino $C_{1-4}$ alkyl, $C_{1-4}$ alkylamino, $C_{1-4}$ alkoxy, $C_{2-4}$ alkenyl, $C_{2-4}$ alkynyl, halogenated $C_{1-4}$ alkyl, $C_{1-4}$ alkyl acyl, $C_{1-4}$ alkanoylamino, $C_{1-4}$ alkyl sulfonyl, 3-6 membered cycloalkyl acyl, oxo group and 5-6 membered heteroaryl containing 1-3 heteroatoms, or two M together with the atom(s) to which they are attached form 3-8 membered cycloalkyl, 3-8 membered heterocycloalkyl, 3-8 membered aryl or 3-8 membered heteroaryl, and each of which is optionally substituted by one or more of hydroxyl, $C_{1-4}$ alkyl, amino $C_{1-4}$ alkyl, $C_{1-4}$ alkylamino, $C_{1-4}$ alkoxy, $C_{2-4}$ alkenyl, $C_{2-4}$ alkynyl, halogenated $C_{1-4}$ alkyl, $C_{1-4}$ alkyl acyl, $C_{1-4}$ alkanoylamino, oxo group;

more preferably, M is one or more groups selected from hydroxy, methyl, aminomethyl, methylamino, methoxy, ethenyl, ethynyl, trifluoromethyl, trifluoroethyl, acetyl, acetylamino, methylsulfonyl, ethylsulfonyl, cyclohexylformyl, oxo group and imidazolyl, or two M together with the atom(s) to which they are attached form 3-6 membered cycloalkyl, 3-6 membered heterocycloalkyl, 3-6 membered aryl or 3-6 membered heteroaryl, and each of which is optionally substituted by one or more of hydroxy, $C_{1-3}$ alkyl, amino $C_{1-3}$ alkyl, $C_{1-3}$ alkylamino, $C_{1-3}$ alkoxy, $C_{2-3}$ alkenyl, $C_{2-3}$ alkynyl, halogenated $C_{1-3}$ alkyl, $C_{1-3}$ alkyl acyl, $C_{1-3}$ alkanoylamino and oxo group.

In some specific embodiments, in the compound of formula (V) or a pharmaceutically acceptable salt, isomer, solvate, crystal or prodrug thereof, X is —O—.

In some specific embodiments, the compound of formula (V) or a pharmaceutically acceptable salt, isomer, solvate, crystal or prodrug thereof, wherein

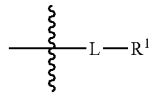

is selected from
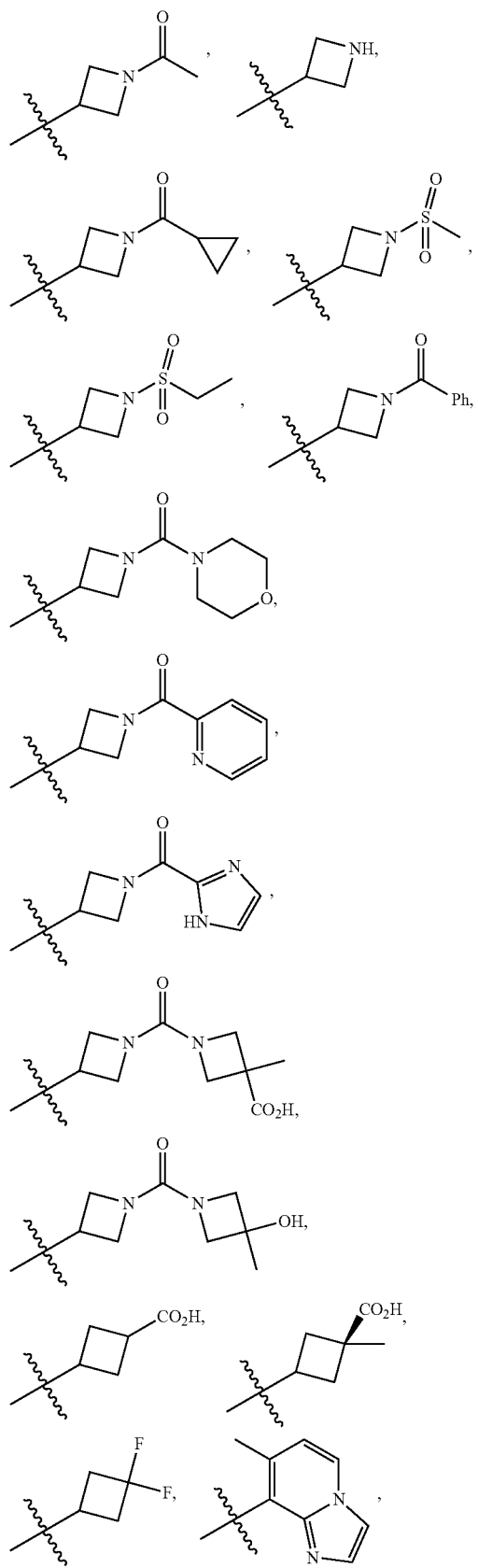
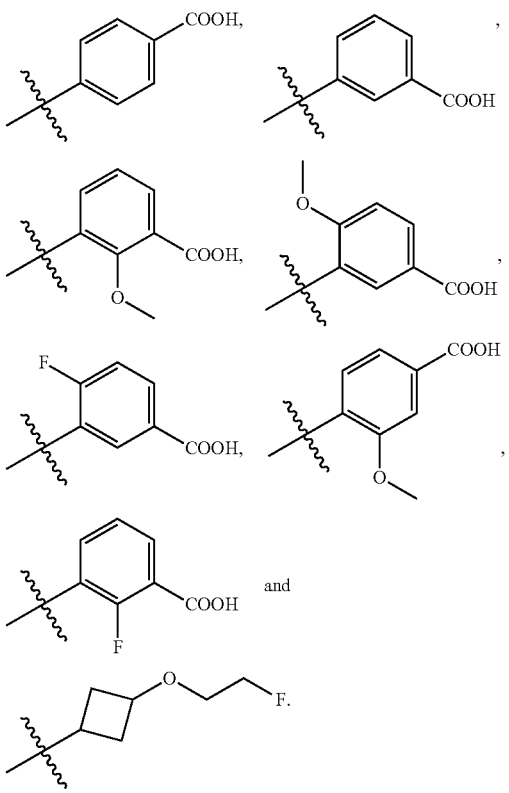
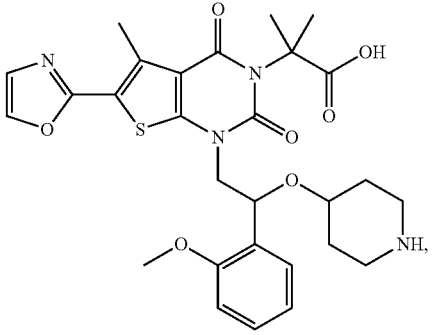
and
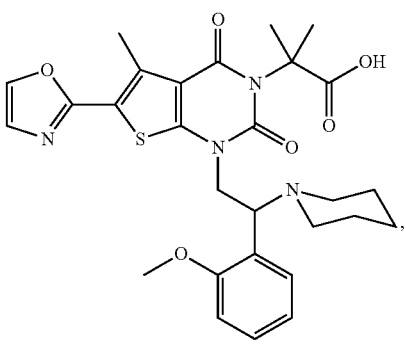
The present disclosure provides the following compounds

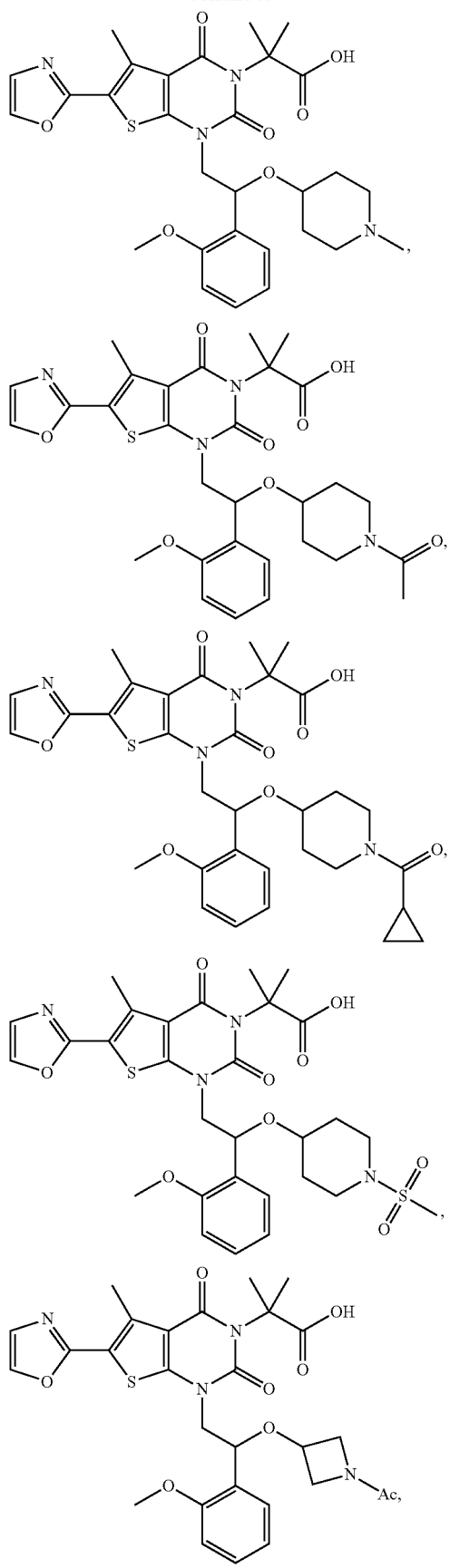
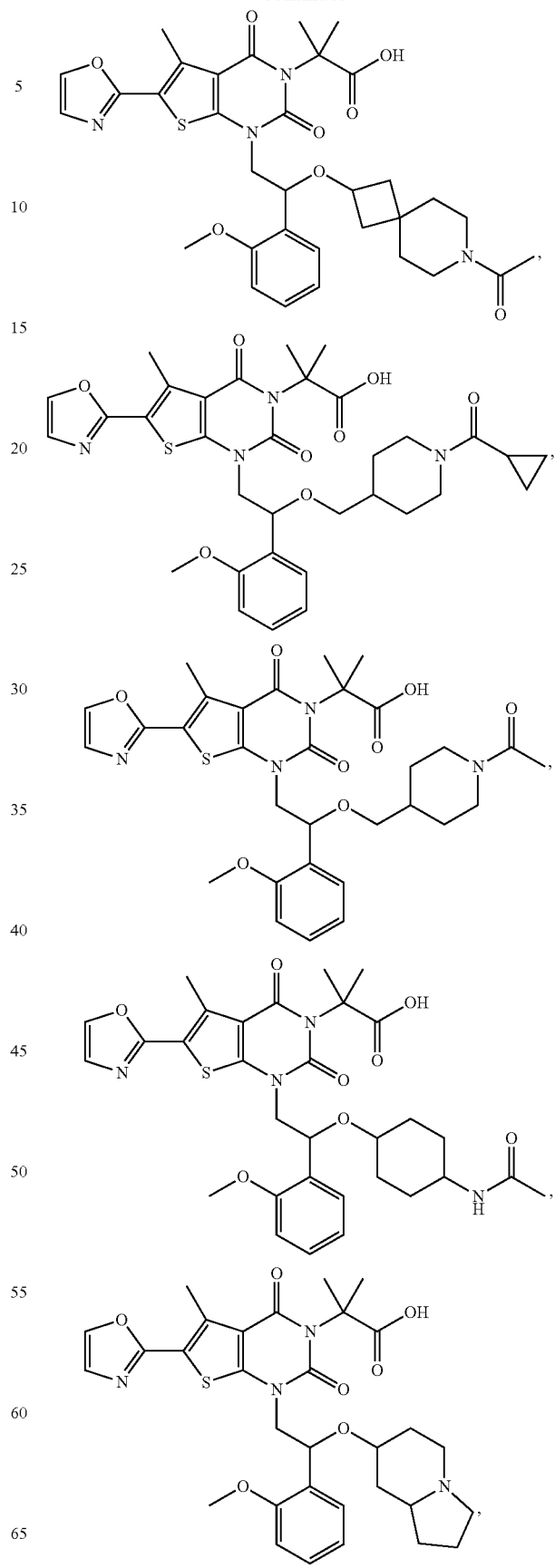

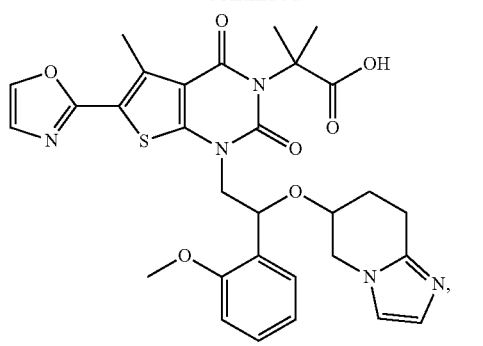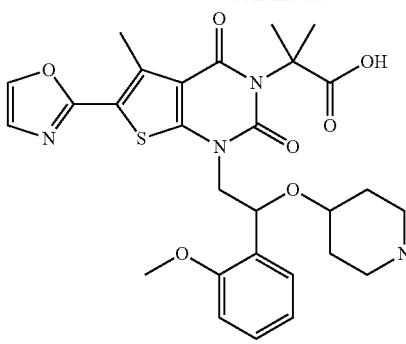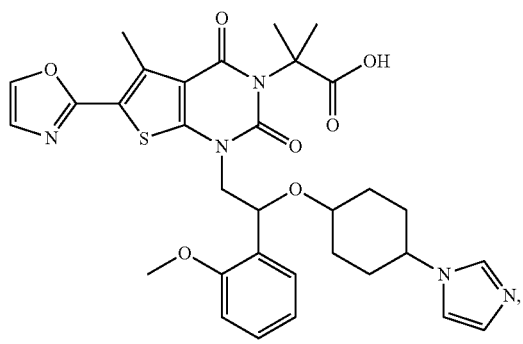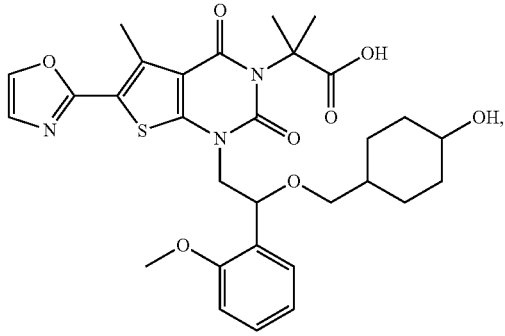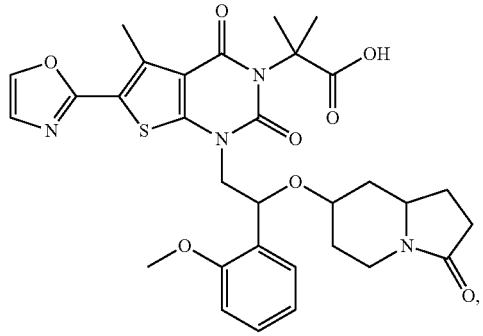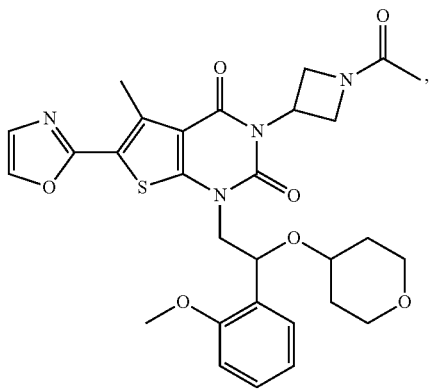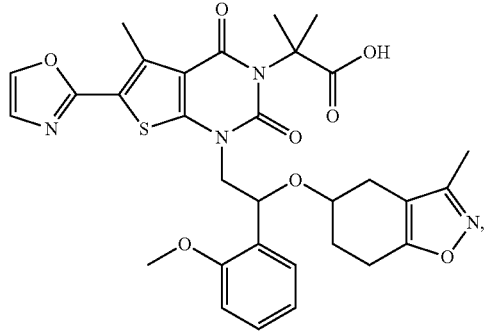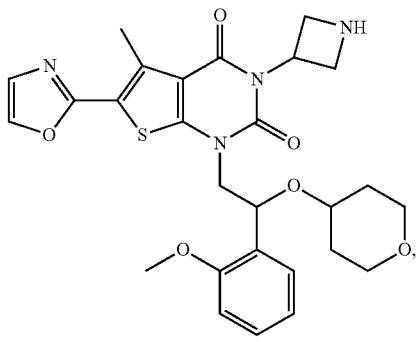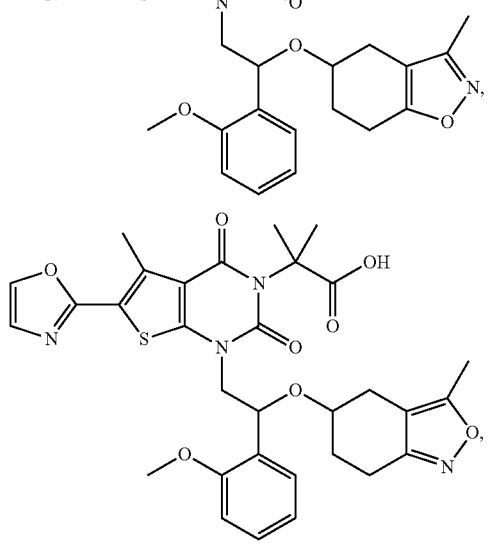

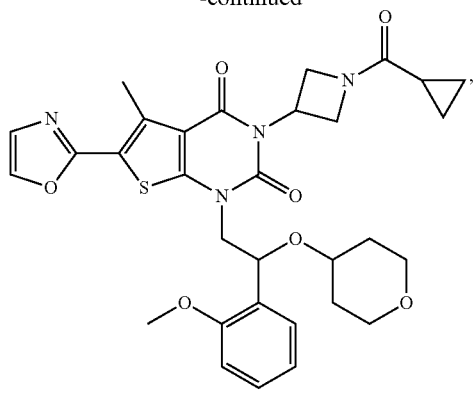
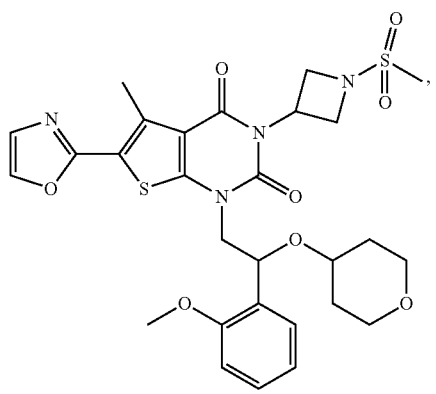
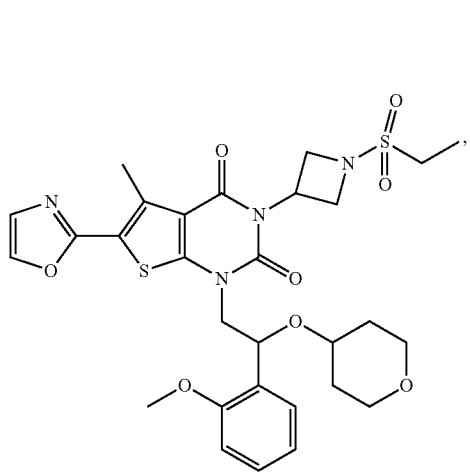
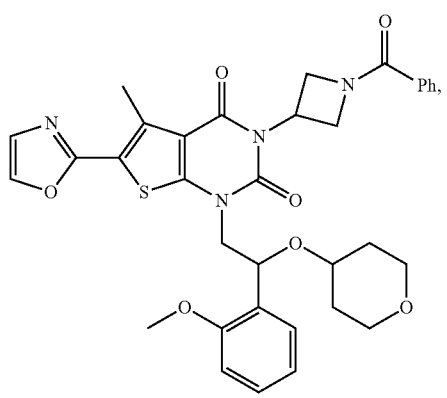
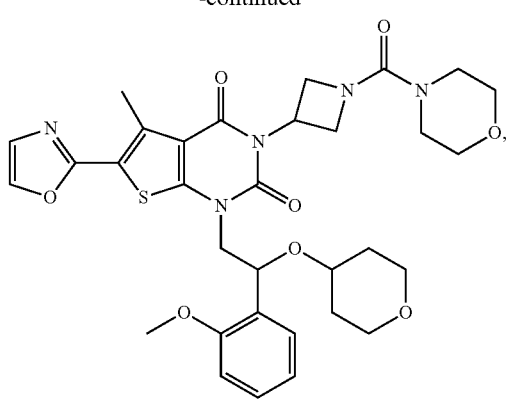
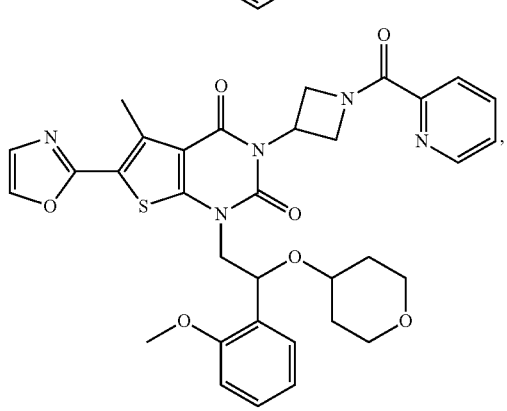
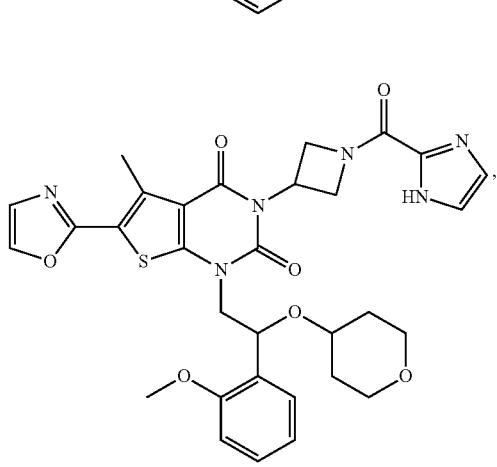
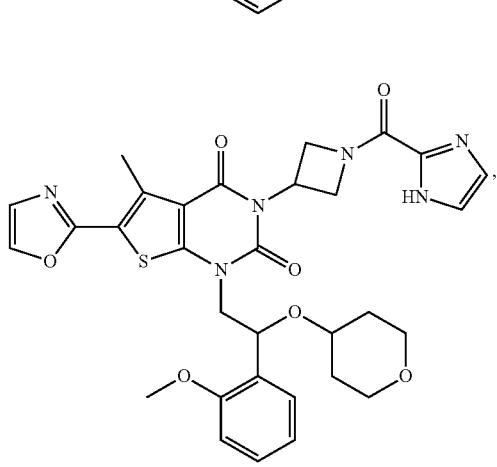

23
-continued
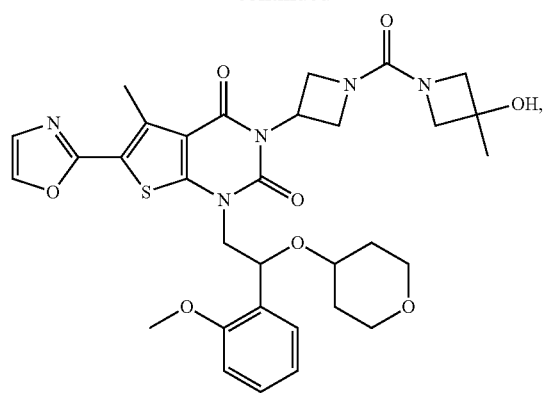
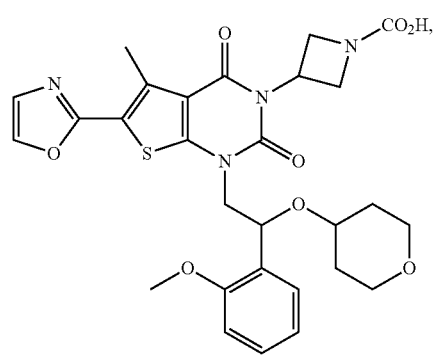
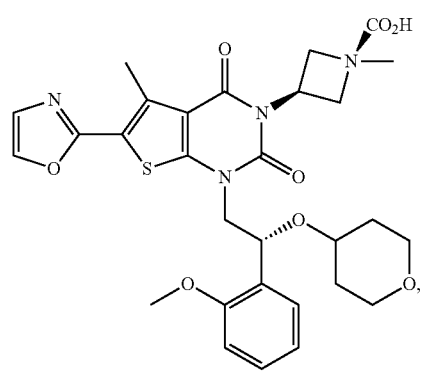
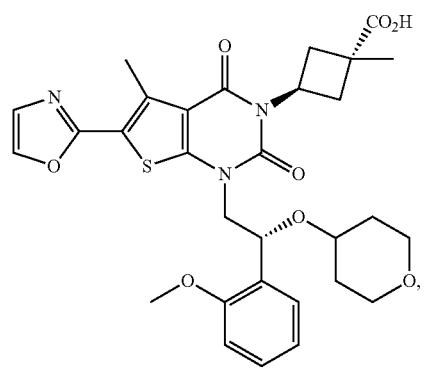
24
-continued
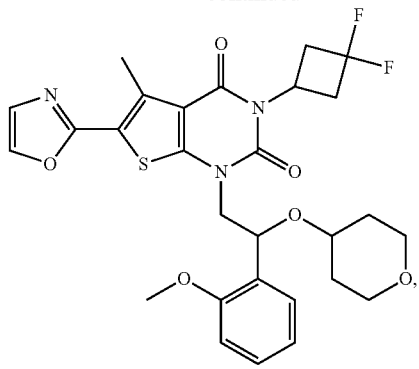
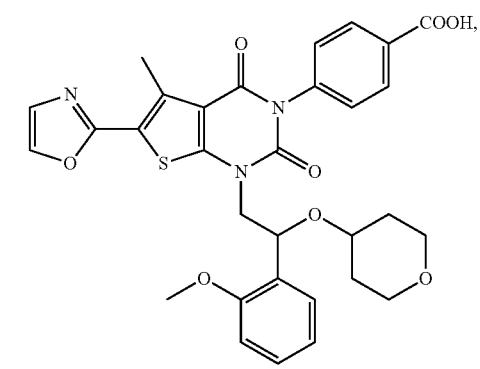
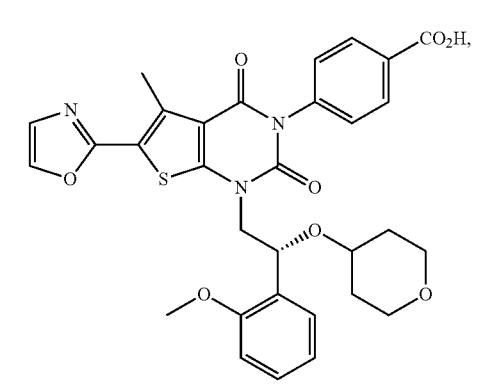

25
-continued
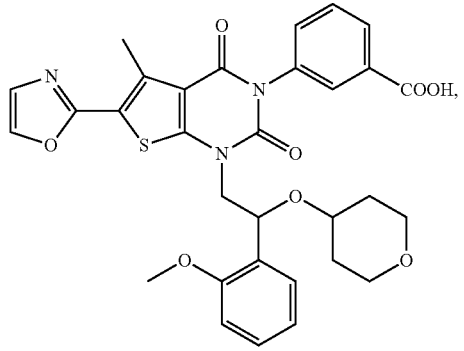
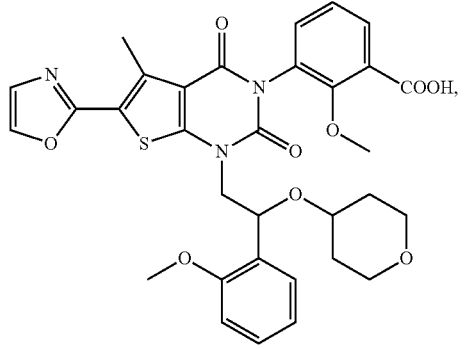
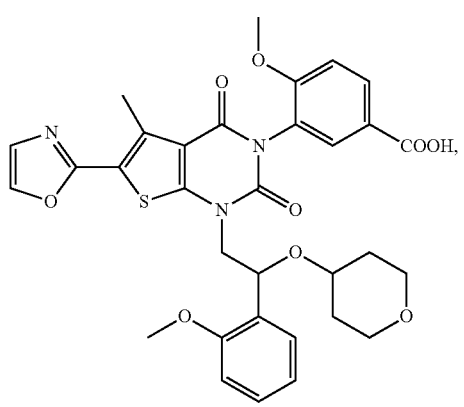
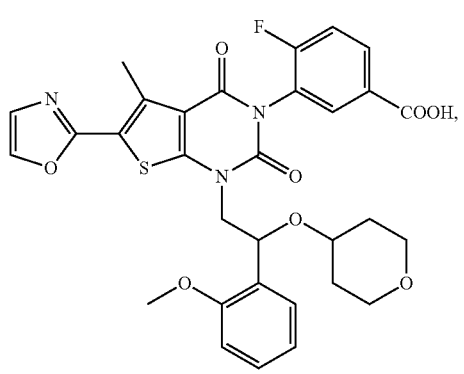
26
-continued
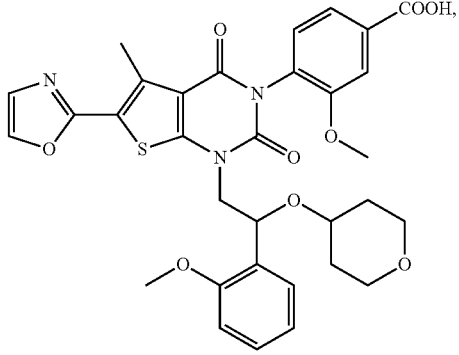
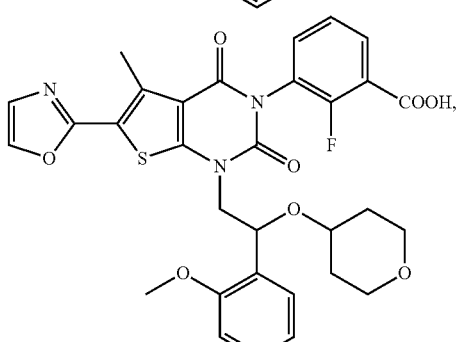
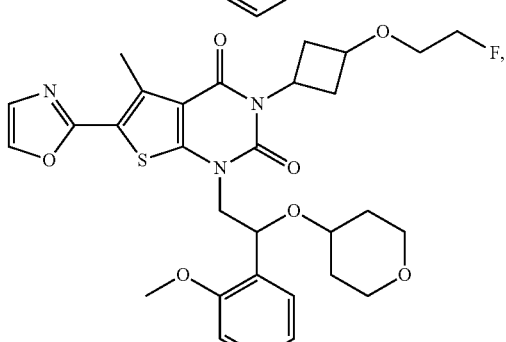
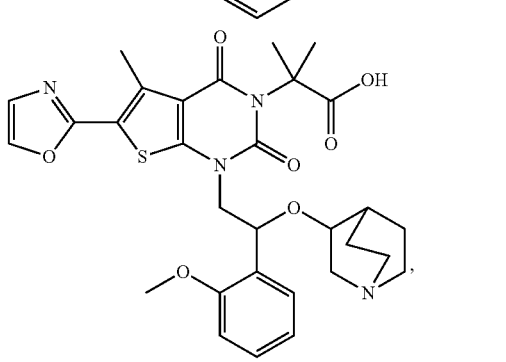

27
-continued
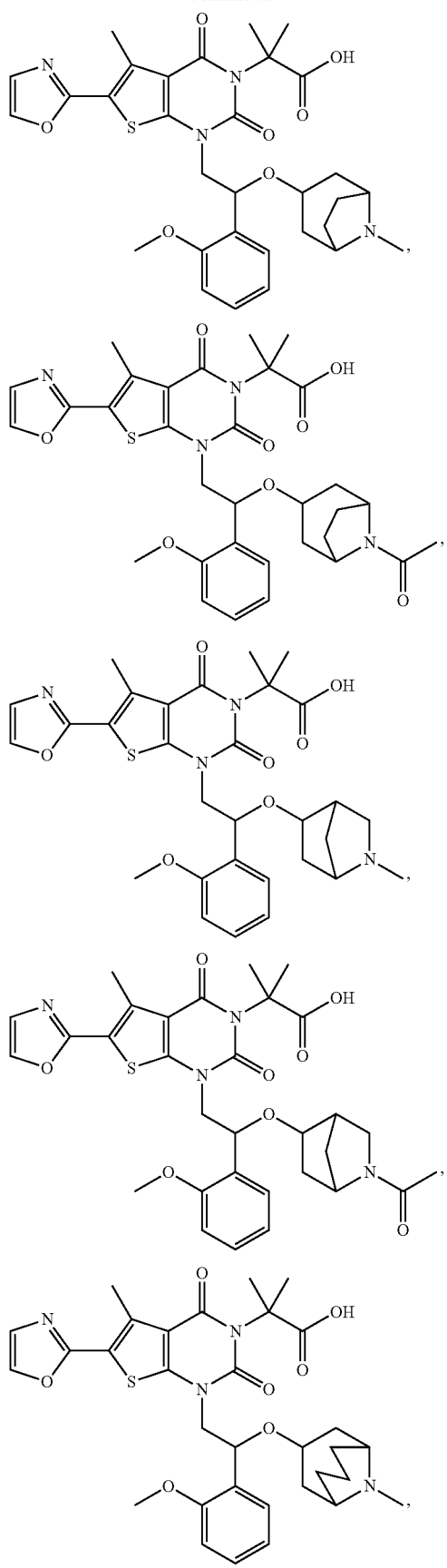
28
-continued
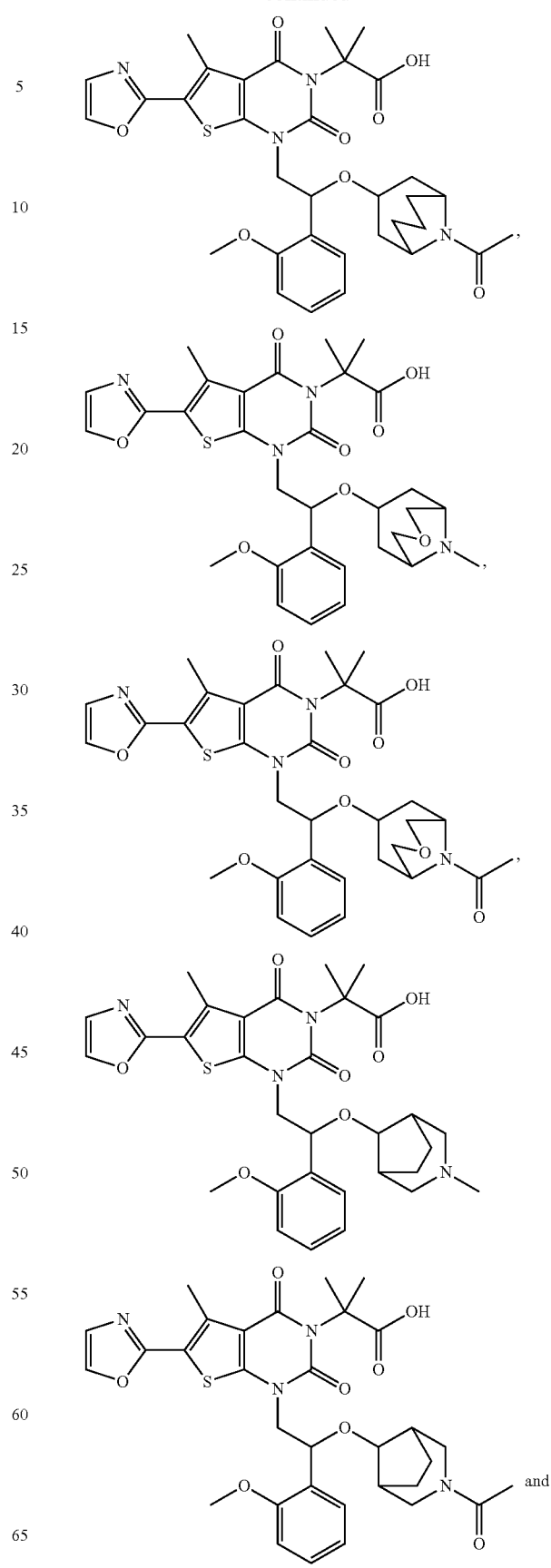

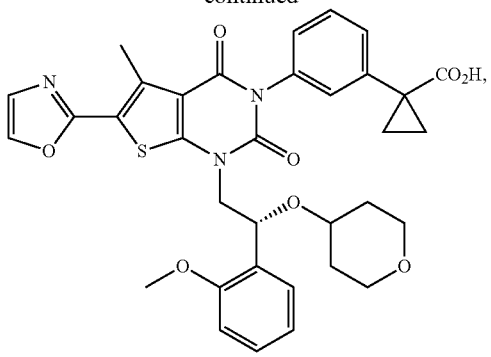

or a pharmaceutically acceptable salt, isomer, solvate, crystal or prodrug thereof.

In another aspect, the present disclosure provides a process for producing the compound represented by the general formula:

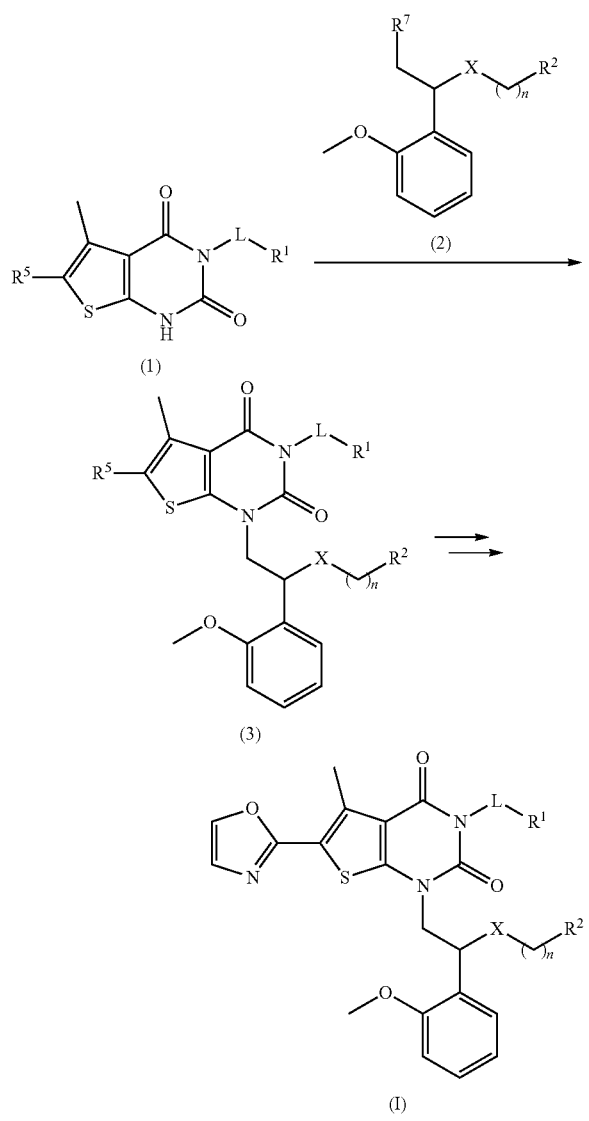

a) a compound of formula (1) reacts with a compound of formula (2) to give an intermediate of formula (3); and b) the intermediate of formula (3) is subjected to a conventional reaction to give a compound of formula (I);

wherein the conventional reaction of step b) includes, but not limited to, the following reaction: subjecting the intermediate of formula (3) to a bromination reaction, a Stille coupling reaction, a hydrolysis reaction or a condensation reaction to obtain a compound of formula (I);

wherein L, X, $R^1$ and $R^2$ are as defined in formula I; $R^5$ is selected from hydrogen and bromine; during the reaction, $R^1$ and $R^2$ have a protecting group if necessary, such as methyl, ethyl, tert-butyl, acetyl, tert-butoxycarbonyl.

In a third aspect, the present disclosure provides a pharmaceutical composition comprising a compound of the present disclosure, or a pharmaceutically acceptable salt, isomer, solvate, crystal or prodrug thereof, and a pharmaceutically acceptable carrier.

In some embodiments, the present disclosure provides a pharmaceutical composition comprising a compound of the present disclosure, or a pharmaceutically acceptable salt, isomer, solvate, crystal or prodrug thereof, and one or more components selected from: other ACC inhibitor, bile acid sequestrant, HMG-CoA reductase inhibitor, HMG-CoA synthetase inhibitor, cholesterol absorption inhibitor, acyl-CoA-cholesteryl acyltransferase (ACAT) inhibitor, CETP inhibitor, squalene synthetase inhibitor, squalene epoxidase inhibitor, PPAR-α agonist, PPAR-γ agonist, PPAR-δ partial agonist, PPAR-α/γ agonist, biguanide, ASK1 inhibitor, FXR receptor modulator, LXR receptor modulator, lipoprotein synthesis inhibitor, renin-angiotensin system inhibitor, triglyceride synthesis inhibitor, low density lipoprotein receptor inducer, microsomes triglyceride delivery inhibitor, 5-LO or FLAP inhibitor, niacin, diuretic, β-adrenergic blocker, calcium channel blocker, angiotensin-converting enzyme (ACE) inhibitor, neutral endopeptidase inhibitor, endothelin antagonist, vasodilator, angiotensin II receptor antagonists, α/β adrenergic blockers, a1 blocker, α2 agonist, aldosterone inhibitor, mineralocorticoid receptor inhibitor, renin inhibitor, angiopoietin 2 binding agent, DGAT-1 inhibitor, AZD7687, LCQ908, DGAT-2 inhibitor, PDE-10 inhibitor, AMPK activator, sulfonylurea, α-amylase inhibitor, α-glucosidase inhibitors, GLP-1 modulator, SIRT-1 inhibitor, insulin secretagogue, A2 antagonist, JNK inhibitor, glucokinase activator, insulin, insulin simulant, glycogen phosphorylase inhibitor, VPAC2 receptor agonist, SGLT2 inhibitor, glycosidic receptor modulator, GPR119 modulator, FGF21 derivative, TGR5 (GPBAR1) receptor agonist, GPR40 agonist, GPR120 agonist, nicotinic acid receptor (HM74A) activator, SGLT1 inhibitor, carnitine palmitoyltransferase inhibitor, fructose 1,6-bisphosphatase inhibitor, aldose reductase inhibitor, mineralocorticoid receptor inhibitor, TORC2 inhibitor, CCR2 inhibitor, CCR5 inhibitor, PKC inhibitor, fatty acid synthase inhibitor, serine palmitoyltransferase inhibitor, GPR81 modulator, GPR39 modulator, GPR43 modulator, GPR41 modulator, GPR105 modulator, Kv1.3 inhibitor, retinol binding protein 4 inhibitor, glucocorticoid receptor modulator, somatostatin receptor inhibitor, PDHK2 inhibitor, PDHK4 inhibitor, MAP4K4 inhibitor, IL1-β modulator, RXR-α modulator, 11-β-hydroxysteroid dehydrogenase 1 inhibitor, SCD-1 inhibitor, MCR-4 agonists, CCK-A agonists, monoamine reuptake inhibitors, β-3-adrenergic receptor agonist, dopamine receptor agonist, melanocyte stimulating hormone and analogs thereof, 5-HT2C agonist, melanin-concentrating hormone antagonist, leptin, leptin analog, leptin agonist, galanin antagonist, lipase inhibitor, anorectic agent, NPY antagonist, PYY3-36 (and analogs thereof), BRS3 modulator, thyroxine agent, dehydroepiandrosterone, glucocorticoid agonist or antagonist, appetite hormone receptor antagonists, human squirrel-associated protein (AGRP) inhibitor, H3 antagonist or inverse agonist, neurotransmitter U agonist, MTP/ApoB inhibitor, CB1 receptor antagonist or inverse agonist, gastric hormone agonist or antagonist, oxyntomodulin and analogs thereof, monoamine absorption inhibitor, and the like.

In some embodiments, the present disclosure provides a compound, or a pharmaceutically acceptable salt, isomer, solvate, crystal or prodrug thereof, and a pharmaceutical composition comprising the compound or pharmaceutically acceptable salt, isomer, solvate, crystal or prodrug thereof, and use of the compound or the pharmaceutical composition for the manufacture of a medicament for treating a disease associated with ACC expression in a patient, such as fibrotic disease, metabolic disease, tumor or proliferative disease.

The compound or pharmaceutically acceptable salt, isomer, solvate, crystal or prodrug thereof may be mixed with a pharmaceutically acceptable carrier, diluent or excipient to produce a pharmaceutical preparation suitable for oral or parenteral administration. Methods of administration include, but not limited to, oral, intradermal, intramuscular, intraperitoneal, intravenous, subcutaneous, and intranasal administration. The formulation may be administered by any route, for example by oral administration, by infusion or bolus injection, by a route of absorption through the epithelium or skin mucosa (e.g., oral mucosa or rectum). Administration can be systemic or topical. Examples of the orally administered preparations include solid or liquid dosage forms, specifically, tablets, pills, granules, powders, capsules, syrups, emulsions, suspensions and the like. The formulations may be prepared by methods known in the art and comprise carriers, diluents or excipients conventionally used in the field of pharmaceutical formulations.

In a fourth aspect, the present disclosure provides use of the compound of formula (I) or pharmaceutically acceptable salt, isomer, solvate, crystal or prodrug thereof, or a composition comprising the same for the manufacture of a medicament for treating a disease associated with ACC expression, such as a fibrotic disease, a metabolic disease, a tumor, and a proliferative disease, wherein the fibrotic disease is liver fibrosis, the metabolic disease is selected from obesity, diabetes, nonalcoholic fatty liver disease, or nonalcoholic steatohepatitis, and the tumor and proliferative disease are selected from liver cancer, kidney cancer, lung cancer, breast cancer, melanoma, papillary thyroid tumor, cholangiocarcinoma, colon cancer, ovarian cancer, malignant lymphoma, cancer and sarcoma of bladder, prostate and pancreas, and primary and recurrent solid tumor of skin, colon, thyroid, and ovary.

In some embodiments, the present disclosure relates to a method of treating fibrotic disease, metabolic disease, tumor or proliferative disease, comprising administering to a subject in need thereof a therapeutically effective amount of the compound of formula (I) or a pharmaceutically acceptable salt, isomer, solvate, or prodrug, or a pharmaceutical composition comprising the same, wherein the fibrotic disease is liver fibrosis, the metabolic disease is selected from obesity, diabetes, nonalcoholic fatty liver disease, or nonalcoholic steatohepatitis, and the tumor and proliferative disease are selected from liver cancer, kidney cancer, lung cancer, breast cancer, melanoma, papillary thyroid tumor, cholangiocarcinoma, colon cancer, ovarian cancer, malignant lymphoma, cancer and sarcoma of bladder, prostate and pancreas, and primary and recurrent solid tumor of skin, colon, thyroid, and ovary.

Terms

The terms used in the specification and claims have the following meanings unless stated to the contrary.

The "halogen" of the present disclosure means fluorine, chlorine, bromine or iodine.

The "alkyl" of the present disclosure means a linear or branched saturated aliphatic hydrocarbon group, preferably a linear or branched group having 1 to 6 carbon atoms, and more preferably a linear or branched group having 1 to 3 carbon atoms, and the non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, and the like. The alkyl group may be substituted or unsubstituted, and if substituted, the substituent can attach to any usable point.

The "carboxyl" of the present disclosure means a group having carboxyl (—COOH) in the molecule. Non-limiting examples of carboxyl include: formyl (—COOH), acetoxy (—CH$_2$COOH), propionyloxy (—CH$_2$CH$_2$COOH),

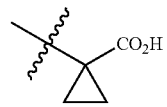 [SMILES: *C1(C(=O)O)CC1]

and the like. The "haloalkyl" of the present disclosure means an alkyl substituted with at least one halogen.

The "hydroxyalkyl" of the present disclosure means an alkyl substituted with at least one hydroxyl.

The "alkoxy" of the present disclosure means —O-alkyl. Non-limiting examples of alkoxy include: methoxy, ethoxy, propoxy, n-propoxy, isopropoxy, isobutoxy, sec-butoxy, and the like. The alkoxy can be optionally substituted or unsubstituted, and if substituted, the substituent can attach to any usable point.

The "alkylene" of the present disclosure means a group formed by removing a hydrogen atom from alkyl, such as a methylene group (—CH$_2$— or =CH$_2$), an ethylene group (—CH$_2$—CH$_2$—), a propylene group (—CH$_2$—CH$_2$—CH$_2$—) and the like, and a "C$_{1-6}$ alkylene group" as used herein means a group formed by removing a hydrogen atom from C$_{1-6}$ alkyl.

The "cycloalkyl" of the present disclosure means a cyclic saturated hydrocarbon group. Suitable cycloalkyl may be substituted or unsubstituted monocyclic, bicyclic or tricyclic saturated hydrocarbon groups having 3-8 carbon atoms, such as cyclopropyl, cyclobutyl, cyclopentyl, cyclohexyl.

The "heterocycloalkyl containing 1-3 heteroatoms" of the present disclosure means a group obtained by substituting a carbon atom at the ring of a cycloalkyl with 1-3 heteroatoms, such as azacyclobutyl

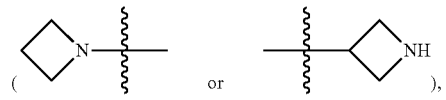 [SMILES: *N1CCC1 ; *C1CNC1]

piperidinyl

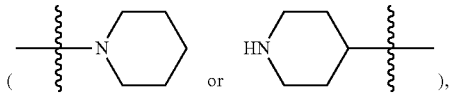

tetrahydropyranyl, morpholinyl, etc. As used herein, "4-10 membered heterocycloalkyl containing 1-3 heteroatoms" means a group obtained by substituting carbon atom at the ring of a 4-10 membered cycloalkyl with 1-3 heteroatoms, and the "4-6 membered heterocycloalkyl containing 1-3 heteroatoms" means a group obtained by substituting carbon atom at the ring of a 4-10 membered cycloalkyl with 1-3 heteroatoms.

The "bicyclic heterocyclyl containing 1-3 heteroatoms" of the present disclosure means a group obtained by substituting carbon atom at the ring of a saturated or partially unsaturated bicycloalkyl group with 1-3 heteroatoms, such as

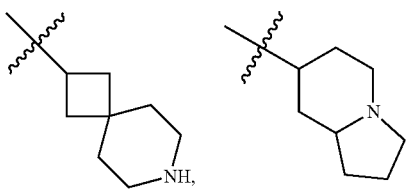

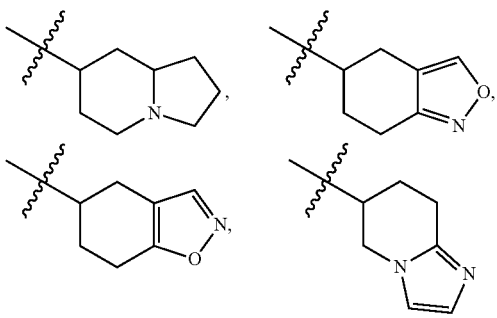

etc. As used herein, "7-12 membered saturated or partially unsaturated bicyclic heterocyclyl containing 1-3 heteroatoms" means a group obtained by substituting carbon atom at the ring of a 7-12 membered saturated or partially unsaturated bicycloalkyl group with 1-3 heteroatoms, and "8-12 membered saturated or partially unsaturated bicyclic heterocyclyl containing 1-2 heteroatoms" means a group obtained by substituting carbon atom at the ring of a 8-12 membered saturated or partially unsaturated bicycloalkyl group with 1-2 heteroatoms.

The "cycloalkylene" of the present disclosure means a group formed by removing a hydrogen atom from cycloalkyl, such as a cyclopropylene group

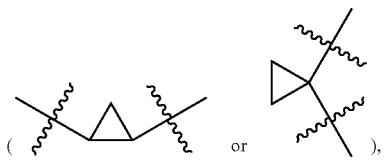 [SMILES: *C1CC1* ; *C1(*)CC1]

a cyclobutylene group

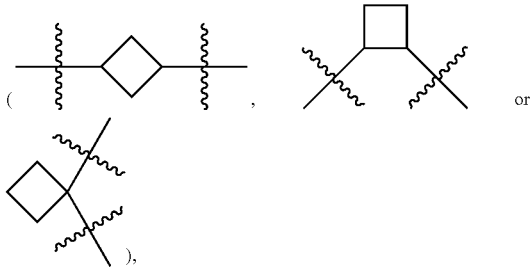

a cyclohexylene group

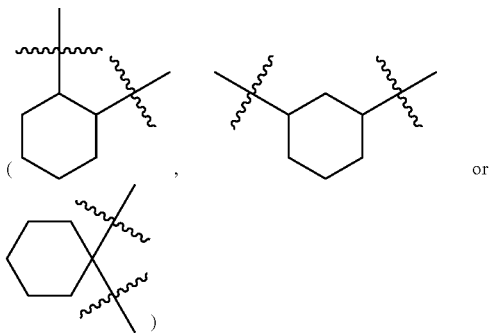

etc. As used herein, "3-8 membered cycloalkylene" means a group formed by removing a hydrogen atom from 3-8 membered cycloalkyl, "3-6 membered cycloalkylene group" means a group formed by removing a hydrogen atom from 3-6 membered cycloalkyl.

The "heterocycloalkylene group containing 1-3 heteroatoms" of the present disclosure means a group obtained by substituting carbon atom at the ring of alkylene with 1-3 heteroatoms, such as an azetidinylidene group

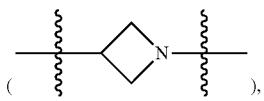

a piperidylidene group

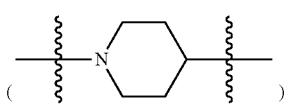

etc. As used herein, "3-8 membered saturated or partially unsaturated heterocycloalkylene group containing 1-3 heteroatoms" means a group formed by removing a hydrogen atom from a 3-8 membered saturated or partially unsaturated cycloalkyl containing 1-3 heteroatoms, "3-6 membered saturated or partially unsaturated heterocycloalkylene group containing 1-3 heteroatoms" means a group formed by removing a hydrogen atom from a 3-6 membered saturated or partially unsaturated cycloalkyl containing 1-3 heteroatoms.

The "aryl" of the present disclosure means a group formed by removing a hydrogen atom from a carbon atom at the aromatic nucleus of an aromatic hydrocarbon molecule, such as phenyl, naphthyl and the like.

The "arylene" of the present disclosure means a group formed by removing a hydrogen atom from aryl, such as a phenylene group

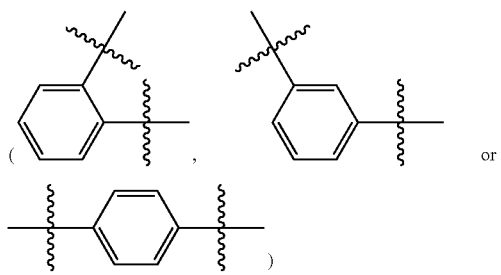

and a naphthylene group and the like.

The "heteroaryl" of the present disclosure means a group obtained by substituting a carbon atom at the ring of aryl with heteroatoms, such as imidazolyl

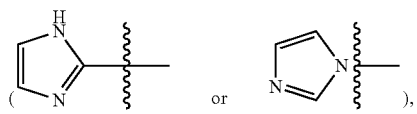

pyrazolyl, pyridyl, indolyl and the like.

The "heteroarylene" of the present disclosure means a group formed by removing a hydrogen atom from the aromatic nucleus of a heteroaryl, such as

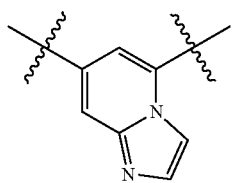 [SMILES: *c1cc(*)n2ccnc2c1]

and the like.

"Hydrogen", "carbon", "oxygen" in the compounds of the present disclosure include all isotopes thereof. Isotopes are understood to include those atoms having the same number of atoms but having different mass numbers. For example, isotopes of hydrogen include protium, deuterium, and tritium, isotopes of carbon include $^{13}C$ and $^{14}C$, and isotopes of oxygen include $^{16}O$ and $^{18}O$.

DETAILED DESCRIPTION

The following representative examples are intended to better illustrate the disclosure and are not intended to limit the scope of the disclosure. The materials used in the following examples are commercially available unless otherwise specified.

Example 1: 3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)cyclobutane-1-carboxylic Acid

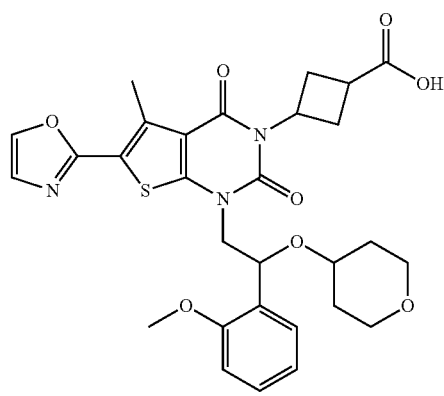 [SMILES: COc1ccccc1C(Cn1c(=O)n(C2CC(C(=O)O)C2)c(=O)c2c(C)c(-c3ncco3)sc21)OC1CCOCC1]

Step 1: Preparation of ethyl 3-oxocyclobutanecarboxylate

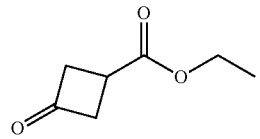

In a 1000 mL single-necked flask, 3-oxocyclobutanecarboxylic acid (25.0 g, 219.1 mmol) was dissolved in toluene (500 mL) and triethyl orthoacetate (106.6 g, 657.3 mmol) was added. The mixture was stirred under heating at 110° C. for 5 h. After the completion of the reaction, the mixture was cooled to room temperature. The reaction was quenched with diluted hydrochloric acid (1.0 M, 20 mL). The organic layer was separated, washed with a saturated aqueous solution of sodium carbonate and a saturated aqueous solution of sodium chloride once in sequence, dried over anhydrous sodium sulfate and then filtered. The filtrate was concentrated to obtain 24.9 g of the title compound, which was directly used in the next reaction without purification.

Step 2: Preparation of ethyl 3-(dibenzylamino)cyclobutanecarboxylate

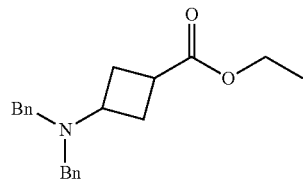 [SMILES: CCOC(=O)C1CC(N(Cc2ccccc2)Cc2ccccc2)C1]

Ethyl 3-oxocyclobutanecarboxylate (20.0 g, 140.7 mmol) was dissolved in anhydrous tetrahydrofuran (800 mL). Glacial acetic acid (80 mL), dibenzylamine (30.5 g, 154.8 mmol), sodium triacetoxyborohydride (59.6 g, 281.4 mmol)

were added and stirred at room temperature overnight. After the completion of the reaction, the mixture was filtered, and the filtrate was concentrated and 600 ml dichloromethane was added for dissolving. The mixture was washed once with water, a saturated sodium bicarbonate aqueous solution and a saturated sodium chloride aqueous solution in order. The organic layer was dried over anhydrous sodium sulfate and filtered. The filtrate was concentrated and subjected to silica-gel column chromatography (petroleum ether:ethyl acetate=8:1) to obtain 28.7 g of the title compound with a yield of 63%. MS (ESI) m/z 324.2 [M+H]$^+$.

Step 3: Preparation of ethyl 3-aminocyclobutanecarboxylate

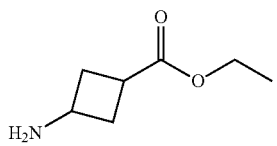

Ethyl 3-(dibenzylamino)cyclobutanecarboxylate (25.0 g, 77.3 mmol) was dissolved in methanol (1000 mL), and 10% Pd/C (6.2 g), ammonium formate (48.8 g, 773.9 mmol) were added in sequence. The mixture was heated at 70° C. for 1.5 h. After the completion of the reaction, the reaction mixture was filtered with celite. The filtrate was concentrated, ethyl acetate (500 mL) was added, and then washed with a saturated aqueous solution of sodium chloride twice. The organic layer was dried over anhydrous sodium sulfate, filtered and the filtrate was concentrated to obtain the title compound, which was directly used in the next reaction without purification.

Step 4: Preparation of ethyl 2-(3-(3-(ethoxycarbonyl)cyclobutyl)ureido)-4-methylthiophene-3-carboxylate

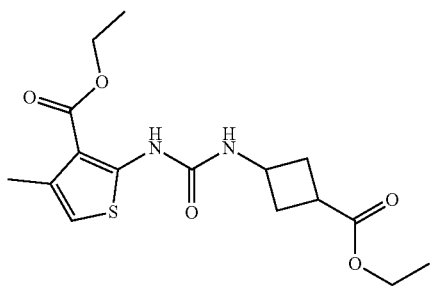 [SMILES: CCOC(=O)c1c(C)csc1NC(=O)NC1CC(C(=O)OCC)C1]

At −5° C., a solution of ethyl 2-amino-4-methyl-3-carboxylate (12.2 g, 65.6 mmol) and triethylamine (26.6 g, 262.4 mmol) in anhydrous dichloromethane (450 mL) was added dropwise to a solution of triphosgene (19.5 g, 65.6 mmol) in anhydrous dichloromethane (150 mL). After completion of the dropwise addition, the mixture was stirred at room temperature for 1 h, and then ethyl 3-aminocyclobutanecarboxylate (9.4 g, 65.6 mmol) was added, and the mixture was stirred at room temperature overnight. After completion of the reaction, the reaction mixture was concentrated, mixed with water (400 mL), and then extracted with ethyl acetate (400 mL×3). The organic layer was dried over anhydrous sodium sulfate and filtered, The filtrate was concentrated and subjected to silica-gel column chromatography (dichloromethane:methanol=40:1) to obtain 14.2 g of the title compound with a yield of 61%. MS (ESI) m/z 355.1 [M+H]$^+$ Step 5: Preparation of ethyl 3-(5-methyl-2,4-dioxo-1,4-dihydrothieno[2,3-d]pyrimidin-3(2H)-yl)cyclobutanecarboxylate

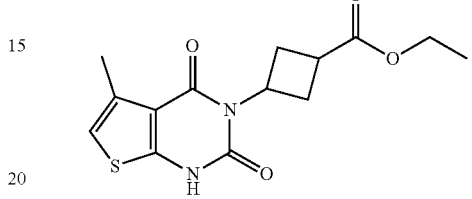

In a 500 mL two-necked flask, ethyl 2-(3-(3-(ethoxycarbonyl)cyclobutyl)ureido)-4-methylthiophene-3-carboxylate (13.0 g, 36.7 mmol) was dissolved in anhydrous tetrahydrofuran (230 mL). Under argon protection, sodium hydride (1.3 g, 55.0 mmol) was added, and then the mixture was heated and refluxed at 110° C. for 2 h. After completion of the reaction, the mixture was cooled to room temperature. The reaction was quenched with saturated solution of ammonium chloride (300 mL), and the mixture was extracted with ethyl acetate (400 mL×3). The organic layer was dried over anhydrous sodium sulfate and filtered. The filtrate was concentrated and subjected to silica-gel column chromatography (dichloromethane:methanol=80:1) to obtain 5.8 g of the title compound with a yield of 51%. MS (ESI) m/z 309.1 [M+H]$^+$.

Step 6: Preparation of ethyl 3-(1-(2-(2-methoxyphenyl)-2-((tetrahydro-2H-pyran-4-yl)oxy)ethyl)-5-methyl-2,4-(2-oxo-1,4-dihydrothieno[2,3-d]pyrimidin-3(2H)-yl)cyclobutanecarboxylate

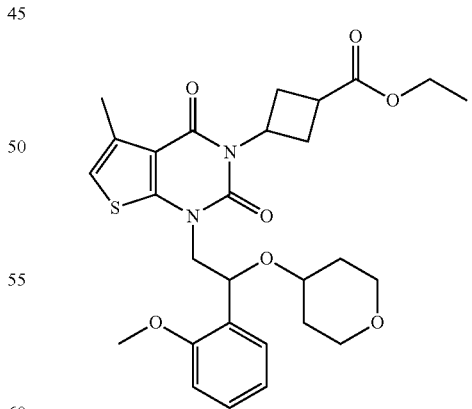

In a 250 mL three-necked flask, ethyl 3-(5-methyl-2,4-dioxo-1,4-dihydrothieno[2,3-d]pyrimidin-3(2H)-yl)cyclobutanecarboxylate (2.0 g, 6.4 mmol) and triphenylphosphine (5.1 g, 19.4 mmol) was added. Under argon protection, anhydrous tetrahydrofuran (100 mL) was added for dissolving, and then 2-(2-methoxyphenyl) 2-(4-tetrahydropyranyloxy)ethanol (1.6 g, 6.5 mmol) and diisopropyl azodicarboxylate (DIAD) (3.9 g, 19.4 mmol) were added in sequence and stirred at 40° C. overnight. After completion of the reaction, the mixture was directly subjected to silica-gel column chromatography (petroleum ether:ethyl acetate=6:1) to obtain 1.7 g of the title compound with a yield of 48%. MS (ESI) m/z 543.2 [M+H]$^+$.

Step 7: Preparation of ethyl 3-(6-bromo-1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)cyclobutane-1-carboxylate

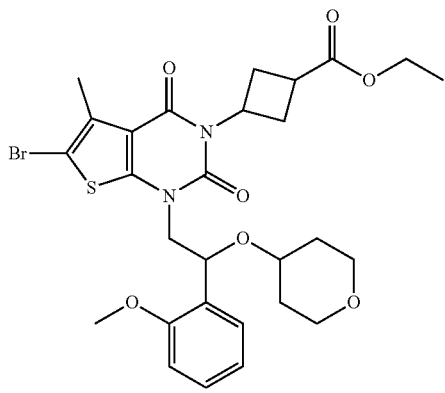 [SMILES: CCOC(=O)C1CC(n2c(=O)c3c(C)c(Br)sc3n(CC(OC3CCOCC3)c3ccccc3OC)c2=O)C1]

In a 100 mL single-necked flask, ethyl 3-(1-(2-(2-methoxyphenyl)-2-((tetrahydro-2H-pyran-4-yl)oxy)ethyl)-5)-methyl-2,4-dioxo-1,4-dihydrothieno[2,3-d]pyrimidin-3(2H)-yl)cyclobutanecarboxylate (0.725 g, 1.336 mmol) was dissolved in chloroform (20 mL), followed by addition of N-Bromosuccinimide (0.262 g, 1.470 mmol) and azobisisobutyronitrile (0.022 g, 0.134 mmol) in sequence. The mixture was stirred at room temperature for 2 h. After completion of the reaction, the mixture was directly subjected to silica-gel column chromatography (petroleum ether:ethyl acetate=5:1) to obtain 0.778 g of the title compound with a yield of 94%. MS (ESI) m/z 621.1 [M+H]$^+$.

Step 8: Preparation of ethyl 3-(1-(2-(2-methoxyphenyl)-2-((tetrahydro-2H-pyran-4-yl)oxy)ethyl)-5-methyl-6(oxazol-2-yl)-4-dioxo-1,4-dihydrothieno[2,3-d]pyrimidin-3(2H)-yl)cyclobutanecarboxylate

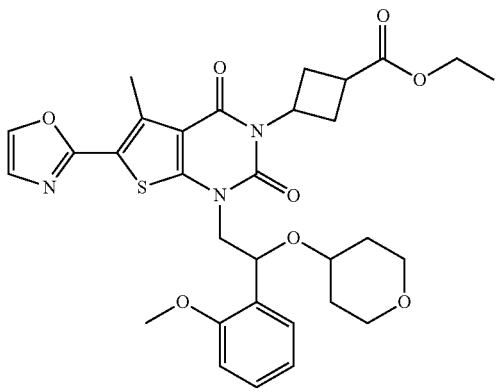 [SMILES: CCOC(=O)C1CC(n2c(=O)c3c(C)c(-c4ncco4)sc3n(CC(OC3CCOCC3)c3ccccc3OC)c2=O)C1]

In a 25 mL two-necked flask, ethyl 3-(6-bromo-1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)cyclobutane-1-carboxylate (0.753 g, 1.212 mmol), tris(dibenzylideneacetone)dipalladium (0.111 g, 0.121 mmol) and 2-dicyclohexylphosphino-2,4,6-triisopropylbiphenyl (0.231 g, 0.485 mmol) were added. Under argon protection, anhydrous toluene (9 mL) was added, and then 2-tri-n-butyltinoxazole (0.870 g, 2.423 mmol) was added. The mixture was stirred at 90° C. overnight. After completion of the reaction, the mixture was directly subjected to silica-gel column chromatography (petroleum ether:ethyl acetate=5:1) to obtain 0.364 g of the title compound with a yield of 49%. MS (ESI) m/z 610.2 [M+H]$^+$.

Step 9: Preparation of 3-(1-(2-(2-methoxyphenyl)-2-((tetrahydro-2H-pyran-4-yl)oxy)ethyl)-5-methyl-6-(oxazol-2-yl)-2, 4-dioxo-1,2-dihydrothieno[2,3-d]pyrimidin-3(4H)-yl)cyclobutanecarboxylic Acid

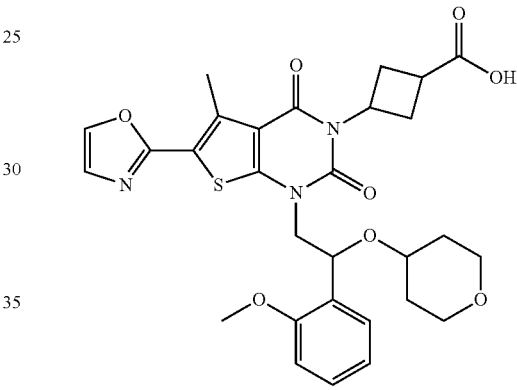

In a 25 mL single-necked flask, ethyl 3-(1-(2-(2-methoxyphenyl)-2-((tetrahydro-2H-pyran-4-yl)oxy)ethyl)-5-methyl-6-(oxazol-2-yl)-4-dioxo-1,4-dihydrothieno[2,3-d]pyrimidin-3(2H)-yl)cyclobutanecarboxylate (0.200 g, 0.328 mmol) was dissolved in ethanol (10 mL), and sodium hydroxide solution (1.0 M, 4.0 mL) was added. The reaction was carried out at room temperature for 0.5 h. After completion of the reaction, most of the ethanol was removed by concentration. The resultant was acidified to pH 3-4 with diluted hydrochloric acid (1.0 M), extracted with ethyl acetate (10 mL×3). The organic layers were combined and washed twice with saturated aqueous solution of sodium chloride. The organic layer was dried over anhydrous sodium sulfate and filtered, and the filtrate was concentrated and subjected to silica-gel column chromatography (dichloromethane:methanol=25:1) to obtain 0.074 g of the title compound with a yield of 39%. $^1$H NMR (400 MHz, CDCl$_3$) δ 7.71 (d, 1H), 7.55 (dd, 1H), 7.32-7.27 (m, 1H), 7.22 (d, 1H), 7.02 (t, 1H), 6.86 (d, 1H), 5.44-5.38 (m, 1H), 5.36-5.30 (m, 1H), 4.22-4.03 (m, 2H), 3.86 (s, 3H), 3.79-3.65 (m, 2H), 3.47-3.39 (m, 1H), 3.37-3.28 (m, 2H), 3.19-3.07 (m, 2H), 3.07-2.95 (m, 1H), 2.88 (s, 3H), 2.75-2.65 (m, 2H), 1.77-1.69 (m, 2H), 1.58-1.50 (m, 1H), 1.43-1.35 (m, 1H). MS (ESI) m/z 580.1 [M−H]$^−$.

Example 2: 3-(3,3-Difluorocyclobutyl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione

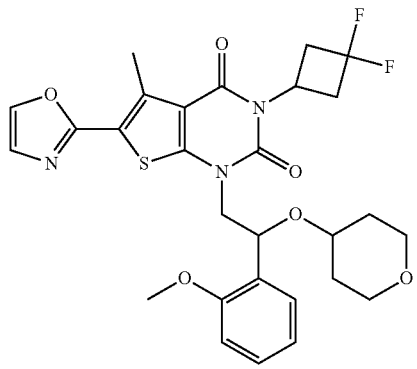 [SMILES: COc1ccccc1C(Cn1c(=O)n(C2CC(F)(F)C2)c(=O)c2c(C)c(-c3ncco3)sc21)OC1CCOCC1]

Step 1: Preparation of ethyl 2-(3-(3,3-difluorocyclobutylamino)ureido)-4-methyl-thiophene-3-carboxylate

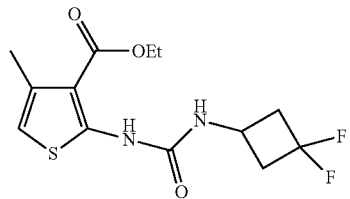 [SMILES: CCOC(=O)c1c(C)csc1NC(=O)NC1CC(F)(F)C1]

At −5° C., a solution of ethyl 2-amino-4-methylthiophene-3-carboxylate (5.786 g, 19.5 mmol) and triethylamine (11.84 g, 117 mmol) in anhydrous dichloromethane (110 mL) was added dropwise to a solution of triphosgene (5.786 g, 19.5 mmol) in anhydrous dichloromethane (50 mL). After completion of the dropwise addition, the mixture was stirred at 0° C. for 1.5 h, and then transferred to room temperature. 3,3-Difluorocyclobutylamine (2.8 g, 19.5 mmol) was added and the reaction was carried out overnight. The mixture was concentrated and subjected to silica-gel column chromatography. The resultant was dispersed with ethyl acetate. The product was dissolved in ethyl acetate. The mother liquor was concentrated to give 4.5 g of the title compound with a yield of 80%. MS (ESI) m/z 319.1 [M+H]$^+$.

Step 2: Preparation of 3-(3,3-difluorocyclobutyl)-5-methylthieno[2,3-d]pyrimidine-2,4(1H,3H)-dione

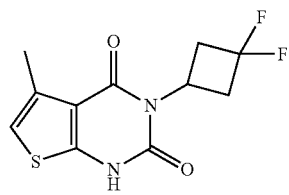 [SMILES: Cc1csc2[nH]c(=O)n(C3CC(F)(F)C3)c(=O)c12]

In a 250 mL two-necked flask, ethyl 2-(3-(3,3-difluorocyclobutylamino)ureido)-4-methyl-thiophene-3-carboxylate (2.5 g, 7.86 mmol) was dissolved in anhydrous tetrahydrofuran (20 mL) and anhydrous N,N-dimethylformamide (15 mL). Under argon protection, sodium hydride (0.472 g, 11.79 mmol) was added, and then the mixture was heated and refluxed at 110° C. for 2 h. After completion of the reaction, the mixture was cooled to room temperature. The reaction was quenched with saturated solution of ammonium chloride (40 mL), and the mixture was extracted with ethyl acetate (40 mL×3). The organic layer was dried over anhydrous sodium sulfate and filtered, and the filtrate was concentrated and subjected to silica-gel column chromatography (petroleum ether:ethyl acetate=3:1) to obtain 1.5 g of the title compound with a yield of 70%. MS (ESI) m/z 273.2 [M+H]$^+$.

Step 3: Preparation of 3-(3,3-difluorocyclobutyl)-1-(2-(2-methoxyphenyl)-2-((tetrahydro-2H-pyran-4-yl)oxy)ethyl)-5-methylthieno[2,3-d]pyrimidine-2,4(1H,3H)-dione

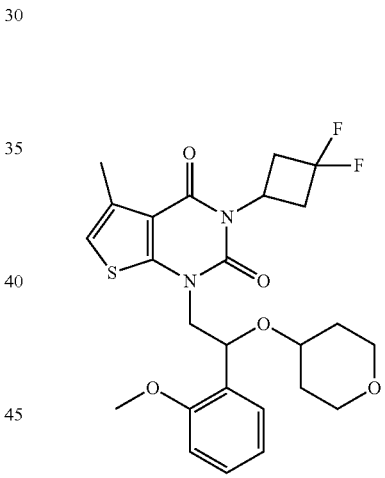

3-(3,3-Difluorocyclobutyl)-5-methylthieno[2,3-d]pyrimidine-2,4(1H,3H)-dione (1.5 g, 5.5 mmol) was dissolved in N,N-dimethylformamide (10 mL), and anhydrous potassium carbonate (2.277 g, 16.5 mmol) and 4-(2-bromo-1-(2-methoxyphenyl)ethoxy)tetrahydro-2H-pyran (2.079 g, 6.6 mmol) were added, and the mixture was stirred at 130° C. overnight. After completion of the reaction, water (30 mL) was added, and the mixture was extracted with ethyl acetate (150 mL×3). The organic layer was dried over anhydrous sodium sulfate and filtered, and the filtrate was concentrated and subjected to silica-gel column chromatography (petroleum ether:ethyl acetate=3:1) to obtain 1.9 g of the title compound with a yield of 68%. MS (ESI) m/z 507.2 [M+H]$^+$.

Step 4: Preparation of 3-(3,3-difluorocyclobutyl)-1-(2-(2-methoxyphenyl)-2-((tetrahydro-2H-pyran-4-yl)oxy)ethyl)-5-methyl-6-bromothieno[2,3-d]pyrimidine-2,4(1H,3H)-dione

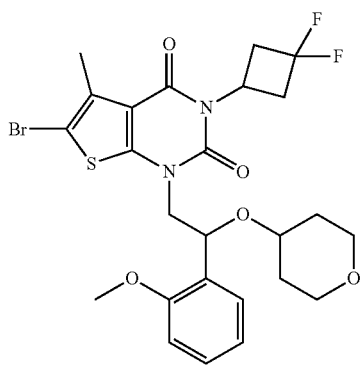 [SMILES: COc1ccccc1C(Cn1c(=O)n(C2CC(F)(F)C2)c(=O)c2c(C)c(Br)sc21)OC1CCOCC1]

3-(3,3-Difluorocyclobutyl)-1-(2-(2-methoxyphenyl)-2-((tetrahydro-2H-pyran-4-yl)oxy)ethyl)-5-methylthieno[2,3-d]pyrimidine-2,4(1H,3H)-dione (0.9 g, 1.78 mmol) was dissolved in chloroform (250 mL), and N-bromo succinimide (0.348 g, 1.96 mmol) and azobisisobutyronitrile (0.025 g, 0.154 mmol) were added in sequence. The mixture was stirred at room temperature for 2 h. After completion of the reaction, the mixture was directly subjected to silica-gel column chromatography (petroleum ether:ethyl acetate=6:1) to obtain 0.9 g of the title compound with a yield of 87%. MS (ESI) m/z 585.1 [M+H]$^+$.

Step 5: Preparation of 3-(3,3-difluorocyclobutyl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione

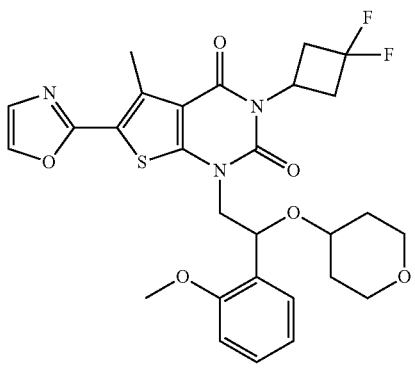 [SMILES: COc1ccccc1C(Cn1c(=O)n(C2CC(F)(F)C2)c(=O)c2c(C)c(-c3ncco3)sc21)OC1CCOCC1]

Under argon protection, to 3-(3,3-difluorocyclobutyl)-1-(2-(2-methoxyphenyl)-2-((tetrahydro-2H-pyran-4-yl)oxy)ethyl)-5-methyl-6-bromothieno[2,3-d]pyrimidine-2,4(1H,3H)-dione (0.40 g, 0.685 mmol), tris(dibenzalacetone)dipalladium (0.063 g, 0.0685 mmol) and 2-dicyclohexylphosphine-2,4,6-triisopropylbiphenyl (0.131 g, 0.274 mmol), anhydrous toluene (7 mL) was added, and then 2-tri-n-butyltinoxazole (0.492 g, 1.37 mmol) was added. The mixture was stirred at 90° C. for 5 h. After completion of the reaction, the mixture was directly subjected to silica-gel column chromatography (petroleum ether:ethyl acetate=3:1) to obtain 0.200 g of the title compound with a yield of 51%. $^1$H NMR (400 MHz, CDCl$_3$) δ 7.71 (d, 1H), 7.55 (dd, 1H), 7.31 (dd, 1H), 7.22 (s, 1H), 7.03 (t, 1H), 6.86 (d, 1H), 5.41 (t, 1H), 5.37-5.29 (m, 1H), 4.20-4.07 (m, 2H), 3.86 (s, 3H), 3.79-3.72 (m, 1H), 3.72-3.64 (m, 1H), 3.64-3.48 (m, 2H), 3.46-3.40 (m, 1H), 3.38-3.27 (m, 2H), 2.95-2.81 (m, 2H), 2.89 (s, 1H), 1.78-1.68 (m, 2H), 1.55-1.48 (m, 1H), 1.42-1.34 (m, 1H). MS (ESI) m/z 574.2 [M+H]$^+$.

Example 3: Preparation of (1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)-1-methylcyclobutanecarboxylic Acid

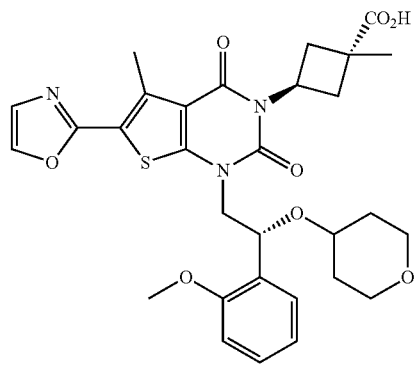 [SMILES: COc1ccccc1[C@H](Cn1c(=O)n([C@H]2C[C@](C)(C(=O)O)C2)c(=O)c2c(C)c(-c3ncco3)sc21)OC1CCOCC1]

Step 1: Preparation of methyl 3-(dibenzylamino)-1-methylcyclobutanecarboxylate

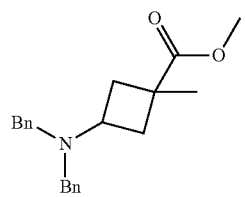 [SMILES: COC(=O)C1(C)CC(N(Cc2ccccc2)Cc2ccccc2)C1]

In a 1000 mL single-necked flask, methyl 1-methyl-3-oxo-cyclobutyrate (4.95 g, 34.8 mmol) was dissolved in anhydrous tetrahydrofuran (200 mL), followed by the addition of glacial acetic acid (22 mL), dibenzylamine (7.56 g, 38.3 mmol), sodium triacetoxyborohydride (14.8 g, 69.7 mmol) in sequence. The mixture was stirred at room temperature overnight. After completion of the reaction, the mixture was filtered. The filtrate was concentrated and dissolved in dichloromethane (300 ml). The mixture was washed with water, saturated aqueous solution of sodium bicarbonate and saturated aqueous solution of sodium chloride once in sequence. The organic layer was dried over anhydrous sodium sulfate and filtered, and the filtrate was concentrated and subjected to silica-gel column chromatography (petroleum ether:ethyl acetate=8:1) to obtain 10.4 g of the title compound with a yield of 92%. MS (ESI) m/z 324.2 [M+H]$^+$.

Step 2: Preparation of methyl 3-amino-1-methylcyclobutanecarboxylate

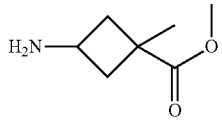

In a 2000 mL single-necked flask, methyl 3-(dibenzylamino)-1-methylcyclobutanecarboxylate (10.4 g, 32.2 mmol) was dissolved in methanol (410 mL), followed by addition of 6.46 g of 10% Pd/C, ammonium formate (20.3 g, 321.6 mmol) in sequence. The mixture was heated at 70° C. for 1.5 h. The mixture was cooled to room temperature, filtered with celite. The filtrate was concentrated, and ethyl acetate (400 mL) was added. The mixture was washed with saturated aqueous solution of sodium chloride twice. The organic layer was dried over anhydrous sodium sulfate and filtered, and the filtrate was concentrated to obtain the title compound which was directly used in the next step. MS (ESI) m/z 144.2 [M+H]$^+$.

Step 3: Preparation of (R)-4-(2-bromo-1-(2-methoxyphenyl)ethoxy) tetrahydro-2H-pyran

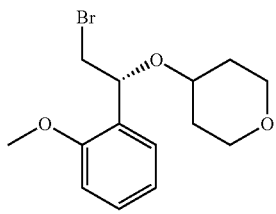 [SMILES: COc1ccccc1[C@H](CBr)OC1CCOCC1]

(R)-2-(2-Methoxyphenyl)-2-((tetrahydro-2H-pyran-4-yl)oxy)ethanol (0.600 g, 2.38 mmol) and carbon tetrabromide (1.18 g, 3.57 mmol) were added in a 50 mL single-necked flask. Under nitrogen protection, anhydrous tetrahydrofuran (10 mL) was added, and triphenylphosphine (0.936 g, 3.57 mmol) was added. The mixture was stirred at room temperature overnight. After completion of the reaction, the mixture was filtered, and the filtrate was concentrated and subjected to silica-gel column chromatography (petroleum ether:ethyl acetate=12:1) to obtain 0.610 g of the title compound with a yield of 81%. MS (ESI) m/z 315.0 [M+H]$^+$.

Step 4: Preparation of ethyl 2-(3-(3-(methoxycarbonyl)-3-methylcyclobutyl)ureido)-4-methylthiophene-3-carboxylate

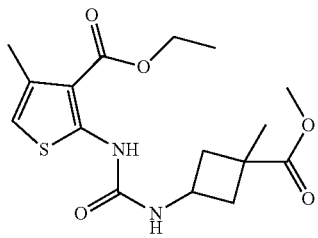 [SMILES: CCOC(=O)c1c(C)csc1NC(=O)NC1CC(C)(C(=O)OC)C1]

In a 1000 mL single-necked flask, triphosgene (9.56 g, 32.2 mmol) was dissolved in anhydrous dichloromethane (70 mL) and the mixture was put at −5° C. Methyl 2-amino-4-methylthiophene-3-carboxylate (5.97 g, 32.2 mmol) and triethylamine (13.0 g, 128.8 mmol) were dissolved in anhydrous dichloromethane (140 mL), which was added dropwise to the above solution of triphosgene in dichloromethane. After completion of the dropwise addition, the mixture was stirred at room temperature for 1 h, and then methyl 3-amino-1-methylcyclobutylcarboxylate (4.6 g, 32.2 mmol) was added, and the mixture was stirred at room temperature overnight. After completion of the reaction, the mixture was concentrated, mixed with water (250 mL) and extracted with ethyl acetate (250 mL×3). The organic layer was dried over anhydrous sodium sulfate and filtered, and the filtrate was concentrated and subjected to silica-gel column chromatography (dichloromethane:methanol=40:1) to obtain 5.2 g of the title compound with a yield of 46%. MS (ESI) m/z 355.1 [M+H]$^+$.

Step 5: Preparation of methyl 1-methyl-3-(5-methyl-2,4-dioxo-1,4-dihydrothieno[2,3-d] pyrimidin-3(2H)-yl)cyclobutanecarboxylate

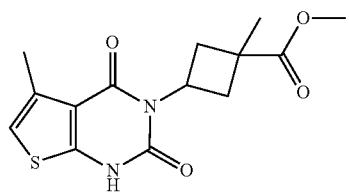 [SMILES: COC(=O)C1(C)CC(n2c(=O)[nH]c3scc(C)c3c2=O)C1]

Ethyl 2-(3-(3-(methoxycarbonyl)-3-methylcyclobutyl)ureido)-4-methylthiophene-3-carboxylate (3.34 g, 9.42 mmol) was dissolved in anhydrous N,N-dimethylformamide (77 mL), and anhydrous cesium carbonate (7.67 g, 23.6 mmol) was added. The mixture was heated and stirred at 80° C. for 4 h. After completion of the reaction, the mixture was cooled to room temperature and ethyl acetate (100 mL) was added. The mixture was washed with saturated aqueous solution of sodium chloride (100 mL×3). The organic layer was dried over anhydrous sodium sulfate and filtered, and the filtrate was concentrated, dispersed with ethyl acetate and purified to obtain 1.3 g of the title compound with a yield of 45%. MS (ESI) m/z 309.1 [M+H]$^+$.

Step 6: Preparation of methyl (1R,3r)-3-(1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)-1-methylcyclobutanecarboxylate

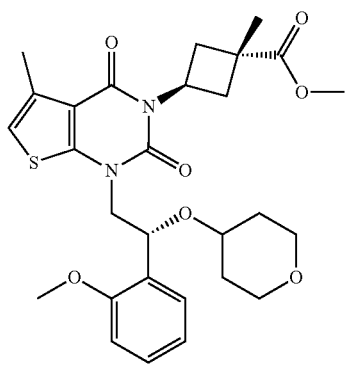 [SMILES: COc1ccccc1[C@H](Cn1c(=O)n([C@H]2C[C@](C)(C(=O)OC)C2)c(=O)c2c(C)csc21)OC1CCOCC1]

In a 100 mL two-necked flask, methyl 1-methyl-3-(5-methyl-2,4-dioxo-1,4-dihydrothieno[2,3-d]pyrimidine-3(2H)-yl)cyclobutanecarboxylate (0.523 g, 1.70 mmol) was dissolved in N,N-dimethylformamide (13 mL), and anhydrous potassium carbonate (0.703 g, 5.09 mmol) and (R)-4-(2-bromo-1-(2-methoxyphenyl)ethoxy)tetrahydro-2H-pyran (0.534 g, 1.7 mmol) were added. The mixture was heated and stirred at 120° C. overnight. After completion of the reaction, water (50 mL) was added, and the mixture was extracted with ethyl acetate (60 mL×3). The organic layer was dried over anhydrous sodium sulfate and filtered, and the filtrate was concentrated and subjected to silica-gel column chromatography (petroleum ether:ethyl acetate=5:1) to obtain 0.286 g of the title compound with a yield of 30%.

Step 7: Preparation of methyl (1R,3r)-3-(6-bromo-1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)-1-methylcyclobutanecarboxylate

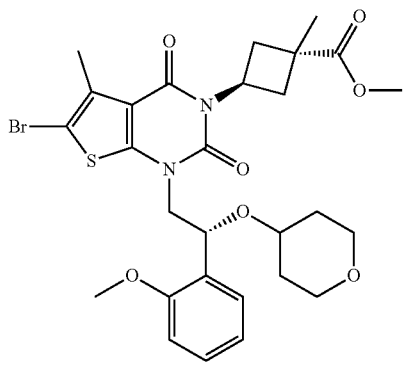 [SMILES: COc1ccccc1[C@H](Cn1c(=O)n([C@H]2C[C@](C)(C(=O)OC)C2)c(=O)c2c(C)c(Br)sc21)OC1CCOCC1]

In a 50 mL single-necked flask, methyl (1R,3r)-3-(1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)-1-methylcyclobutanecarboxylate (0.286 g, 0.527 mmol) was dissolved in chloroform (8 mL), followed by addition of N-bromosuccinimide (0.103 g, 0.580 mmol) and azobisisobutyronitrile (0.009 g, 0.053 mmol) in sequence. The mixture was stirred at room temperature for 2 h. After completion of the reaction, the mixture was directly subjected to silica-gel column chromatography (petroleum ether:ethyl acetate=7:1) to obtain 0.244 g of the title compound with a yield of 74%.

Step 8: Preparation of methyl (1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)-1-methylcyclobutanecarboxylate

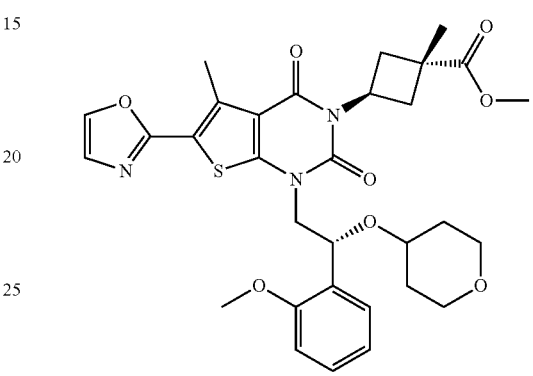

In a 25 mL two-necked flask, methyl (1R,3r)-3-(6-bromo-1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)-1-methylcyclobutanecarboxylate (0.244 g, 0.392 mmol), tris(dibenzylideneacetone)dipalladium (0.036 g, 0.039 mmol) and 2-dicyclohexylphosphorin-2,4,6-triisopropylbiphenyl (0.075 g, 0.157 mmol) were added. Under argon protection, anhydrous toluene (5 mL) and 2-tri-n-butyltinoxazole (0.282 g, 0.785 mmol) were added, and the mixture was stirred at 90° C. overnight. After completion of the reaction, the mixture was directly subjected to silica-gel column chromatography (petroleum ether:ethyl acetate=5:1) to obtain 0.175 g of the title compound with a yield of 73%.

Step 9: Preparation of (1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)-1-methylcyclobutanecarboxylic Acid

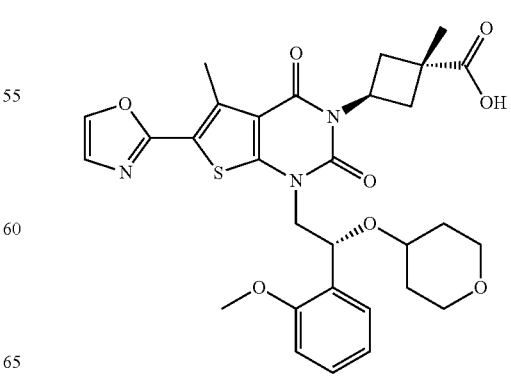

In a 25 mL single-necked flask, methyl (1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)-1-methylcyclobutanecarboxylate (0.175 g, 0.287 mmol) was dissolved in methanol (6 mL), and then sodium hydroxide solution (1.0 M, 6 mL) was added. The reaction was carried out at room temperature for 1 h. After completion of the reaction, the mixture was adjusted with diluted hydrochloric acid (2 M) to a weak acidity, and extracted with ethyl acetate (20 mL×3). The organic layer was combined and washed twice with saturated aqueous solution of sodium chloride. The organic layer was dried over anhydrous sodium sulfate and filtered, and the filtrate was concentrated and subjected to silica-gel column chromatography (dichloromethane:methanol=20:1) to obtain 0.068 g of the title compound with a yield of 40%. $^1$H NMR (400 MHz, CDCl$_3$) δ 7.70 (s, 1H), 7.57 (dd, 1H), 7.32-7.27 (m, 1H), 7.24-7.20 (m, 1H), 7.02 (t, 1H), 6.85 (d, 1H), 5.65-5.55 (m, 1H), 5.45-5.39 (m, 1H), 4.17-4.04 (m, 2H), 3.90-3.83 (m, 3H), 3.79-3.72 (m, 1H), 3.72-3.64 (m, 1H), 3.47-3.41 (m, 1H), 3.37-3.29 (m, 2H), 3.05-2.96 (m, 2H), 2.92-2.87 (m, 3H), 2.84-2.77 (m, 2H), 1.73 (dd, 2H), 1.59 (s, 3H), 1.55-1.49 (m, 1H), 1.40-1.35 (m, 1H). MS (ESI) m/z 594.2 [M−H]$^-$.

Example 4: (1S,3s)-3-(1-((R)-2-(2-methoxyphenyl)-2-((tetrahydro-2H-pyran-4-yl)oxy) ethyl)-5-methyl-6-(oxazol-2-yl)-2,4-dioxo-1,4-dihydrothieno[2,3-d]pyrimidine-3(2H)-yl)-1-methylcyclobutanecarboxylic Acid

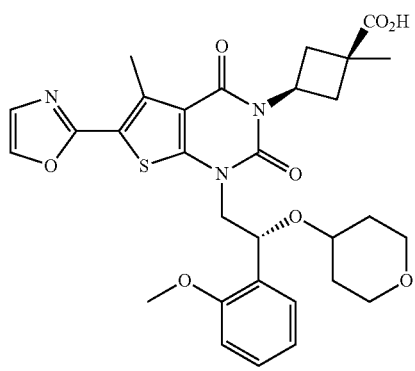 [SMILES: COc1ccccc1[C@H](Cn1c(=O)n([C@H]2C[C@@](C)(C(=O)O)C2)c(=O)c2c(C)c(-c3ncco3)sc21)OC1CCOCC1]

Step 1: Preparation of methyl (1S,3s)-3-(1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl-1-methylcyclobutanecarboxylate

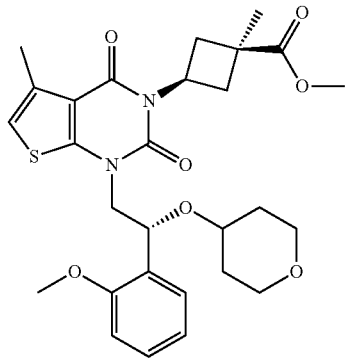 [SMILES: COc1ccccc1[C@H](Cn1c(=O)n([C@H]2C[C@@](C)(C(=O)OC)C2)c(=O)c2c(C)csc21)OC1CCOCC1]

In a 100 mL two-necked flask, methyl 1-methyl-3-(5-methyl-2,4-dioxo-1,2-dihydrothieno[2,3-d]pyrimidine-3(4H)-yl)cyclobutanecarboxylate (0.523 g, 1.70 mmol) was dissolved in N,N-dimethylformamide (13 mL), and anhydrous potassium carbonate (0.703 g, 5.09 mmol) and (R)-4-(2-bromo-1-(2-methoxyphenyl)ethoxy)tetrahydro-2H-pyran (0.534 g, 1.7 mmol) were added. The mixture was heated and stirred at 120° C. overnight. After completion of the reaction, water (50 mL) was added, and the mixture was extracted with ethyl acetate (60 mL×3). The organic layer was dried over anhydrous sodium sulfate and filtered, and the filtrate was concentrated and subjected to silica-gel column chromatography (petroleum ether:ethyl acetate=5:1) to obtain 0.272 g of the title compound with a yield of 28%.

Step 2: Preparation of methyl (1S,3s)-3-(6-bromo-1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)-1-methylcyclobutanecarboxylate In a 50 mL single-necked flask, methyl (1S,3s)-3-(1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl-1-methylcyclobutanecarboxylate (0.272 g, 0.501 mmol) was dissolved in chloroform (8 mL), followed by addition of N-bromosuccinimide (0.098 g, 0.551 mmol)

and azobisisobutyronitrile (0.009 g, 0.053 mmol) in sequence. The mixture was stirred at room temperature for 2 h. After completion of the reaction, the mixture was directly subjected to silica-gel column chromatography (petroleum ether:ethyl acetate=7:1) to obtain 0.231 g of the title compound with a yield of 74%.

Step 3: Preparation of methyl (1S,3s)-3-(1-((R)-2-(2-methoxyphenyl)-2-((tetrahydro-2H-pyran-4-yl)oxy)ethyl)-5-methyl-6-(oxazol-2-yl)-2, 4-dioxo-1,4-dihydrothieno[2,3-d]pyrimidine-3(2H)-1-methylcyclobutanecarboxylate

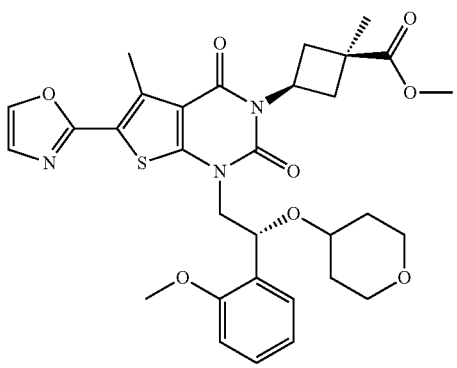 [SMILES: COc1ccccc1[C@H](Cn1c(=O)n([C@H]2C[C@@](C)(C(=O)OC)C2)c(=O)c2c(C)c(-c3ncco3)sc21)OC1CCOCC1]

In a 25 mL two-necked flask, methyl (1R,3r)-3-(6-bromo-1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)-1-methylcyclobutanecarboxylate (0.227 g, 0.365 mmol), tris(dibenzylideneacetone)dipalladium (0.034 g, 0.036 mmol) and 2-dicyclohexylphosphorin-2,4,6-triisopropylbiphenyl (0.070 g, 0.146 mmol) were added. Under argon protection, anhydrous toluene (4 mL) and 2-tri-n-butyltinoxazole (0.262 g, 0.730 mmol) were added, and the mixture was stirred at 90° C. overnight. After completion of the reaction, the mixture was directly subjected to silica-gel column chromatography (petroleum ether:ethyl acetate=5:1) to obtain 0.159 g of the title compound with a yield of 71%.

Step 4: Preparation of (1S,3s)-3-(1-((R)-2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl-1-methylcyclobutanecarboxylic Acid

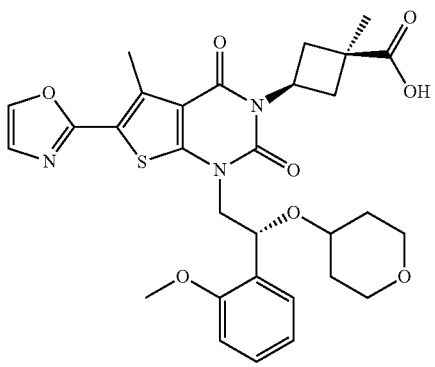 [SMILES: COc1ccccc1[C@H](Cn1c(=O)n([C@H]2C[C@@](C)(C(=O)O)C2)c(=O)c2c(C)c(-c3ncco3)sc21)OC1CCOCC1]

In a 25 mL single-necked flask, methyl (1R,3r)-3-(1-((R)-2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidine-3(2H)-yl)-1-methylcyclobutanecarboxylate (0.159 g, 0.261 mmol) was dissolved in methanol (6 mL), and then sodium hydroxide solution (1.0 M, 6 mL) was added. The reaction was carried out at room temperature for 1 h. After completion of the reaction, the mixture was adjusted with diluted hydrochloric acid (2 M) to a weak acidity, and extracted with ethyl acetate (20 mL×3). The organic layers were combined and washed twice with saturated aqueous solution of sodium chloride. The organic layer was dried over anhydrous sodium sulfate and filtered, and the filtrate was concentrated and subjected to silica-gel column chromatography (dichloromethane:methanol=20:1) to obtain 0.030 g of the title compound with a yield of 19%. $^1$H NMR (400 MHz, CDCl$_3$) δ 7.72 (d, 1H), 7.55-7.50 (m, 1H), 7.32-7.27 (m, 1H), 7.23 (d, 1H), 7.01 (t, 1H), 6.87 (d, 1H), 5.76-5.65 (m, 1H), 5.41 (dd, 1H), 4.26-4.16 (m, 1H), 4.13-4.02 (m, 1H), 3.87 (s, 3H), 3.78-3.65 (m, 2H), 3.47-3.40 (m, 1H), 3.36-3.22 (m, 4H), 2.89 (s, 3H), 2.34-2.25 (m, 2H), 1.76-1.71 (m, 2H), 1.54 (s, 3H), 1.44-1.35 (m, 2H). MS (ESI) m/z 594.2 [M−H]$^−$.

Example 5: 1-(2-(2-methoxyphenyl)-2-((tetrahydro-2H-pyran-4-yl)oxy)ethyl)-5-methyl-3-(7-methylimidazo[1,2-a]pyridin-8-yl)-6-(oxazol-2-yl)thieno[2,3-d]pyrimidine-2,4(1H, 3H)-diketone

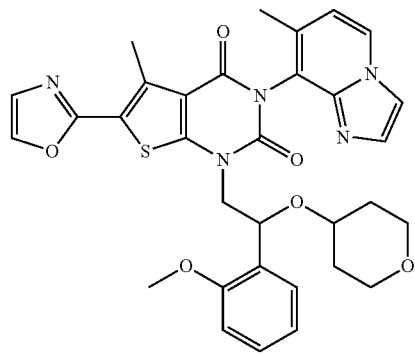 [SMILES: COc1ccccc1C(Cn1c(=O)n(-c2c(C)ccn3ccnc23)c(=O)c2c(C)c(-c3ncco3)sc21)OC1CCOCC1]

Step 1: Preparation of 7-methyl-8-nitroimidazo[1,2-a]pyridine

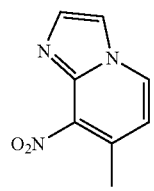

4-methyl-2-aminopyridine (6.10 g, 40.0 mmol) and chloroacetaldehyde (40% aq., 11.2 g, 143 mmol) were added to ethanol (100 mL) and the mixture was heated to reflux at 100° C. After 12 h, the reaction mixture was poured into water (200 mL), adjusted to pH=6-7 with a saturated solution of sodium bicarbonate, and extracted with dichloromethane. The organic layer was combined, washed with saturated solution of sodium chloride, dried over anhydrous sodium sulfate and concentrated, and recrystallized with ethyl acetate to give 5.30 g of the title compound with a yield of 75%. LC-MS m/z 178.1 [M+H]+.

Step 2: Preparation of 7-methyl-8-aminoimidazo[1,2-a]pyridine

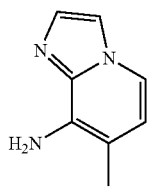

7-Methyl-8-nitroimidazo[1,2-a]pyridine (3.74 g, 20.0 mmol) was added to a mixture of ethanol/water (v/v=9:1, 100 mL) and iron powder (11.0 g, 200 mmol) was added, and concentrated hydrochloric acid (3 drops) was dropwise added. The mixture was heated to reflux at 100° C. After 2 h, the reaction mixture was filtered with celite, and then the filtrate was concentrated, adjusted to pH=6-7 with a saturated solution of sodium bicarbonate, and extracted with dichloromethane. The organic layer was combined, washed with a saturated aqueous solution of sodium chloride and dried over anhydrous sodium sulfate to obtain 2.80 g of the title compound with a yield of 95%. LC-MS m/z 148.2 [M+H]+.

Step 3: Preparation of ethyl 2-amino-5-bromo-4-methylthiophene-3-carboxylate

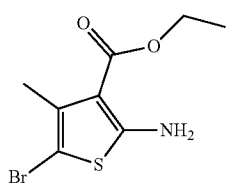

Ethyl 2-amino-4-methylthiophene-3-carboxylate (3.70 g, 20.0 mmol) was added to dichloromethane (50 mL) and the mixture was cooed to −10° C. N-bromosuccinimide (3.70 g, 21.0 mmol) was added portionwise to the reaction mixture. After 1 h, the mixture was added to a saturated aqueous solution of sodium hydrogen carbonate (100 mL), and extracted with ethyl acetate. The organic layer was combined, washed with a saturated sodium chloride solution, dried over anhydrous sodium sulfate and concentrated and then directly used in the next step. LC-MS m/z 264.0 [M+H]+.

Step 4: Preparation of ethyl 5-bromo-4-methyl-2-(3-(7-methylimidazo[1,2-a] pyridin-8-yl)ureido) thiophene-3-carboxylate

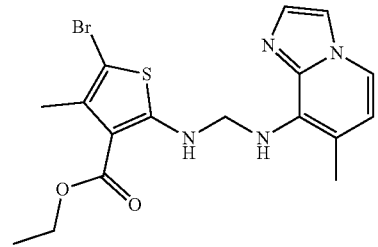 [SMILES: CCOC(=O)c1c(NCNc2c(C)ccn3ccnc23)sc(Br)c1C]

Triphosgene (0.740 g, 2.50 mmol) was added to anhydrous dichloromethane (10 mL), and the mixture was cool to −10° C. A solution of 7-methyl-8-aminoimidazo[1,2-a]pyridine (0.735 g, 5.0 mmol) and triethylamine (1.50 g, 15.0 mmol) in anhydrous dichloromethane was added dropwise. After the dropwise addition, the mixture was stirred in ice bath for 2 h. Ethyl 2-amino-5-bromo-4-methylthiophene-3-carboxylate (5.28 g, 20.0 mmol) was added dropwise. After the dropwise addition, the mixture was stirred at room temperature for 12 h, and then concentrated, and subjected to silica-gel column chromatography (dichloromethane:methanol=1:0-10:1) to obtain 0.9 g of the title compound with a yield of 82%. LC-MS m/z 437.0 [M+H]+.

Step 5: Preparation of 6-bromo-5-methyl-3-(7-methylimidazo[1,2-a]pyridin-8-yl) thieno[2,3-d] pyrimidine-2,4 (1H, 3H)-dione

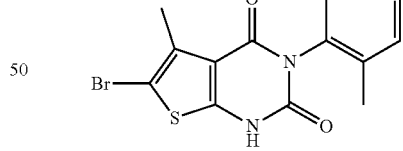

Ethyl 5-bromo-4-methyl-2-(3-(7-methylimidazo[1,2-a] pyridin-8-yl)ureido)thiophene-3-carboxylate (0.90 g, 2.0 Methyl) and cesium carbonate (1.60 g, 5 mmol) were added to ethanol (20 mL), and the mixture was heated to reflux at 100° C. After 3 h, the reaction was completed and the mixture was concentrated and subjected to silica-gel column chromatography (dichloromethane:methanol=1:0-10:1) to obtain 0.70 g of the title compound with a yield of 89%. LC-MS m/z 391.1 [M+H]+.

Step 6: Preparation of 6-bromo-1-(2-(2-methoxyphenyl)-2-((tetrahydro-2H-pyran-4-yl) oxy)ethyl)-5-methyl-3-(7-methylimidazo[1,2-a]pyridin-8-yl)thieno[2,3-d]pyrimidine-2,4(1H,3H)-dione

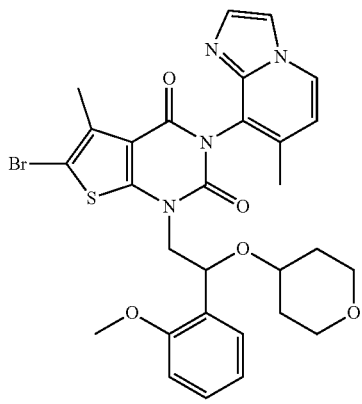 [SMILES: COc1ccccc1C(Cn1c(=O)n(-c2c(C)ccn3ccnc23)c(=O)c2c(C)c(Br)sc21)OC1CCOCC1]

6-Bromo-5-methyl-3-(7-methylimidazo[1,2-a]pyridin-8-yl)thieno[2,3-d]pyrimidine-2,4 (1H,3H)-dione (0.160 g, 0.40 mmol), 4-(2-bromo-1-(2-methoxyphenyl)ethoxy)tetrahydro-2H-pyran (0.251 g, 0.80 mmol), cesium carbonate (0.325 g, 1.00 mmol) were added to anhydrous N,N-dimethylformamide (5 mL), and potassium iodide (0.005 g) was added. The mixture was heated to 120° C. After 12 h, the reaction mixture was poured into water (30 mL), and adjusted to pH=6-7, and extracted with ethyl acetate. The organic layer was combined, washed with saturated sodium chloride, dried over anhydrous sodium sulfate, concentrated, and subjected to silica-gel column chromatography (petroleum ether:ethyl acetate=1:1-1:3) to obtain 0.030 g of the title compound with a yield of 13%. LC-MS m/z 625.1[M+H]$^+$.

Step 7: Preparation of 1-(2-(2-methoxyphenyl)-2-((tetrahydro-2H-pyran-4-yl)oxy)ethyl)-5-methyl-3-(7-methylimidazo[1,2-a]pyridin-8-yl)-6-(oxazol-2-yl)thieno[2,3-d]pyrimidine-2,4(1H,3H)-dione

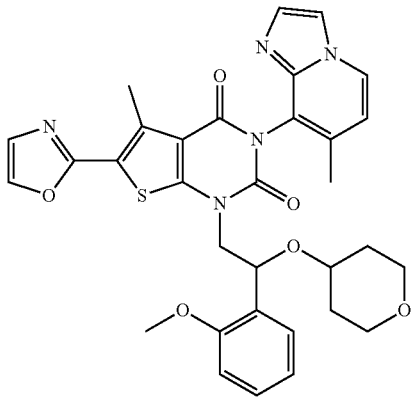 [SMILES: COc1ccccc1C(Cn1c(=O)n(-c2c(C)ccn3ccnc23)c(=O)c2c(C)c(-c3ncco3)sc21)OC1CCOCC1]

6-Bromo-1-(2-(2-methoxyphenyl)-2-((tetrahydro-2H-pyran-4-yl)oxy)ethyl)-5-methyl-3-(7-methylimidazo[1,2-a]pyridin-8-yl)thieno[2,3-d]pyrimidine-2,4(1H,3H)-dione (0.030 g, 0.05 mmol), 2-(tributyltin)oxazole (0.036 g, 0.10 mmol), tris(dibenzylideneacetone)dipalladium (0.009 g, 0.01 mmol), 2-dicyclohexylphosphino-2',4',6'-triisopropylbiphenyl (0.019 g, 0.04 mmol) were added to toluene (2 mL) and the mixture was heated to 90° C. under argon atmosphere. After 8 h, the reaction mixture was concentrated and subjected to silica-gel column chromatography (petroleum ether:ethyl acetate=1:2-1:4) to obtain 0.020 g of the title compound with a yield of 65%. $^1$H NMR (CDCl$_3$, 400 MHz) δ 8.14 (t, 1H), 7.70 (s, 1H), 7.62-7.52 (m, 2H), 7.32-7.23 (m, 1H), 7.23-7.12 (m, 2H), 6.96-6.73 (m, 3H), 5.01-4.88 (m, 1H), 4.68-4.55 (m, 1H), 4.27-4.11 (m, 1H), 3.79 (s, 3H), 3.75-3.52 (m, 2H), 3.29-3.08 (m, 3H), 2.88 (s, 3H), 2.25 (s, 3H), 1.77-1.65 (m, 1H), 1.50-1.40 (m, 1H), 1.39-1.27 (m, 2H). LC-MS m/z 614.2 [M+H]$^+$.

Example 6: 3-(azetidin-3-yl)-1-(2-(2-methoxyphenyl)-2-((tetrahydro-2H-pyran-4-yl) oxy)ethyl)-5-methyl-6-(oxazol-2-yl)thieno[2,3-d]pyrimidine-2,4(1H,3H)-dione

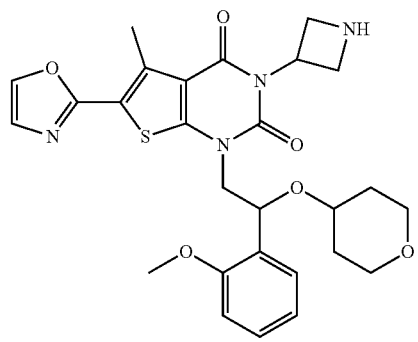 [SMILES: COc1ccccc1C(Cn1c(=O)n(C2CNC2)c(=O)c2c(C)c(-c3ncco3)sc21)OC1CCOCC1]

Step 1: Preparation of diethyl 5-amino-3-methylthiophene-2,4-dicarboxylate

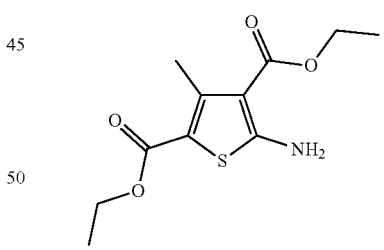

In a 1000 mL single-necked flask, ethyl acetoacetate (50.0 g, 384 mmol), ethyl cyanoacetate (43.4 g, 384 mmol), sulfur element (12.3 g, 384 mmol) were dissolved in anhydrous ethanol (300 mL), and diethylamine (28.1 g, 384 mmol) was slowly added dropwise. After the dropwise addition, the mixture was allowed to react at room temperature overnight. After completion of the reaction, the mixture was filtered, and the filtrate was poured into water (2.4 L). A large amount of yellow solid appeared, which was filtered, and the filtered cakes in the two filtration were washed once with ethanol/water (v/v=1:8), and dried at 40° C. to obtain 69.4 g of the title compound with a yield of 70%. MS (ESI) m/z 258.1 [M+H]$^+$.

Step 2: Preparation of ethyl 5-(3-(1-(tert-butoxycarbonyl)azetidin-3-yl)ureido)-3-methylthiophene-2,4-dicarboxylate

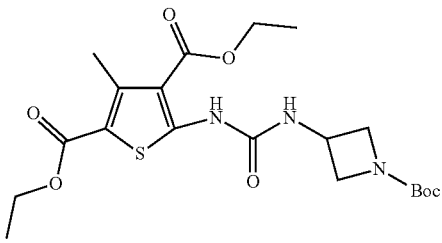 [SMILES: CCOC(=O)c1sc(NC(=O)NC2CN(C(=O)OC(C)(C)C)C2)c(C(=O)OCC)c1C]

In a −5° C. low temperature reaction bath, a solution of diethyl 5-amino-3-methylthiophene-2,4-dicarboxylate (45.0 g, 175 mmol) and triethylamine (70.8 g, 700 mmol) in anhydrous dichloromethane (750 mL) was added dropwise to a solution of triphosgene (51.9 g, 175 mmol) in anhydrous dichloromethane (250 mL). After the dropwise addition, the mixture was stirred at room temperature for 1 h, and then N-t-butoxycarbonyl-3-aminocyclobutylamine (30.1 g, 175 mmol) was added and the mixture was stirred at room temperature overnight. After completion of the reaction, the mixture was concentrated, added with water (600 mL), extracted with ethyl acetate (700 mL×3). The organic layer was dried over anhydrous sodium sulfate, filtered and the filtrate was concentrated and subjected to silica-gel column chromatography (petroleum ether:ethyl acetate=5:1) to obtain 44.8 g of the title compound with a yield of 56%. MS (ESI) m/z 456.2 [M+H]+.

Step 3: Preparation of ethyl 3-(1-(tert-butoxycarbonyl)azetidin-3-yl)-5-methyl-2,4-dioxo-1,2,3,4-tetrahydrothieno[2,3-d]pyrimidine-6-carboxylate

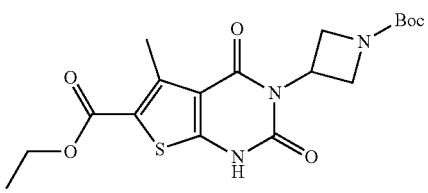 [SMILES: CCOC(=O)c1sc2[nH]c(=O)n(C3CN(C(=O)OC(C)(C)C)C3)c(=O)c2c1C]

In a 1000 mL two-necked flask, ethyl 5-(3-(1-(tert-butoxycarbonyl)azetidin-3-yl)ureido)-3-methylthiophene-2,4-dicarboxylate (28.5 g, 62.5 mmol) was dissolved in anhydrous tetrahydrofuran (430 mL). Under argon protection, sodium hydride (2.25 g, 93.8 mmol) was added, and then the mixture was heated and refluxed at 110° C. for 2 h. After completion of the reaction, the mixture was cooled to room temperature. The reaction was quenched with saturated solution of ammonium chloride (400 mL), and the mixture was extracted with ethyl acetate (400 mL×3). The organic layer was dried over anhydrous sodium sulfate, filtered and the filtrate was concentrated and subjected to silica-gel column chromatography (petroleum ether:ethyl acetate=5:1) to obtain 20.1 g of the title compound with a yield of 78%. MS (ESI) m/z 410.2 [M+H]+.

Step 4: Preparation of 3-(1-(tert-butoxycarbonyl)azetidin-3-yl)-5-methyl-2,4-dioxo-1,2,3,4-tetrahydrothieno[2,3-d]pyrimidine-6-carboxylic Acid

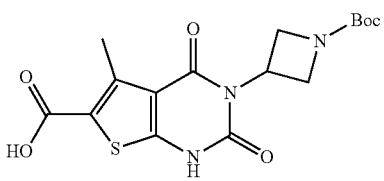 [SMILES: Cc1c(C(=O)O)sc2[nH]c(=O)n(C3CN(C(=O)OC(C)(C)C)C3)c(=O)c12]

In a 1000 mL single-necked flask, ethyl 3-(1-(tert-butoxycarbonyl)azetidin-3-yl)-5-methyl-2,4-dioxo-1,2,3,4-tetrahydrothieno[2,3-d]pyrimidine-6-carboxylate was dissolved in methanol (300 mL), and then aqueous solution of sodium hydroxide (4.0 M, 100 mL) was added. The mixture was stirred at room temperature overnight. After completion of the reaction, the mixture was concentrated to remove most of the methanol. In an ice bath, the mixture was adjusted with concentrated hydrochloric acid to a pH of weak acidity, and extracted with ethyl acetate (150 mL×3). The organic layer was dried over anhydrous sodium sulfate, filtered and the filtrate was concentrated to obtain the title compound, which was directly used in the next step. MS (ESI) m/z 380.1 [M−H]−.

Step 5: Preparation of tert-butyl 3-(5-methyl-2,4-dioxo-1,4-dihydrothieno[2,3-d]pyrimidin-3(2H)-yl)azetidin-1-carboxylate

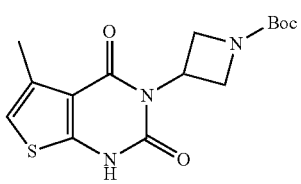 [SMILES: Cc1csc2[nH]c(=O)n(C3CN(C(=O)OC(C)(C)C)C3)c(=O)c12]

In a 500 mL single-necked flask, 3-(1-(tert-butoxycarbonyl)azetidin-3-yl)-5-methyl-2,4-dioxo-1,2,3,4-tetrahydrothieno[2,3-d]pyrimidine-6-carboxylic acid (8.0 g, 21.0 mmol) was dissolved in N-methylpyrrolidone (160 mL), and anhydrous potassium carbonate (3.4 g, 25.2 mmol) and anhydrous silver acetate (4.2 g, 25.2 mmol) were heated at 110° C. for 2 h. After completion of the reaction, the mixture was cooled to room temperature, quenched with water (300 mL), and extracted with ethyl acetate (200 mL×3). The organic layer was washed with water, dried over anhydrous sodium sulfate, filtered and the filtrate was concentrated to obtain the title compound, which was directly used in the next step. MS (ESI) m/z 338.1 [M+H]+.

Step 6: Preparation of tert-butyl 3-(1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)azetidin-1-carboxylate

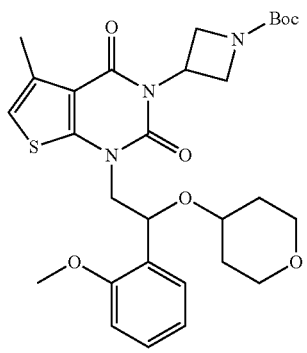 [SMILES: COc1ccccc1C(Cn1c(=O)n(C2CN(C(=O)OC(C)(C)C)C2)c(=O)c2c(C)csc21)OC1CCOCC1]

In a 250 mL two-necked flask, tert-butyl 3-(5-methyl-2,4-dioxo-1,4-dihydrothieno[2,3-d]pyrimidin-3(2H)-yl)azetidin-1-carboxylate (4.0 g, 11.8 mmol) and triphenylphosphine (9.3 g, 35.4 mmol) were added. Under argon protection, the mixture was dissolved in anhydrous tetrahydrofuran (100 mL), and then 2-2-methoxyphenyl)-2-(4-tetrahydropyranyloxy)ethanol (3.0 g, 11.8 mmol) and diisopropyl azodicarboxylate (DIAD) (7.2 g, 35.4 mmol) were added in sequence, and stirred at 40° C. overnight. After completion of the reaction, the mixture was directly subjected to silica-gel column chromatography (petroleum ether:ethyl acetate=5:1) to obtain 1.0 g of the title compound with a yield of 15%. MS (ESI) m/z 572.2 [M+H]⁺.

Step 7: Preparation of tert-butyl 3-(6-bromo-1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)azetidin-1-carboxylate

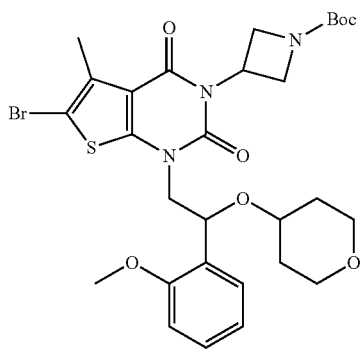 [SMILES: COc1ccccc1C(Cn1c(=O)n(C2CN(C(=O)OC(C)(C)C)C2)c(=O)c2c(C)c(Br)sc21)OC1CCOCC1]

In a 100 mL single-necked flask, tert-butyl 3-(1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)azetidin-1-carboxylate (0.800 g, 1.399 mmol) was dissolved in chloroform (25 mL), followed by addition of N-bromosuccinimide (0.249 g, 1.399 mmol) and azobisisobutyronitrile (0.023 g, 0.140 mmol) in sequence. The mixture was stirred at room temperature for 2 h. After completion of the reaction, the mixture was directly subjected to silica-gel column chromatography (petroleum ether:ethyl acetate=4:1) to obtain 0.692 g of the title compound with a yield of 76%. MS (ESI) m/z 650.2 [M+H]⁺.

Step 8: Preparation of t-butyl3-(1-(2-(2-methoxyphenyl)-2-((tetrahydro-2H-pyran-4-yl)oxy)ethyl)-5-methyl-6-(oxazol-2-yl)2,4-dioxo-1,4-dihydrothieno[2,3-d]pyrimidin-3(2H)-yl)azetidin-1-carboxylate

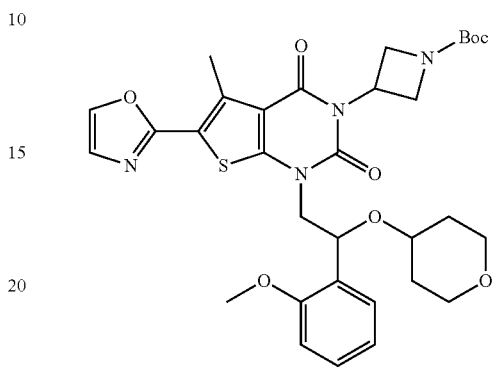

In a 25 mL two-necked flask, tert-butyl 3-(6-bromo-1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)azetidin-1-carboxylate (0.612 g, 0.941 mmol), tris(dibenzylideneacetone)dipalladium (0.086 g, 0.094 mmol) and 2-dicyclohexylphosphino-2,4,6-triisopropylbiphenyl (0.179 g, 0.376 mmol) were added. Under argon protection, anhydrous toluene (9 mL) was added, and then 2-tri-n-butyltinoxazole (0.676 g, 1.881 mmol) was added. The mixture was stirred at 90° C. overnight. After completion of the reaction, the mixture was directly subjected to silica-gel column chromatography (petroleum ether:ethyl acetate=5:1) to obtain 0.246 g of the title compound with a yield of 41%. MS (ESI) m/z 639.2 [M+H]⁺.

Step 9: Preparation of 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione

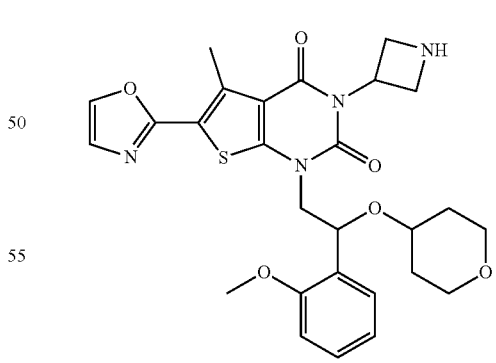

In a 25 mL single-necked flask, t-butyl 3-(1-(2-(2-methoxyphenyl)-2-((tetrahydro-2H-pyran-4-yl)oxy)ethyl)-5-methyl-6-(oxazol-2-yl)2, 4-dioxo-1,4-dihydrothieno[2,3-d]pyrimidin-3(2H)-yl)azetidin-1-carboxylate (0.108 g, 0.169 mmol) was dissolved in toluene (5 mL), and then silica gel (100-200 mesh, 1.08 g) was added. The mixture was refluxed to react for 4 h, and then cooled to room temperature, and suction-filtered. The filtrate was concentrated, and subjected to silica-gel column chromatography (dichloromethane:methanol=30:1) to obtain 0.083 g of the title compound with a yield of 91%. $^1$H NMR (400 MHz, CDCl$_3$) δ 7.70 (s, 1H), 7.62-7.54 (m, 1H), 7.35-7.27 (m, 1H), 7.21 (s, 1H), 7.03 (t, 1H), 6.92-6.84 (m, 1H), 5.44-5.35 (m, 1H), 4.58-4.48 (m, 1H), 4.34-4.24 (m, 1H), 4.16-4.05 (m, 1H), 4.05-3.93 (m, 1H), 3.91 (s, 1H), 3.87 (s, 3H), 3.83-3.81 (m, 1H), 3.81-3.66 (m, 3H), 3.48-3.42 (m, 1H), 3.39-3.28 (m, 2H), 2.86 (d, 3H), 1.78-1.69 (m, 2H), 1.59-1.52 (m, 1H), 1.48-1.37 (m, 1H). MS (ESI) m/z 539.2 [M+H]$^+$.

Example 7: 3-(1-acetylazetidin-3-yl)-1-(2-(2-methoxyphenyl)-2-((tetrahydro-2H-pyran-4)-yl)oxy)ethyl)-5-methyl-6-(oxazol-2-yl)thieno[2,3-d]pyrimidin-2,4(1H,3H)-dione To 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione (0.03 g, 0.056 mmol) obtained in Step 9 of Example 6, dichloromethane (3 mL) and triethylamine (0.2 mL) were added. In an ice bath, acetylchloride (0.006 g, 0.084 mmol) was added dropwise, and the mixture was stirred at room temperature. After completion of the reaction, the reaction was quenched with methanol (1 mL), concentrated and then subjected to silica-gel column chromatography (dichloromethane:methanol=25:1) to obtain 0.018 g of the title compound with a yield of 56%. $^1$H NMR (400 MHz, CDCl$_3$) δ 7.72 (s, 1H), 7.58-7.52 (m, 1H), 7.35-7.28 (m, 1H), 7.23 (s, 1H), 7.03 (t, 1H), 6.87 (dd, 1H), 5.68-5.51 (m, 1H), 5.44-5.37 (m, 1H), 4.65 (dd, 1H), 4.51-4.43 (m, 1H), 4.4-4.27 (m, 2H), 4.19-4.04 (m, 2H), 3.87 (d, 3H), 3.80-3.64 (m, 2H), 3.47-3.38 (m, 1H), 3.37-3.26 (m, 2H), 2.88 (d, 3H), 1.94 (s, 3H), 1.73-1.69 (m, 2H), 1.57-1.48 (m, 2H), 1.40-1.34 (m, 1H). MS (ESI) m/z 581.2 [M+H]$^+$.

Example 8: 3-(1-(cyclopropanecarbonyl)azetidin-3-yl)-1-(2-(2-methoxyphenyl)-2-((tetrahydro-2H-pyran-4-yl)oxy)ethyl)-5-methyl-6-thieno[2,3-d]pyrimidine-2,4(1H,3H)-dione

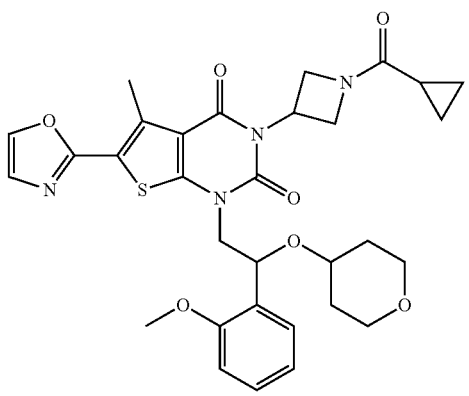 [SMILES: COc1ccccc1C(Cn1c(=O)n(C2CN(C(=O)C3CC3)C2)c(=O)c2c(C)c(-c3ncco3)sc21)OC1CCOCC1]

3-(Azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione (0.150 g, 0.28 mmol) obtained in Step 9 of Example 6 was dissolved in dichloromethane (3 mL), and then trimethylamine (0.057 g, 0.56 mmol) was added. In an ice bath, cyclopropanecarbonyl chloride (0.036 g, 0.34 mmol) was added dropwise. After stirring at room temperature for 1 h, the mixture was heated to reflux for 24 h. The reaction was quenched with methanol (1 mL), and the mixture was concentrated and then subjected to silica-gel column chromatography (petroleum ether:ethyl acetate=1:1 to 1:3) to obtain 0.038 g of the title compound with a yield of 23%. MS (ESI) m/z 607.2 [M+H]$^+$; $^1$H NMR (400 MHz, CDCl$_3$) δ 7.69 (s, 1H), 7.63-7.55 (m, 1H), 7.34-7.28 (m, 1H), 7.23-7.19 (m, 1H), 7.03 (t, 1H), 6.87 (t, 1H), 5.41-5.36 (m, 1H), 4.62-4.56 (m, 1H), 4.50-4.44 (m, 1H), 4.36-4.29 (m, 1H), 4.24-4.13 (m, 2H), 3.98 (dd, 1H), 3.91 (s, 1H), 3.87 (s, 2H), 3.79-3.69 (m, 2H), 3.47-3.41 (m, 1H), 3.38-3.30 (m, 2H), 2.87 (d, 3H), 1.80-1.68 (m, 2H), 1.65-1.59 (m, 1H), 1.47-1.37 (m, 1H), 1.03-0.94 (m, 2H), 0.90-0.81 (m, 2H). MS (ESI) m/z 607.2 [M+H]$^+$.

Example 9: 1-(2-(2-methoxyphenyl)-2-((tetrahydro-2H-pyran-4-yl)oxy)ethyl)-5-methyl-3-(1-(methylsulfonyl)azetidin-3-yl)-6-(oxazol-2-yl)thieno[2,3-d]pyrimidine-2,4(1H,3H)-dione

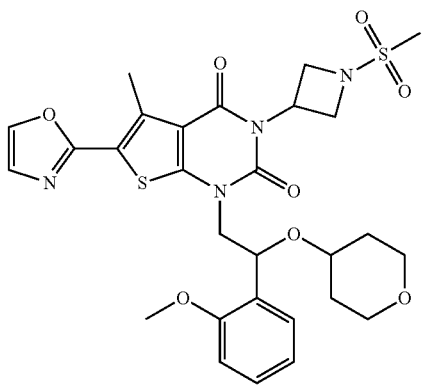 [SMILES: COc1ccccc1C(Cn1c(=O)n(C2CN(S(C)(=O)=O)C2)c(=O)c2c(C)c(-c3ncco3)sc21)OC1CCOCC1]

In a 25 mL single-necked flask, 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione (0.020 g, 0.037 mmol) obtained in Step 9 of Example 6 was dissolved in anhydrous tetrahydrofuran (1 mL), and triethylamine (0.2 mL) was added. In an ice bath, methanesulfonyl chloride (0.006 g, 0.048 mmol) was added dropwise, and the mixture was stirred at room temperature. After completion of the reaction, the reaction was quenched with methanol (2 mL), and the mixture was directly subjected to silica-gel column chromatography (dichloromethane:methanol=20:1) to obtain 0.010 g of the title compound with a yield of 43%. $^1$H NMR (400 MHz, CDCl$_3$) δ 7.70 (s, 1H), 7.61-7.55 (m, 1H), 7.34-7.28 (m, 1H), 7.22 (s, 1H), 7.03 (t, 1H), 6.92-6.84 (m, 1H), 5.41-5.34 (m, 1H), 4.75-4.58 (m, 2H), 4.43 (dd, 1H), 4.35-4.22 (m, 1H), 4.20-3.96 (m, 3H), 3.89 (d, 3H), 3.81-3.67 (m, 2H), 3.49-3.39 (m, 1H), 3.38-3.28 (m, 2H), 3.05 (d, 3H), 2.87 (d, 3H), 1.77-1.70 (m, 2H), 1.57-1.52 (m, 1H), 1.44-1.38 (m, 1H). MS (ESI) m/z 617.2 [M+H]$^+$.

Example 10: 3-(1-(ethyl sulfonyl)azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H, 3H)-dione

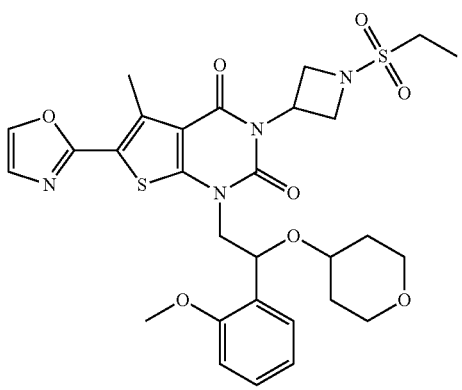 [SMILES: CCS(=O)(=O)N1CC(n2c(=O)c3c(C)c(-c4ncco4)sc3n(CC(OC3CCOCC3)c3ccccc3OC)c2=O)C1]

In a 25 mL single-necked flask, 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H, 3H)-dione (0.100 g, 0.186 mmol) obtained in Step 9 of Example 6 was dissolved in anhydrous tetrahydrofuran (5 mL), and triethylamine (0.2 mL) was added. In an ice bath, ethanesulfonyl chloride (0.031 g, 0.241 mmol) was added dropwise, and the mixture was stirred at room temperature. After completion of the reaction, the reaction was quenched with methanol (5 mL), and the mixture was directly subjected to silica-gel column chromatography (dichloromethane:methanol=50:1) to obtain 0.067 g of the title compound with a yield of 57%. $^1$H NMR (400 MHz, CDCl$_3$) δ 7.70 (d, 1H), 7.60-7.55 (m, 1H), 7.34-7.29 (m, 1H), 7.22 (d, 1H), 7.03 (t, 1H), 6.89 (t, 1H), 5.42-5.33 (m, 1H), 4.77-4.59 (m, 2H), 4.41 (dd, 1H), 4.34-4.22 (m, 1H), 4.18-4.04 (m, 2H), 4.02-3.93 (m, 1H), 3.89 (d, 3H), 3.81-3.67 (m, 2H), 3.49-3.40 (m, 1H), 3.38-3.28 (m, 2H), 3.22-3.11 (m, 2H), 2.87 (d, 3H), 1.74-1.69 (m, 2H), 1.58-1.53 (m, 1H), 1.47-1.42 (m, 1H), 1.39 (t, 3H). MS (ESI) m/z 631.2 [M+H]$^+$.

Example 11: 3-(1-benzoylazetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione

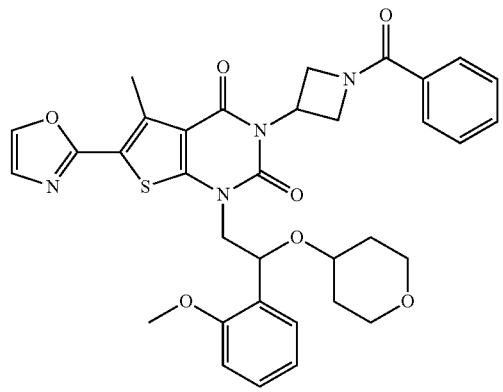 [SMILES: COc1ccccc1C(Cn1c(=O)n(C2CN(C(=O)c3ccccc3)C2)c(=O)c2c(C)c(-c3ncco3)sc21)OC1CCOCC1]

In a 25 mL single-necked flask, 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H, 3H)-dione (0.100 g, 0.186 mmol) obtained in Step 9 of Example 6 was dissolved in anhydrous tetrahydrofuran (6 mL), and triethylamine (0.7 mL) was added. In an ice bath, benzoyl chloride (0.034 g, 0.241 mmol) was added dropwise, and the mixture was heated and stirred at 60° C. for 5 h. After completion of the reaction, the reaction was quenched with methanol (6 mL), and the mixture was subjected to silica-gel column chromatography (dichloromethane:methanol=40:1) to obtain 0.066 g of the title compound with a yield of 56%. $^1$H NMR (400 MHz, CDCl$_3$) δ 7.98 (d, 2H), 7.70 (s, 1H), 7.58-7.51 (m, 2H), 7.43-7.36 (m, 2H), 7.33-7.27 (m, 1H), 7.24-7.20 (m, 1H), 7.04-6.96 (m, 1H), 6.90-6.81 (m, 1H), 5.40-5.32 (m, 1H), 4.78-4.68 (m, 2H), 4.55-4.43 (m, 1H), 4.32-4.22 (m, 1H), 4.20-3.97 (m, 3H), 3.86 (d, 3H), 3.76-3.67 (m, 1H), 3.62-3.53 (m, 1H), 3.43-3.33 (m, 1H), 3.32-3.15 (m, 2H), 2.89 (d, 3H), 1.68-1.62 (m, 2H), 1.53-1.48 (m, 1H), 1.41-1.34 (m, 1H). MS (ESI) m/z 643.2 [M+H]$^+$.

Example 12: 1-(2-(2-methoxyphenyl)-2-((tetrahydro-2H-pyran-4-yl)oxy)ethyl)-5-methyl-3-(1-(morpholine-4-formyl)azetidin-3-yl)-6-(oxazol-2-yl)thieno[2,3-d]pyrimidine-2,4(1H,3H)-dione

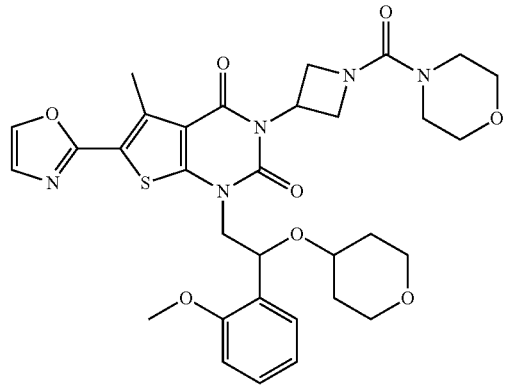 [SMILES: COc1ccccc1C(Cn1c(=O)n(C2CN(C(=O)N3CCOCC3)C2)c(=O)c2c(C)c(-c3ncco3)sc21)OC1CCOCC1]

A solution of 3-(azetidin-3-yl)-1-(2-(2-methoxyphenyl)-2-((tetrahydro-2H-pyran-4-yl) oxy)ethyl)-5-methyl-6-(oxazol-2-yl)thieno[2,3-d]pyrimidine-2,4(1H,3H)-dione (0.104 g, 0.193 mmol) obtained in Step 9 of Example 6 and trimethylamine (0.078 g, 0.772 mmol) in anhydrous dichloromethane (2 mL) was added dropwise to a solution of triphosgene (0.058 g, 0.193 mmol) in anhydrous dichloromethane (1 mL) which was cooled with −5° C. low temperature reaction bath. After the addition, the mixture was continued to be stirred at −5° C. for 2 h. Morpholine (0.034 g, 0.386 mmol) was added. After the addition, the mixture was stirred at room temperature overnight. The mixture was directly subjected to silica-gel column chromatography (ethyl acetate) to obtain 0.060 g of the title compound with a yield of 48%. MS (ESI) m/z 652.2 [M+H]$^+$; $^1$H NMR (400 MHz, CDCl$_3$) δ 7.71 (dd, 1H), 7.62-7.55 (m, 1H), 7.35-7.28 (m, 1H), 7.25-7.22 (m, 1H), 7.05 (t, 1H), 6.90 (t, 1H), 5.43-5.33 (m, 1H), 4.70-4.60 (m, 1H), 4.59-4.48 (m, 1H), 4.35-4.24 (m, 1H), 4.24-4.07 (m, 2H), 4.05-3.96 (dd, 1H), 3.91 (d, 3H), 3.83-3.68 (m, 3H), 3.68-3.54 (m, 4H), 3.54-3.40 (m, 4H), 3.40-3.25 (m, 3H), 2.86 (d, 3H), 1.80-1.68 (m, 2H), 1.57-1.49 (m, 1H), 1.43-1.36 (m, 1H). MS (ESI) m/z 652.2 [M+H]$^+$.

Example 13: 1-(2-(2-methoxyphenyl)-2-((tetrahydro-2H-pyran-4-yl)oxy)ethyl)-5-methyl-6-(oxazol-2-yl)-3-(1-pyridineformylazetidin-3-yl)thieno[2,3-d]pyrimidine-2,4(1H,3H)-dione

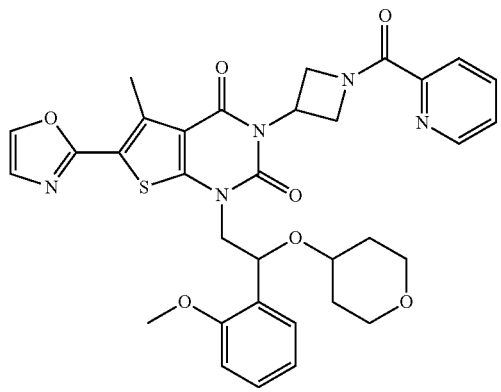 [SMILES: COc1ccccc1C(Cn1c(=O)n(C2CN(C(=O)c3ccccn3)C2)c(=O)c2c(C)c(-c3ncco3)sc21)OC1CCOCC1]

In a 25 mL single-necked flask, 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione (0.100 g, 0.186 mmol) obtained in Step 9 of Example 6 was dissolved in anhydrous tetrahydrofuran (5 mL), and triethylamine (0.7 mL) was added. In an ice bath, pyridine-2-formyl chloride hydrochloride (0.040 g, 0.223 mmol) was added, and the mixture was heated and stirred at 70° C. for 2 h. After completion of the reaction, the reaction was quenched with methanol (5 mL), and the mixture was subjected to silica-gel column chromatography (dichloromethane:methanol=50:1) to obtain 0.024 g of the title compound with a yield of 20%. $^1$H NMR (400 MHz, CDCl$_3$) δ 8.75 (d, 1H), 8.04 (d, 1H), 7.80 (t, 1H), 7.69 (s, 1H), 7.56 (t, 1H), 7.50-7.40 (m, 1H), 7.33-7.27 (m, 1H), 7.22 (s, 1H), 7.06-6.96 (m, 1H), 6.92-6.80 (m, 1H), 5.41-5.33 (m, 1H), 4.85-4.71 (m, 2H), 4.70-4.57 (m, 1H), 4.33-4.21 (m, 1H), 4.18-4.05 (m, 2H), 4.01-3.89 (m, 1H), 3.86 (d, 3H), 3.77-3.68 (m, 1H), 3.67-3.54 (m, 1H), 3.45-3.36 (m, 1H), 3.35-3.16 (m, 2H), 2.86 (s, 3H), 1.73-1.65 (m, 2H), 1.57-1.47 (m, 1H), 1.42-1.33 (m, 1H). MS (ESI) m/z 644.2 [M+H]$^+$.

Example 14: 3-(1-(1H-imidazol-2-carbonyl)azetidin-3-yl)-1-(2-(2-methoxyphenyl)-2-((tetrahydro)-2H-pyran-4-yl)oxy)ethyl)-5-methyl-6-(oxazol-2-yl)thieno[2,3-d]pyrimidine-2,4(1H,3H)-dione

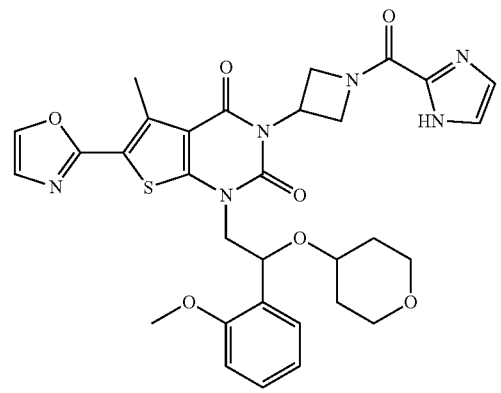 [SMILES: COc1ccccc1C(Cn1c(=O)n(C2CN(C(=O)c3ncc[nH]3)C2)c(=O)c2c(C)c(-c3ncco3)sc21)OC1CCOCC1]

In a 25 mL single-necked flask, 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione obtained in Step 9 of Example 6 (0.080 g, 0.148 mmol) was dissolved in anhydrous N,N-dimethylformamide (6 mL), followed by addition of imidazole-2-carboxylic acid (0.025 g, 0.223 mmol), N,N-diisopropylethylamine (0.8 mL), bromo-tris-pyrrolidino-phosphonium hexafluorophosphate (0.104 g, 0.223 mmol) and 4-dimethylaminopyridine (0.006 g, 0.044 mmol) in sequence. The mixture was stirred at room temperature for 3 h, and then stirred at 80° C. overnight. After completion of the reaction, water (20 mL) was added, and the mixture was extracted with ethyl acetate (30 mL×3). The organic layer was dried over anhydrous sodium sulfate, filtered and the filtrate was concentrated and subjected to silica-gel column chromatography (dichloromethane:methanol=40:1) to obtain 0.030 g of the title compound with a yield of 32%. $^1$H NMR (400 MHz, CDCl$_3$) δ 11.55 (s, 1H), 7.73-7.68 (m, 1H), 7.62-7.55 (m, 1H), 7.37-7.31 (m, 1H), 7.31-7.28 (m, 1H), 7.23-7.20 (m, 1H), 7.15 (s, 1H), 7.08-7.02 (m, 1H), 6.95-6.87 (m, 1H), 5.49-5.32 (m, 1H), 5.05 (dd, 1H), 4.86-4.69 (m, 1H), 4.67-4.53 (m, 1H), 4.54-4.38 (m, 1H), 4.29-4.19 (m, 1H), 4.11-4.00 (m, 1H), 3.97 (s, 2H), 3.90 (s, 1H), 3.89-3.83 (m, 1H), 3.81-3.63 (m, 2H), 3.48-3.40 (m, 1H), 3.39-3.22 (m, 2H), 2.85 (d, 3H), 1.69-1.60 (m, 2H), 1.58-1.49 (m, 1H), 1.45-1.36 (m, 1H). MS (ESI) m/z 633.2 [M+H]$^+$.

Example 15: 1-(3-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3 (4H)-yl)azetidine-1-carbonyl)-3-methylazetidine-3-carboxylic Acid

Step 2: Preparation of 1-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)azetidine-1-carbonyl)-3-methylazetidin-3-carboxylic Acid

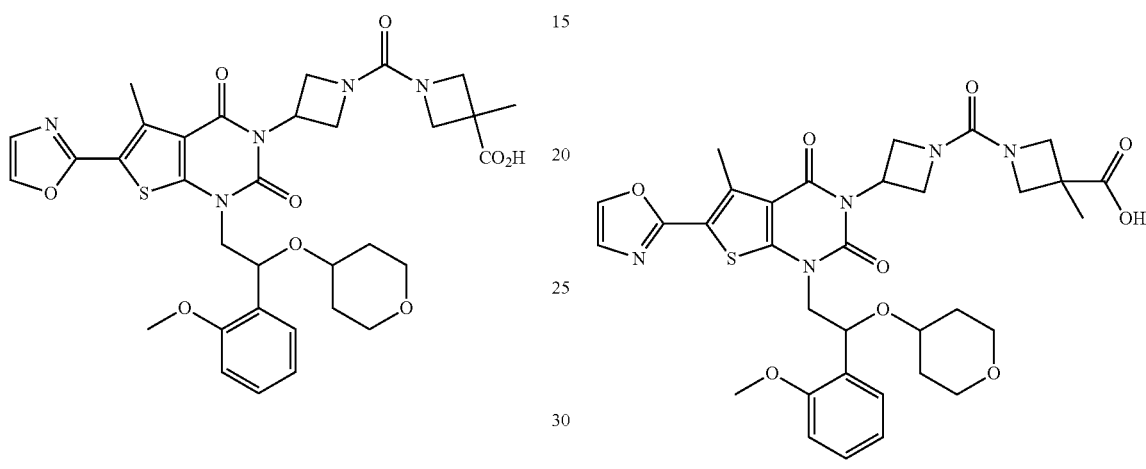

Step 1: Preparation of methyl 1-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)azetidine-1-carbonyl)-3-methylazetidine-3-carboxylate In a −5° C. bath, a solution of 3-(azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione (0.150 g, 0.278 mmol) obtained in Step 9 of Example 6 and triethylamine (0.169 g, 1.67 mmol) in anhydrous dichloromethane (5 mL) was added dropwise to a solution of triphosgene (0.083 g, 0.278 mmol) in anhydrous dichloromethane (5 mL). After the dropwise addition, the mixture was stirred at 0° C. for 1 h, and then methyl 3-methylazetidine-3-carboxylate hydrochloride (0.093 g, 0.557 mmol) was added and the mixture was stirred at room temperature overnight. After completion of the reaction, the mixture was concentrated, mixed with water (15 mL), and then extracted with ethyl acetate (15 mL×3). The organic layer was dried over anhydrous sodium sulfate and filtered, and the filtrate was concentrated and subjected to silica-gel column chromatography (petroleum ether:ethyl acetate=1:2) to obtain 0.060 g of the title compound with a yield of 31%. MS (ESI) m/z 694.3 [M+H]$^+$.

In a 25 mL single-necked flask, methyl 1-(3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)azetidine-1-carbonyl)-3-methylazetidine-3-carboxylate (0.060 g, 0.086 mmol) was dissolved in methanol (2 mL), and sodium hydroxide solution (1.0 M, 2 mL) was added. The reaction was carried out at room temperature for 1 h. After completion of the reaction, the mixture was adjusted with diluted hydrochloric acid (2 M) to a weak acidity, and extracted with ethyl acetate (10 mL×3). The organic layers were combined and washed twice with saturated aqueous solution of sodium chloride. The organic layer was dried over anhydrous sodium sulfate and filtered, and the filtrate was concentrated and separated by preparative chromatography to obtain 0.020 g of the title compound with a yield of 34%. $^1$H NMR (400 MHz, CDCl$_3$) δ 7.70 (s, 1H), 7.56 (d, 1H), 7.34-7.28 (m, 1H), 7.21 (s, 1H), 7.03 (t, 1H), 6.89 (t, 1H), 5.48-5.34 (m, 1H), 4.65-4.46 (m, 2H), 4.34-4.12 (m, 4H), 4.09-3.96 (m, 2H), 3.89 (d, 3H), 3.81-3.47 (m, 5H), 3.44-3.26 (m, 3H), 2.82 (s, 3H), 1.80-1.67 (m, 2H), 1.57-1.47 (m, 3H), 1.40-1.32 (m, 1H), 1.31-1.20 (m, 1H). MS (ESI) m/z 678.2 [M−H]$^−$.

Example 16: 3-(1-(3-Hydroxy-3-methylazetidin-1-oyl)azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H,3H)-dione

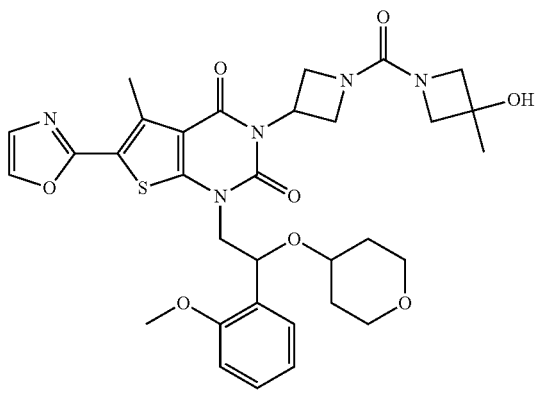 [SMILES: COc1ccccc1C(Cn1c(=O)n(C2CN(C(=O)N3CC(C)(O)C3)C2)c(=O)c2c(C)c(-c3ncco3)sc21)OC1CCOCC1]

Triphosgene (0.055 g, 0.186 mmol) was dissolved in anhydrous dichloromethane (3 mL) and stirred at −5° C. 3-(Azetidin-3-yl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H, 3H)-dione (0.100 g, 0.186 mmol) obtained in Step 9 of Example 6 and triethylamine (0.113 g, 1.116 mmol) were dissolved in anhydrous dichloromethane (5 mL). The mixture was slowly added dropwise to the above solution of triphosgene in dichloromethane at −5° C. After the dropwise addition, the mixture was stirred at 0° C. for 1.5 h, and then transferred to room temperature. 3-Methyl-3-azetidinol (0.025 g, 0.204 mmol) was added and the reaction was carried out overnight. The mixture was concentrated and subjected to silica-gel column chromatography (ethyl acetate) to obtain 0.012 g of the title compound with a yield of 10%. $^1$H NMR (400 MHz, CDCl$_3$) δ 7.70 (s, 1H), 7.60-7.50 (m, 1H), 7.36-7.28 (m, 1H), 7.22 (d, 1H), 7.04 (d, 1H), 6.92 (d, 1H), 5.49 (s, 1H), 4.67-4.56 (m, 1H), 4.54-4.35 (m, 1H), 4.23-4.15 (m, 1H), 4.13-3.99 (m, 2H), 3.95 (s, 2H), 3.90 (s, 3H), 3.87-3.61 (m, 5H), 3.57-3.17 (m, 4H), 2.88 (d, 3H), 1.92-1.68 (m, 2H), 1.53-1.47 (m, 1H), 1.46-1.43 (m, 1H), 1.43 (s, 3H). MS (ESI) m/z 652.1 [M+H]$^+$.

Example 17: 2-(1-(2-(2-methoxyphenyl)-2-(piperidin-4-yloxy)ethyl)-5-methyl-6-(oxazole-2)-yl)-2,4-dioxo-1,4-dihydrothieno[2,3-d]pyrimidin-3(2H)-yl)-2-methylpropionic Acid

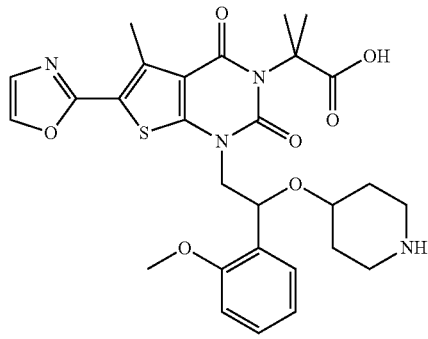 [SMILES: COc1ccccc1C(Cn1c(=O)n(C(C)(C)C(=O)O)c(=O)c2c(C)c(-c3ncco3)sc21)OC1CCNCC1]

Step 1: preparation of tert-butyl 4-(2-hydroxy-1-(2-methoxyphenyl)ethoxy)piperidine-1-carboxylate

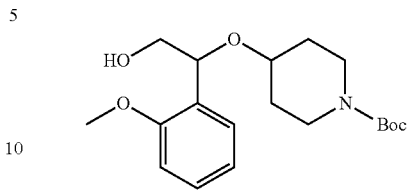

Tert-butyl 4-hydroxypiperidine-1-carboxylate (2.01 mg, 9.99 mmol) and tris(trifluoromethanesulfonate)aluminum (0.158 g, 0.333 mmol) were added into a 100 mL round bottom flask. The reaction system was dehydrated and protected by nitrogen. Anhydrous tetrahydrofuran (20 mL) was added, and the reaction temperature was reduced to 0° C. 2-(2-Methoxyphenyl)oxirane (1.50 g, 10.0 mmol) was added to the reaction system, and the system was allowed to warm up to room temperature and stirred overnight. After completion of the reaction, a saturated aqueous solution of sodium chloride was added to the mixture and the mixture was extracted with ethyl acetate. The organic layers were combined and dried over anhydrous sodium sulfate, and then concentrated and purified by column chromatography to obtain 0.45 g of the title compound. LC-MS m/z [M+H]$^+$=352.

Step 2: Preparation of ethyl 2-(3-(1-(tert-butoxy)-2-methyl-1-oxopropan-2-yl)ureido)-4-methylthiophene-3-carboxylate

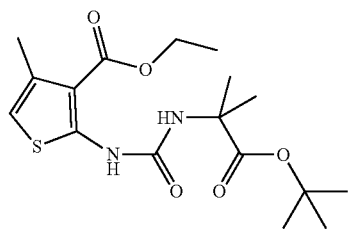 [SMILES: CCOC(=O)c1c(C)csc1NC(=O)NC(C)(C)C(=O)OC(C)(C)C]

Ethyl 2-amino-4-methylthiophene-3-carboxylate (10 g, 54 mmol) and anhydrous dichloromethane (100 mL) were added to a 500 mL round bottom flask, and at 0° C., a solution of triphosgene (5.288 g, 17.8 mmol) in dichloromethane (100 mL) was added dropwise, and the reaction was carried out at 0° C. for 1 h. Triethylamine (21.816 g, 216 mmol) was then slowly added dropwise, and the reaction was continued at 0° C. for 3 h. Then 2-tert-butyl 2-aminoisobutyrate hydrochloride (12.636 g, 64.8 mmol) was added and the mixture was allowed to warm up to room temperature and react overnight. After completion of the reaction, the mixture was washed with saturated aqueous solution of sodium chloride and the solvent was evaporated. The residue was recrystallized with dichloromethane and petroleum ether to obtain 12 g of the title compound. LC-MS m/z [M+H]$^+$=371.

Step 3: Preparation of tert-butyl 2-methyl-2-(5-methyl-2,4-dioxo-1,4-dihydrothieno[2,3-d]pyrimidin-3(2H)-yl)propionate

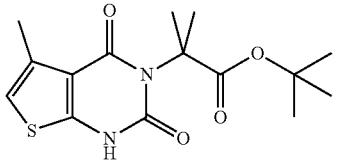 [SMILES: Cc1csc2[nH]c(=O)n(C(C)(C)C(=O)OC(C)(C)C)c(=O)c12]

Sodium (7.45 g, 324 mmol) was slowly added to absolute ethanol (200 mL). After solid sodium was completely dissolved, ethyl 2-(3-(1-(tert-butoxy)-2-methyl-1-oxopropan-2-yl)ureido)-4-methylthiophene-3-carboxylate (12 g, 32.4 mmol) was added. The mixture was then warmed up to reflux for 1 h. After completion of the reaction, the mixture was neutralized with glacial acetic acid to a neutral pH. A large amount of solid was precipitated, and filtered under reduced pressure. The filtrate was concentrated and purified by column chromatography to obtain 3.1 g of the title compound. LC-MS m/z [M+H]$^+$=325.

Step 4: Preparation of tert-butyl 4-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate

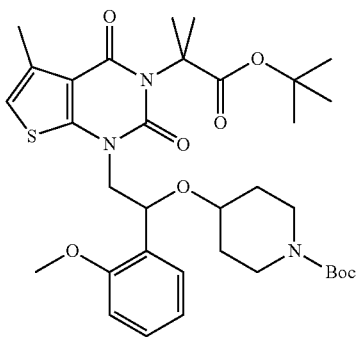 [SMILES: COc1ccccc1C(Cn1c(=O)n(C(C)(C)C(=O)OC(C)(C)C)c(=O)c2c(C)csc21)OC1CCN(C(=O)OC(C)(C)C)CC1]

Triphenylphosphine (4.06 g, 15.5 mmol) was added into a 500 mL two-necked flask and protected with argon. At 0° C., anhydrous tetrahydrofuran (100 mL) was added, and diisopropyl azodicarboxylate (DIAD) (3.13 g, 15.5 mmol) was slowly added dropwise. The reaction was carried out at 0° C. for 1 h, followed by addition of tert-butyl 2-methyl-2-(5-methyl-2,4-dioxo-1,4-dihydrothieno[2,3-d]pyrimidin-3(2H)-yl)propionate (1.0 g, 3.1 mmol) and tert-butyl 4-(2-hydroxy-1-(2-methoxyphenyl)ethoxy)piperidine-1-carboxylate (1.31 g, 3.7 mmol). The mixture was warmed up to room temperature and reacted overnight. After completion of the reaction, a saturated aqueous solution of sodium chloride was added and the mixture was extracted with ethyl acetate. The organic phases were combined and washed with a saturated aqueous solution of sodium chloride. The organic phase was dried over anhydrous sodium sulfate, and concentrated and subjected to silica-gel column chromatography to obtain 1.38 g of the title compound. LC-MS m/z [M+H]$^+$=658.

Step 5: Preparation of tert-butyl 4-(2-(6-bromo-3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate

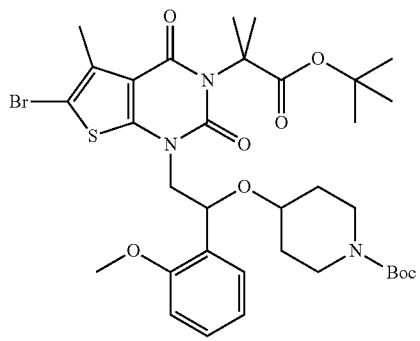 [SMILES: COc1ccccc1C(Cn1c(=O)n(C(C)(C)C(=O)OC(C)(C)C)c(=O)c2c(C)c(Br)sc21)OC1CCN(C(=O)OC(C)(C)C)CC1]

Tert-butyl 4-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate (1.38 g, 2.09 mmol) was added to dichloromethane (15 mL), and N-bromosuccinimide (373 mg, 2.09 mmol) was added at −10° C. The reaction was carried out at −10° C. for 0.5 h and quenched with a saturated aqueous solution of sodium chloride. The mixture was extracted with dichloromethane, and the organic phase was dried over anhydrous sodium sulfate and concentrated to obtain 1.41 g of the title compound. LC-MS m/z [M+H]$^+$=736.

Step 6: Preparation of tert-butyl 4-(2-(3-(1-tert-butoxy)-2-methyl-1-oxopropan-2-yl)-5-methyl-6-(oxazol-2-yl)-2,4-dioxo-3,4-dihydrothieno[2,3-d]pyrimidin-1(2H)-yl)-1-(2-methoxyphenyl)ethoxy)piperidine-1-carboxylate

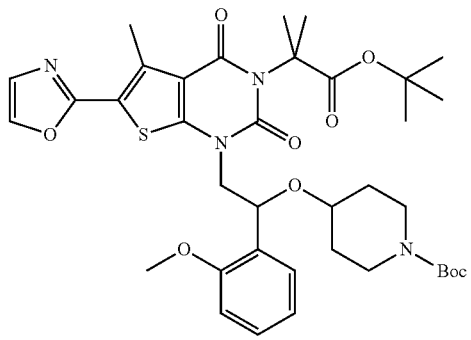 [SMILES: COc1ccccc1C(Cn1c(=O)n(C(C)(C)C(=O)OC(C)(C)C)c(=O)c2c(C)c(-c3ncco3)sc21)OC1CCN(C(=O)OC(C)(C)C)CC1]

Tert-butyl 4-(2-(6-bromo-3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate (642 mg, 0.873 mmol), 2-(tributylstannyl)oxazole (1.250 g, 3.492 mmol), tris(dibenzylideneacetone)dipalladium (80 mg, 0.0873 mmol) and 2-bicyclohexylphosphorus-2,4,6-triisopropylbiphenyl (125 mg, 0.2619 mmol) were added to toluene (20 mL). The reaction was carried out at 110° C. overnight under argon protection. The mixture was cooled to room temperature, concentrated and purified by column chromatography to obtain 356 mg of the title compound. LC-MS m/z [M+H]$^+$=725.

Step 7: Preparation of 2-(1-(2-(2-methoxyphenyl)-2-(piperidin-4-yloxy)ethyl)-5-methyl-6-(oxazole-2-yl)-4-dioxo-1,4-dihydrothiophene[2,3-d]pyrimidin-3(2H)-yl)-2-methylpropionic Acid

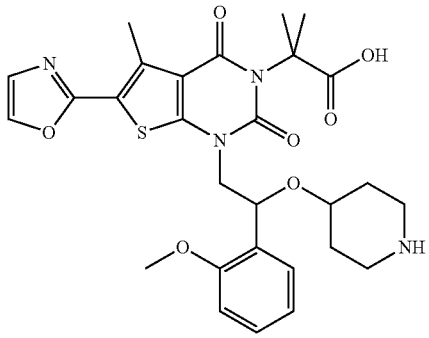 [SMILES: COc1ccccc1C(Cn1c(=O)n(C(C)(C)C(=O)O)c(=O)c2c(C)c(-c3ncco3)sc21)OC1CCNCC1]

Tert-butyl 4-(2-(3-(1-tert-butoxy)-2-methyl-1-oxopropan-2-yl)-5-methyl-6-(oxazol-2-yl)-2,4-dioxo-3,4-dihydrothieno[2,3-d]pyrimidin-1(2H)-yl)-1-(2-methoxyphenyl)ethoxy)piperidine-1-carboxylate (250 mg, 0.345 mmol) was dissolved in tetrahydrofuran (10 mL). Concentrated hydrochloric acid (2 mL) was added and the mixture was reacted at 50° C. overnight. After completion of the reaction, the mixture was cooled to room temperature, extracted with dichloromethane. The organic phase was dried over anhydrous sodium sulfate, concentrated and purified by column chromatography to obtain 5 mg of the title compound. $^1$H NMR (400 MHz, DMSO-d$_6$) δ 13.23 (s, 1H), δ 7.74 (s, 1H), 7.58 (d, 1H), 7.34 (d, 1H), 7.26 (s, 2H), 7.09-7.05 (m, 1H), 5.35-5.33 (m, 1H), 4.94-4.88 (m, 1H), 4.07 (s, 3H), 3.83-3.70 (m, 3H), 3.40-3.24 (m, 4H), 2.96 (s, 3H), 2.24-1.92 (m, 4H), 1.55-1.40 (m, 6H). LC-MS m/z [M+H]$^+$=569.

Example 18: 2-(1-(2-(2-methoxyphenyl)-2-(piperidin-1-yl)ethyl)-5-methyl-6-(oxazol-2-yl)-2,4-dioxo-1,4-dihydrothieno[2,3-d]pyrimidin-3(2H)-yl)-2-methylpropionic Acid

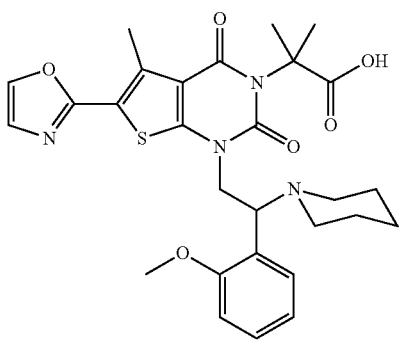 [SMILES: COc1ccccc1C(Cn1c(=O)n(C(C)(C)C(=O)O)c(=O)c2c(C)c(-c3ncco3)sc21)N1CCCCC1]

Step 1: Preparation of 2-(2-methoxyphenyl)-2-(piperidin-1-yl)ethanol

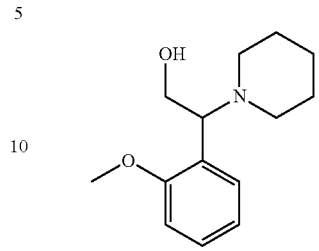

Piperidine (2.55 g, 30.0 mmol) was added to anhydrous dichloromethane (30 mL) and the mixture was cooled to 0° C. 2-(2-Methoxyphenyl)oxirane (1.50 g, 6.0 mmol) was added to the mixture and the reaction was carried out at room temperature for 4 h. After completion of the reaction, a saturated aqueous solution of sodium chloride was added to the reaction mixture. The mixture was extracted with ethyl acetate. The organic phases were combined, dried over anhydrous sodium sulfate, concentrated and purified by column chromatography to obtain 1.0 g of the title compound. LC-MS m/z [M+H]$^+$=236.

Step 2: Preparation of tert-butyl 2-(1-(2-(2-methoxyphenyl)-2-(piperidin-1-yl)ethyl)-5-methyl-2,4-dioxo-1,4-dihydrothieno[2,3-d] pyrimidin-3(2H)-yl)-2-methylpropanoate

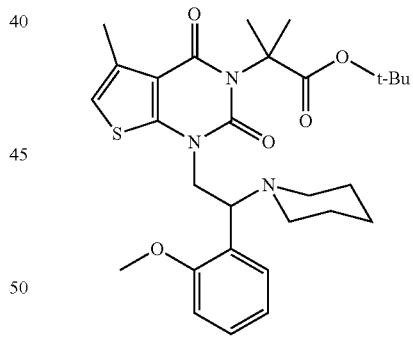

The preparation method was the same as that of tert-butyl 4-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate in Step 4 of Example 17, except that the starting material tert-butyl 4-(2-hydroxy-1-(2-methoxyphenyl) ethoxy) piperidine-1-carboxylate was replaced with 2-(2-methoxyphenyl)-2-(piperidin-1-yl)ethanol as obtained in Step 1 of Example 18, to obtain 1.26 g of the title compound. LC-MS m/z [M+H]$^+$=542.

Step 3: Preparation of tert-butyl 2-(6-bromo-1-(2-(2-methoxyphenyl)-2-(piperidin-1-yl)ethyl)-5-methyl-2,4-dioxo-1,4-dihydrothieno[2,3-d]pyrimidin-3(2H)-yl)-2-methylpropanoate

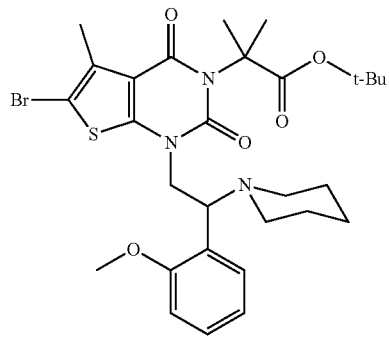 [SMILES: COc1ccccc1C(Cn1c(=O)n(C(C)(C)C(=O)OC(C)(C)C)c(=O)c2c(C)c(Br)sc21)N1CCCCC1]

Tert-butyl 2-(1-(2-(2-methoxyphenyl)-2-(piperidin-1-yl)ethyl)-5-methyl-2,4-dioxo-1,4-dihydrothieno[2,3-d]]pyrimidin-3(2H)-yl)-2-methylpropanoate (1.26 g, 2.326 mmol) was added to dichloromethane (80 mL) and the mixture was cooled to −10° C. N-Bromosuccinimide (413 mg, 2.326 mmol) was added to the mixture and the reaction was carried out for 0.5 h. After completion of the reaction, the reaction was quenched with a saturated aqueous solution of sodium chloride. The mixture was extracted with dichloromethane. The organic phase was dried over anhydrous sodium sulfate, concentrated and purified by column chromatography to obtain 438 mg of the title compound. LC-MS m/z [M+H]⁺=620.

Step 4: Preparation of 2-(1-(2-(2-methoxyphenyl)-2-(piperidin-1-yl)ethyl)-5-methyl-6-(oxazol-2-yl)-2,4-dioxo-1,4-dihydrothieno[2,3-d]pyrimidin-3(2H)-yl)-2-methylpropionic Acid

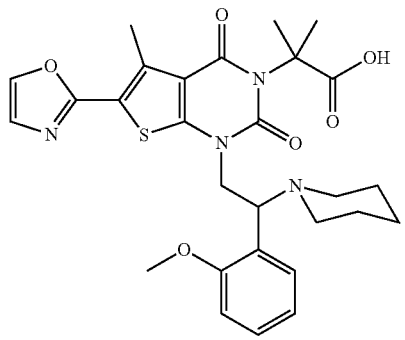 [SMILES: COc1ccccc1C(Cn1c(=O)n(C(C)(C)C(=O)O)c(=O)c2c(C)c(-c3ncco3)sc21)N1CCCCC1]

The preparation method was the same as that of 2-(1-(2-(2-methoxyphenyl)-2-(piperidin-4-yloxy)ethyl)-5-methyl-6-(oxazole-2-yl)-4-dioxo-1,4-dihydrothiophene[2,3-d]pyrimidin-3(2H)-yl)-2-methylpropionic acid in steps 6-7 of Example 17, expect that the starting material tert-butyl 4-(2-(6-bromo-3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate was replaced with tert-butyl 2-(6-bromo-1-(2-(2-methoxyphenyl)-2-(piperidin-1-yl)ethyl)-5-methyl-2,4-dioxo-1,4-dihydrothieno[2,3-d]pyrimidin-3(2H)-yl)-2-methylpropanoate as prepared in Step 3 of Example 18, to obtain 136 mg of the title compound. ¹H NMR (400 MHz, DMSO-d₆) δ 12.41 (s, 1H), 8.17 (s, 1H), 7.58 (brs, 1H), 7.39-7.32 (m, 2H), 7.02 (brs, 2H), 6.23-5.91 (m, 1H), 3.71 (s, 3H), 3.14-2.99 (m, 2H), 2.70 (s, 3H), 2.60 (brs, 1H), 2.33-2.29 (m, 2H), 1.70 (s, 6H), 1.40-1.23 (m, 7H). LC-MS m/z [M+H]⁺=553.

Example 19: 2-(1-(2-(2-methoxyphenyl)-2-((1-methylpiperidin-4-yl)oxy)ethyl)-5-methyl-6-(oxazol-2-yl)-2,4-dioxo-1,4-dihydrothieno[2,3-d]pyrimidin-3(2H)-yl)-2-methylpropionic Acid

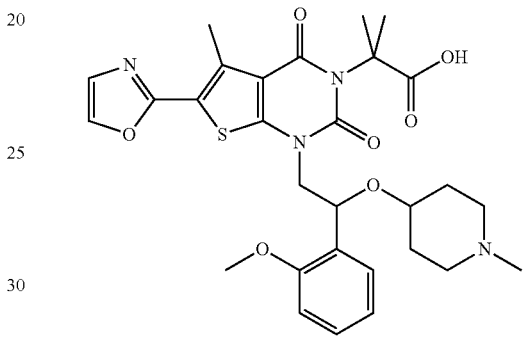

Step 1: Preparation of tert-butyl 2-(1-(2-(2-methoxyphenyl)-2-(piperidin-4-yloxy) ethyl)-5-methyl-6-(oxazole-2-yl)-2,4-dioxo-1,4-dihydrothieno[2,3-d]pyrimidin-3(2H)-yl)-2-methylpropanoate

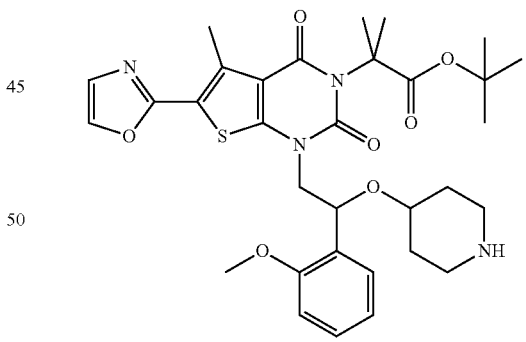

The preparation method was the same as that of 2-(1-(2-(2-methoxyphenyl)-2-(piperidin-4-yloxy)ethyl)-5-methyl-6-(oxazole-2-yl)-4-dioxo-1,4-dihydrothiophene[2,3-d]pyrimidin-3(2H)-yl)-2-methylpropionic acid in steps 1-7 of Example 17, expect that the reaction temperature of Example 17 was room temperature instead of 50° C., to obtain the title compound, which was used directly in the next step without purification. LC-MS m/z [M+H]⁺=625.

Step 2: Preparation of tert-butyl 2-(1-(2-(2-methoxyphenyl)-2-((1-methylpiperidin-4-yl) oxy) ethyl)-5-methyl-6-(oxazol-2-yl)-2,4-dioxo-1,4-dihydrothieno[2,3-d]pyrimidin-3(2H)-yl)-2-methylpropanoate

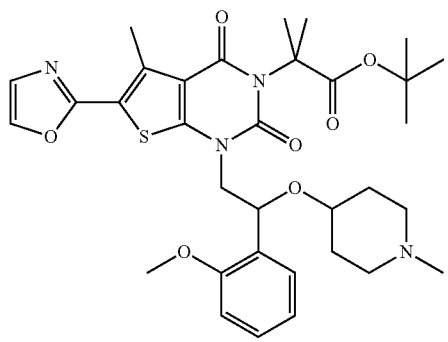 [SMILES: COc1ccccc1C(Cn1c(=O)n(C(C)(C)C(=O)OC(C)(C)C)c(=O)c2c(C)c(-c3ncco3)sc21)OC1CCN(C)CC1]

Tert-butyl 2-(1-(2-(2-methoxyphenyl)-2-(piperidin-4-yloxy)ethyl)-5-methyl-6-(oxazole-2-yl)-2,4-dioxo-1,4-dihydrothieno[2,3-d]pyrimidin-3(2H)-yl)-2-methylpropanoate (150 mg, 0.24 mmol) was dissolved in dichloromethane, and a solution of anhydrous zinc chloride in tetrahydrofuran (0.96 mL, 0.48 mmol, 0.5 M) and paraformaldehyde (43 mg, 0.48 mmol) were added. The mixture was reacted at room temperature for 1 h, and then cooled to 0° C., followed by addition of sodium borohydride (18 mg, 0.48 mmol). The reaction was carried out at room temperature overnight. After completion of the reaction, the mixture was adjusted to a pH of 8-9, extracted with ethyl acetate, dried over anhydrous sodium sulfate, and concentrated. The product was directly used in the next step without purification. LC-MS m/z [M+H]$^+$=639.

Step 3: Preparation of 2-(1-(2-(2-methoxyphenyl)-2-((1-methylpiperidin-4-yl)oxy)ethyl)-5-methyl-6-(oxazol-2-yl)-2,4-dioxo-1,4-dihydrothieno[2,3-d]pyrimidin-3(2H)-yl)-2-methylpropionic Acid

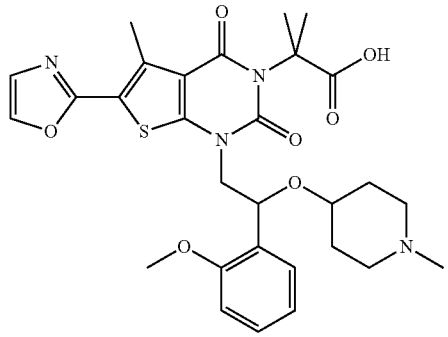 [SMILES: COc1ccccc1C(Cn1c(=O)n(C(C)(C)C(=O)O)c(=O)c2c(C)c(-c3ncco3)sc21)OC1CCN(C)CC1]

Tert-butyl 2-(1-(2-(2-methoxyphenyl)-2-((1-methylpiperidin-4-yl)oxy)ethyl)-5-methyl-6-(oxazol-2-yl)-2,4-dioxo-1,4-dihydrothieno[2,3-d]pyrimidin-3(2H)-yl)-2-methylpropanoate (110 mg, 0.172 mmol) was added to tetrahydrofuran (10 mL), and concentrated hydrochloric acid (2 mL) was added to the solution. The reaction was carried out at 50° C. overnight. After cooling to room temperature, the mixture was extracted with dichloromethane. The organic phase was dried over anhydrous sodium sulfate, concentrated and purified by column chromatography to obtain 10 mg of the title compound. $^1$H NMR (400 MHz, DMSO-d$_6$) δ 12.46 (s, 1H), δ 7.71 (s, 1H), 7.49 (s, 1H), 7.20 (s, 1H), 7.04 (s, 1H), 6.95-6.92 (m, 2H), 5.36-5.34 (m, 1H), 4.13-4.04 (m, 1H), 3.92 (s, 3H), 3.55-3.51 (m, 2H), 3.41-3.25 (m, 4H), 2.94 (s, 3H), 2.25 (s, 3H), 2.11-1.92 (m, 4H), 1.60-1.55 (m, 6H). LC-MS m/z [M+H]$^+$=583.

Example 20: 2-(1-(2-((1-acetylpiperidin-4-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropionic Acid

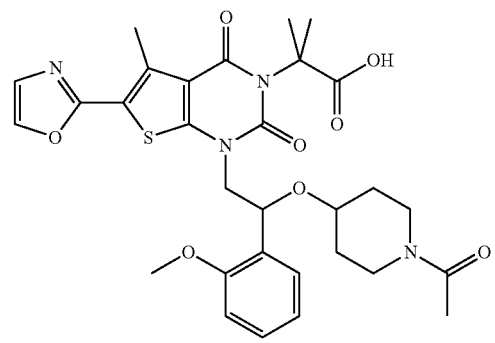 [SMILES: COc1ccccc1C(Cn1c(=O)n(C(C)(C)C(=O)O)c(=O)c2c(C)c(-c3ncco3)sc21)OC1CCN(C(C)=O)CC1]

Step 1: Preparation of tert-butyl 2-(1-(2-(2-methoxyphenyl)-2-(piperidin-4-yloxy)ethyl)-5-methyl-2,4-dioxo-1,4-dihydrothieno[2,3-d]pyrimidin-3(2H)-yl)-2-methylpropanoate

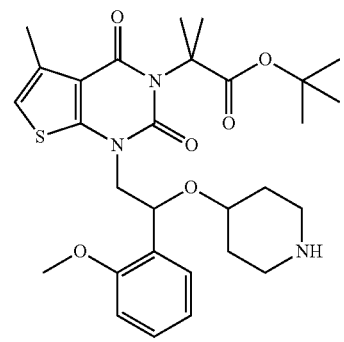 [SMILES: COc1ccccc1C(Cn1c(=O)n(C(C)(C)C(=O)OC(C)(C)C)c(=O)c2c(C)csc21)OC1CCNCC1]

Tert-butyl 4-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate prepared in Step 4 of Example 17 (1.38 g, 2.09 mmol) was added to tetrahydrofuran (20 mL), and concentrated hydrochloric acid (2 mL) was added. The mixture was stirred at room temperature overnight. The mixture was neutralized with NaOH to be alkaline (pH 8~9), and extracted with ethyl acetate. The organic phase was dried over anhydrous sodium sulfate, and concentrated to obtain 798 mg of the title compound, which was directly used in the next step without purification. LC-MS m/z [M+H]$^+$=558.

Step 2: Preparation of tert-butyl 2-(1-(2-((1-acetylpiperidin-4-yl)oxy)-2-(2-methoxyphenyl)ethyl)-5-methyl-2,4-dioxo-1,4-dihydrothieno[2,3-d]pyrimidin-3(2H)-yl)-2-methylpropanoate

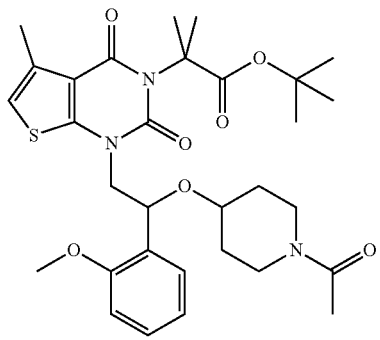 [SMILES: COc1ccccc1C(Cn1c(=O)n(C(C)(C)C(=O)OC(C)(C)C)c(=O)c2c(C)csc21)OC1CCN(C(C)=O)CC1]

Tert-butyl 2-(1-(2-(2-methoxyphenyl)-2-(piperidin-4-yloxy)ethyl)-5-methyl-2,4-dioxo-1,4-dihydrothieno[2,3-d]pyrimidin-3(2H)-yl)-2-methylpropanoate (798 mg, 1.43 mmol) was dissolved in dichloromethane and triethylamine (289.4 mg, 2.86 mmol) was added. Acetyl chloride (134.71 mg, 1.72 mmol) was added dropwise at 0° C. and the mixture was allowed to react overnight at room temperature. After completion of the reaction, the mixture was adjusted to a pH of 8-9, extracted with ethyl acetate, dried over anhydrous sodium sulfate, and concentrated to obtain the title compound, which was directly used in the next step without purification. LC-MS m/z [M+H]$^+$=600.

Step 3: Preparation of 2-(1-(2-((1-acetylpiperidin-4-yl)oxy)-2-(methoxyphenyl)ethyl)-5-methyl-6-(oxazol-2-yl)-2,4-dioxo-1,4-dihydrothieno[2,3-d]pyrimidin-3(2H)-yl)-2-methylpropionic Acid

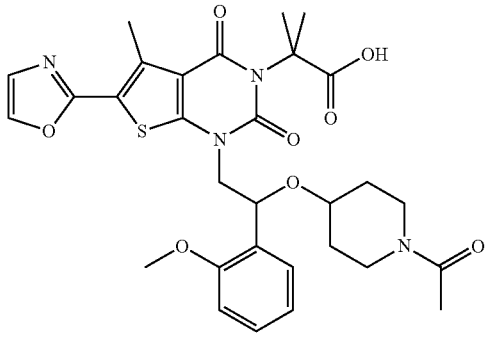 [SMILES: COc1ccccc1C(Cn1c(=O)n(C(C)(C)C(=O)O)c(=O)c2c(C)c(-c3ncco3)sc21)OC1CCN(C(C)=O)CC1]

The preparation method was the same as that of 2-(1-(2-(2-methoxyphenyl)-2-(piperidin-4-yloxy)ethyl)-5-methyl-6-(oxazole-2-yl)-4-dioxo-1,4-dihydrothiophene[2,3-d]pyrimidin-3(2H)-yl)-2-methylpropionic acid in steps 5-7 of Example 17, expect that the starting material tert-butyl 4-(2-(3-(1-tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate was replaced with tert-butyl 2-(1-(2-((1-acetylpiperidin-4-yl)oxy)-2-(2-methoxyphenyl)ethyl)-5-methyl-2,4-dioxo-1,4-dihydrothieno[2,3-d]pyrimidin-3(2H)-yl)-2-methylpropanoate as prepared in Step 2 of Example 20, to obtain 222 mg of the title compound. $^1$H NMR (400 MHz, CDCl$_3$) δ 12.43 (s, 1H), δ 8.24 (s, 1H), 7.50 (d, 1H), 7.40 (s, 1H), 7.35-7.31 (m, 1H), 7.07-7.01 (m, 2H), 5.30-5.28 (m, 1H), 4.06-4.01 (m, 1H), 3.83 (s, 3H), 3.41-3.39 (m, 3H), 3.20-3.16 (m, 1H), 2.75 (s, 3H), 1.96-1.99 (m, 1H), 1.89 (brs, 2H), 1.67 (d, 6H), 1.54-1.60 (m, 3H), 1.28-1.24 (m, 3H). LC-MS m/z [M+H]$^+$=611.

Example 21: 2-(1-(2-((1-(cyclopropanoylpiperidin-4-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropionic Acid

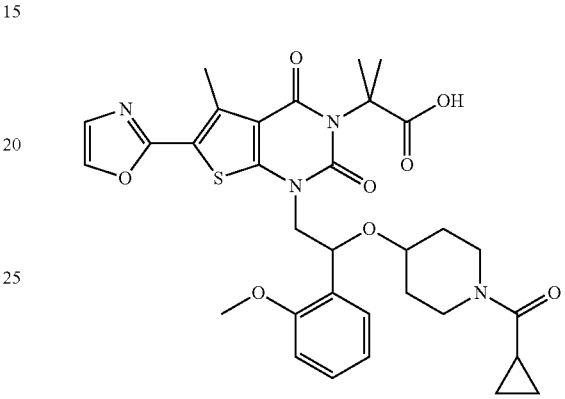

Step 1: Preparation of tert-butyl 2-(1-(2-((1-(cyclopropanoyl)piperidin-4-yl)oxy)-2-(2-methoxyphenyl)ethyl)-5-methyl-2,4-dioxo-1,4-dihydrothieno[2,3-d]pyrimidin-3(2H)-yl)-2-methylpropanoate

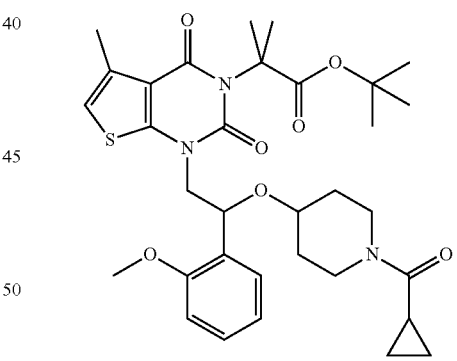

Tert-butyl 2-(1-(2-(2-methoxyphenyl)-2-(piperidin-4-yloxy)ethyl)-5-methyl-2,4-dioxo-1,4-dihydrothieno[2,3-d]pyrimidin-3(2H)-yl)-2-methylpropanoate prepared in Step 1 of Example 20 (1.76 g, 3.2 mmol) was dissolved in dichloromethane, and triethylamine (647 mg, 6.4 mmol) was added. Cyclopropylcarbonyl chloride (401 mg, 3.84 mmol) was added dropwise at 0° C. and the reaction was carried out at room temperature overnight. After completion of the reaction, the mixture was adjusted to a pH of 8-9, extracted with ethyl acetate, dried over anhydrous sodium sulfate, and concentrated to obtain the title compound, which was directly used in the next step without purification. LC-MS m/z [M+H]$^+$=626.

Step 2: Preparation of 2-(1-(2-((1-(cyclopropionylpiperidin-4-yl)oxy)-2-(2-methoxyphenyl)ethyl)-5-methyl-6-(oxazol-2-yl)-2,4-dioxo-1,2-dihydrothieno[2,3-d]pyrimidin-3(4H)-yl)-2-methylpropionic Acid

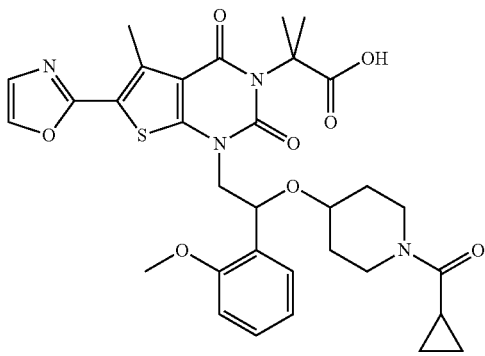 [SMILES: COc1ccccc1C(Cn1c(=O)n(C(C)(C)C(=O)O)c(=O)c2c(C)c(-c3ncco3)sc21)OC1CCN(C(=O)C2CC2)CC1]

The preparation method was the same as that of 2-(1-(2-(2-methoxyphenyl)-2-(piperidin-4-yloxy)ethyl)-5-methyl-6-(oxazole-2-yl)-4-dioxo-1,4-dihydrothiophene[2,3-d]pyrimidin-3(2H)-yl)-2-methylpropionic acid in steps 5-7 of Example 17, expect that the starting material tert-butyl 4-(2-(3-(1-tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate was replaced with tert-butyl 2-(1-(2-((1-(cyclopropanoyl)piperidin-4-yl) oxy)-2-(2-methoxyphenyl)ethyl)-5-methyl-2,4-dioxo-1,4-dihydrothieno[2,3-d]pyrimidin-3(2H)-yl)-2-methylpropanoate as prepared in Step 1 of Example 21, to obtain 25 mg of the title compound.
$^1$H NMR (400 MHz, CDCl$_3$) δ 12.42 (s, 1H), δ 8.24 (s, 1H), 7.50 (d, J=6.4, 1H), 7.39 (s, 1H), 7.34-7.30 (m, 1H), 7.06-7.01 (m, 2H), 5.31-5.28 (m, 1H), 4.08-3.99 (m, 1H), 3.82 (s, 3H), 3.59-3.51 (m, 2H), 3.44-3.41 (m, 2H), 3.20-3.16 (m, 2H), 2.75 (s, 3H), 1.85 (brs, 3H), 1.67 (d, J=11.68 Hz, 6H), 1.60-1.54 (m, 3H), 1.31-1.24 (m, 3H). LC-MS m/z [M+H]$^+$=637.

Example 22: 2-(1-(2-(2-methoxyphenyl)-2-((1-methyl sulfonyl)piperidin-4-yl) oxy)ethyl)-5-methyl-6-(oxazol-2-yl)-2,4-dioxo-1,4-dihydrothieno[2,3-d]pyrimidin-3(2H)-yl)-2-methylpropionic Acid

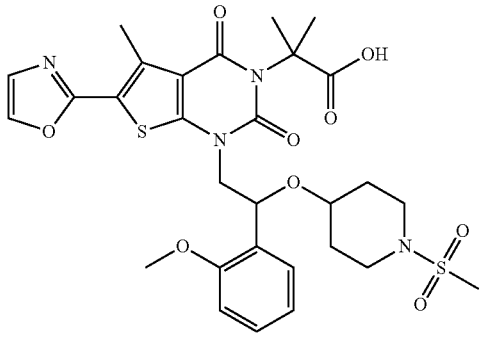 [SMILES: COc1ccccc1C(Cn1c(=O)n(C(C)(C)C(=O)O)c(=O)c2c(C)c(-c3ncco3)sc21)OC1CCN(S(C)(=O)=O)CC1]

Step 1: Preparation of tert-butyl 2-(1-(2-(2-methoxyphenyl)-2-((1-methylsulfonyl) piperidin-4-yl)oxy)ethyl)-5-methyl-6-(oxazol-2-yl)-2,4-dioxo-1,4-dihydrothieno[2,3-d]pyrimidin-3(2H)-yl)-2-methylpropanoate

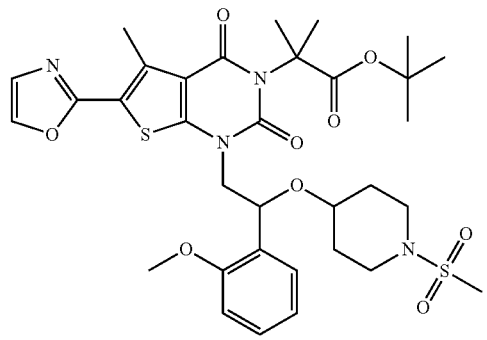 [SMILES: COc1ccccc1C(Cn1c(=O)n(C(C)(C)C(=O)OC(C)(C)C)c(=O)c2c(C)c(-c3ncco3)sc21)OC1CCN(S(C)(=O)=O)CC1]

Tert-butyl 2-(1-(2-(2-methoxyphenyl)-2-(piperidin-4-yloxy)ethyl)-5-methyl-6-(oxazole-2-yl)-2,4-dioxo-1,4-dihydrothieno[2,3-d]pyrimidin-3(2H)-yl)-2-methylpropanoate prepared in Step 1 of Example 19 (150 mg, 0.24 mmol) was dissolved in dichloromethane, and triethylamine (49 mg, 0.48 mmol) was added. The mixture was cooled to 0° C. and methylsulfonyl chloride (41 mg, 0.36 mmol) was added. The reaction was carried out at room temperature overnight. After completion of the reaction, the mixture was adjusted to a pH of 8-9, extracted with ethyl acetate, dried over anhydrous sodium sulfate, and concentrated to obtain the title compound, which was directly used in the next step without purification. LC-MS m/z [M+H]$^+$=703.

Step 2: Preparation of 2-(1-(2-(2-methoxyphenyl)-2-((1-methyl sulfonyl)piperidin-4-yl) oxy)ethyl)-5-methyl-6-(oxazol-2-yl)-2,4-dioxo-1,4-dihydrothieno[2,3-d]pyrimidin-3(2H)-yl)-2-methylpropionic Acid

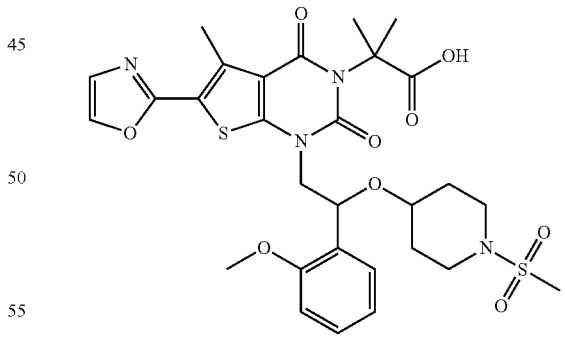

Tert-butyl 2-(1-(2-(2-methoxyphenyl)-2-((1-methylsulfonyl)piperidin-4-yl)oxy)ethyl)-5-methyl-6-(oxazol-2-yl)-2,4-dioxo-1,4-dihydrothieno[2,3-d]pyrimidin-3(2H)-yl)-2-methylpropanoate (75 mg, 0.117 mmol) was added to tetrahydrofuran (10 mL), and then concentrated hydrochloric acid (2 mL) was added. The reaction was carried out at 50° C. overnight. After cooling to room temperature, the mixture was extracted with dichloromethane, dried over anhydrous sodium sulfate, concentrated and purified by column chromatography to obtain 6.2 mg of the title compound. ¹H NMR (400 MHz, CDCl₃) δ 12.52 (s, 1H), δ 8.25 (s, 1H), 7.50 (d, 1H), 7.40 (s, 1H), 7.36-7.32 (m, 1H), 7.08-7.03 (m, 2H), 5.29-5.26 (m, 1H), 4.22 (brs, 1H), 3.82 (s, 3H), 3.34 (brs, 3H), 3.18-3.16 (m, 1H), 3.03-3.00 (m, 2H), 2.84 (brs, 1H), 2.73 (s, 3H), 2.55-2.57 (m, 3H), 1.68 (d, 6H), 1.55-1.59 (m, 3H). LC-MS m/z [M+H]⁺=647.

Example 23: 2-(1-2-((1-acetylazetidin-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropionic Acid

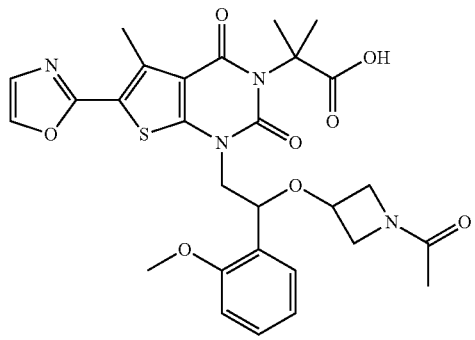 [SMILES: COc1ccccc1C(Cn1c(=O)n(C(C)(C)C(=O)O)c(=O)c2c(C)c(-c3ncco3)sc21)OC1CN(C(C)=O)C1]

Step 1: Preparation of tert-butyl 3-hydroxyazetidine-1-propanoate

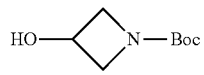

Tert-butyl 3-oxoazetidine-1-carboxylate (3.41 g, 20 mmol) was added to anhydrous methanol (30 mL), and the mixture was cooled to 0° C. Sodium borohydride (1.51 g, 40 mmol) was added, and the reaction was carried out at 0° C. for 1 h. After completion of the reaction, it was quenched with a saturated aqueous solution of sodium chloride. The mixture was extracted with ethyl acetate. The organic phase was dried over anhydrous sodium sulfate, and concentrated to obtain 3.4 g of the title compound.

Step 2: Preparation of tert-butyl 3-(2-hydroxy-1-(2-methoxyphenyl) ethoxy)azetidin-1-carboxylate

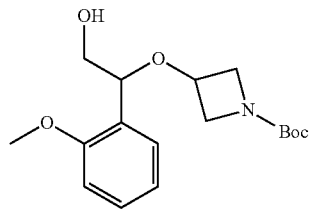 [SMILES: COc1ccccc1C(CO)OC1CN(C(=O)OC(C)(C)C)C1]

Tert-butyl 3-hydroxyazetidine-1-propanoate (2.08 g, 12.0 mmol), aluminum tris(trifluoromethanesulfonate)aluminum (0.711 g, 1.50 mmol) were added into a 100 mL round bottom flask. The reaction system was dehydrated and protected by nitrogen. Anhydrous tetrahydrofuran (40 mL) was added, and the reaction temperature was cooled to 0° C. 2-(2-Methoxyphenyl)oxirane (1.50 g, 10.0 mmol) was added, and the system was allowed to warm to room temperature and stirred overnight. After completion of the reaction, a saturated aqueous solution of sodium chloride was added to the mixture and the mixture was extracted with ethyl acetate. The organic layers were combined and dried over anhydrous sodium sulfate, and then concentrated and purified by column chromatography to obtain 2 g of the title compound. LC-MS m/z [M+H]⁺=324.

Step 3: Preparation of tert-butyl 3-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)azetidin-1-carboxylate

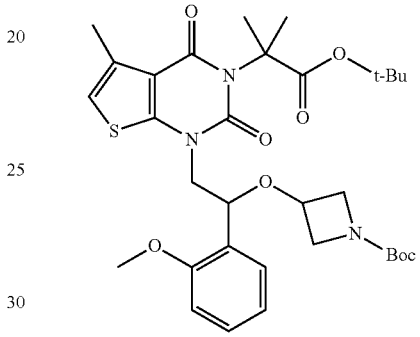

The preparation method was the same as that of tert-butyl 4-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)piperidine-1-carboxylate in Step 4 of Example 17, expect that the starting material tert-butyl 4-(2-hydroxy-1-(2-methoxyphenyl) ethoxy)piperidine-1-carboxylate was replaced with tert-butyl 3-(2-hydroxy-1-(2-methoxyphenyl) ethoxy)azetidin-1-carboxylate as prepared in Step 2 of Example 23, to obtain 0.8 g of the title compound. LC-MS m/z [M+H]⁺=630.

Step 4: Preparation of tert-butyl 2-(1-(2-(azetidin-3-yloxy)-2-(2-methoxyphenyl)ethyl)-5-methyl-2,4-dioxo-1,4-dihydrothieno[2,3-d]pyrimidin-3(2H)-yl)-2-methylpropanoate

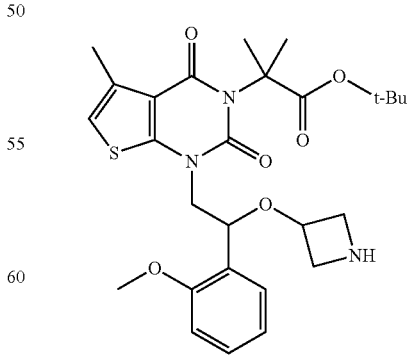

Tert-butyl 3-(2-(3-(1-(tert-butoxy)-2-methyl-1-oxopropan-2-yl)-5-methyl-2,4-dioxo-3,4-dihydrothieno[2,3-d]pyrimidin-1(2H)-yl)-1-(2-methoxyphenyl)ethoxy)azetidin-1- carboxylate (0.8 g, 1.27 mmol) was added to tetrahydrofuran (30 mL), and concentrated hydrochloric acid (2 mL) was added. The mixture was stirred at room temperature overnight. The mixture was neutralized with NaOH to be weak alkaline, and extracted with ethyl acetate. The organic phase was dried over anhydrous sodium sulfate, and concentrated to obtain the title compound. LC-MS m/z [M+H]$^+$=530.

Step 5: Preparation of 2-(1-(2-((1-acetylazetidin-3-yl)oxy)-2-(2-methoxyphenyl) ethyl)-5-methyl-2,4-dioxo-1,4-dihydrothieno[2,3-d]pyrimidin-3(2H)-yl)-2-methylpropionate

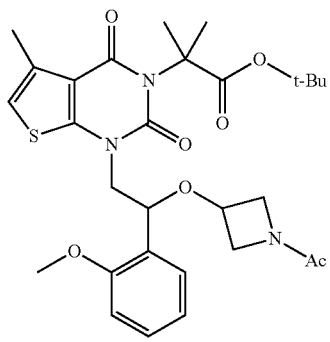 [SMILES: COc1ccccc1C(Cn1c(=O)n(C(C)(C)C(=O)OC(C)(C)C)c(=O)c2c(C)csc21)OC1CN(C(C)=O)C1]

Tert-butyl 2-(1-(2-(azetidin-3-yloxy)-2-(2-methoxyphenyl)ethyl)-5-methyl-2,4-dioxo-1,4-dihydrothieno[2,3-d]pyrimidin-3(2H)-yl)-2-methylpropanoate (0.25 g, 0.473 mmol) was added to anhydrous dichloromethane (40 mL), and triethylamine (96 mg, 0.945 mmol) was added at 0° C., and then acetyl chloride (45 mg, 0.568 mmol) was added. The mixture was slowly warmed up to room temperature and stirred overnight. A saturated aqueous solution of sodium chloride was added and the mixture was extracted with dichloromethane. The organic layer was dried over anhydrous sodium sulfate, concentrated and purified by column chromatography to obtain 130 mg of the title compound. LC-MS m/z [M+H]$^+$=572.

Step 6: Preparation of 2-(1-(2-((1-acetylazetidin-3-yl)oxy)-2-(2-methoxyphenyl)ethyl)-5-methyl-6-(oxazol-2-yl)-2,4-dioxo-1,4-dihydrothieno[2,3-d]pyrimidin-3(2H)-yl)-2-methylpropionic Acid

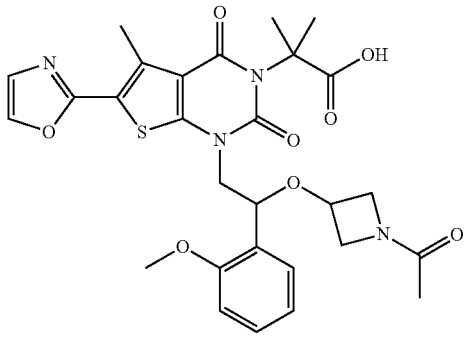 [SMILES: COc1ccccc1C(Cn1c(=O)n(C(C)(C)C(=O)O)c(=O)c2c(C)c(-c3ncco3)sc21)OC1CN(C(C)=O)C1]

The preparation method was the same as that of 2-(1-(2-(2-methoxyphenyl)-2-(piperidin-1-yl)ethyl)-5-methyl-6-(oxazol-2-yl)-2,4-dioxo-1,4-dihydrothieno[2,3-d]pyrimidin-3(2H)-yl)-2-methylpropionic acid in steps 3-4 of Example 18, expect that the starting material tert-butyl 2-(1-(2-(2-methoxyphenyl)-2-(piperidin-1-yl)ethyl)-5-methyl-2,4-dioxo-1,4-dihydrothieno[2,3-d]]pyrimidin-3 (2H)-yl)-2-methylpropanoate was replaced with 2-(1-(2-((1-acetylazetidin-3-yl)oxy)-2-(2-methoxyphenyl)ethyl)-5-methyl-2,4-dioxo-1,4-dihydrothieno[2,3-d]pyrimidin-3 (2H)-yl)-2-methylpropionate as prepared in step 5 of Example 23, to obtain 24.6 mg of the title compound. $^1$H NMR (400 MHz, DMSO-d$_6$) δ 12.43 (s, 1H), 8.23 (s, 1H), 7.42-7.39 (m, 2H), 7.33-7.30 (m, 1H), 7.05-6.98 (m, 2H), 5.11-5.05 (m, 1H), 4.20-4.06 (m, 4H), 3.93-3.76 (m, 4H), 3.48-3.43 (m, 1H), 2.74 (s, 3H), 1.74-1.64 (m, 8H), 1.23 (br, 2H). LC-MS m/z [M+H]$^+$=583.

Example 24

4-(1-(2-(2-methoxyphenyl)-2-((tetrahydro-2H-pyran-4-yl)oxy)ethyl)-5-methyl-6-(oxazol-2-yl)-2, 4-dioxo-1,4-dihydrothieno[2,3-d]pyrimidin-3(2H)-yl) benzoic Acid

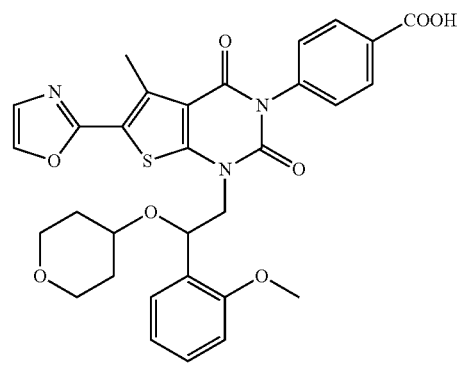 [SMILES: COc1ccccc1C(Cn1c(=O)n(-c2ccc(C(=O)O)cc2)c(=O)c2c(C)c(-c3ncco3)sc21)OC1CCOCC1]

Step 1: Preparation of ethyl 2-(3-(4-(tert-butoxycarbonyl)phenyl)ureido)-4-methylthiophene-3-carboxylate

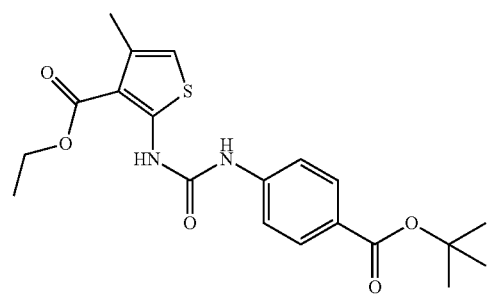 [SMILES: CCOC(=O)c1c(C)csc1NC(=O)Nc1ccc(C(=O)OC(C)(C)C)cc1]

Ethyl 2-amino-4-methylthiophene-3-carboxylate (4.8 g, 25.9 mmol) and triphosgene (3.1 g, 10.36 mmol) were added into a two-necked flask. Under argon protection, dichloromethane (200 mL) was added at −20° C. After the material was dissolved, a solution of triethylamine (10.5 g, 103.6 mmol) in dichloromethane was slowly added dropwise into the reaction mixture and the duration of addition was 1 h. The reaction was continued at 0° C. for 4 h, and then tert-butyl 4-aminobenzoate (5 g, 25.9 mmol) was added. The reaction mixture was stirred at room temperature overnight. Water was added to quench the reaction, and the mixture was layered to separate the organic phase. The aqueous phase was extracted twice with dichloromethane. The organic phases were combined, dried and concentrated, and purified by column chromatography to obtain 7 g of the title compound. LC-MS m/z [M+H]$^+$=405.

Step 2: Preparation of ethyl 4-(5-methyl-2,4-dioxo-1,4-dihydrothieno [2,3-d]pyrimidin-3(2H)-yl)benzoate

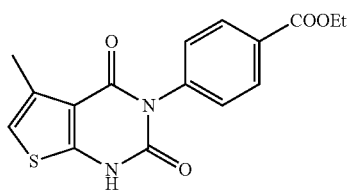 [SMILES: CCOC(=O)c1ccc(-n2c(=O)[nH]c3scc(C)c3c2=O)cc1]

Sodium block (356 mg, 15.5 mmol) was added into a dry two-necked flask and re-distilled anhydrous ethanol was added under argon protection. After completion of the sodium block reaction, ethyl 2-(3-(4-(tert-butoxycarbonyl)phenyl)ureido)-4-methylthiophene-3-carboxylate (2 g, 6.19 mmol) was added and the reaction was carried out at 80° C. for 2 h. After completion of the reaction, ethanol was removed by spinning. The mixture was directly subjected to column chromatography with ethyl acetate to give 1 g of the title compound. LC-MS m/z [M+H]$^+$=331.

Step 3: Preparation of ethyl 4-(1-(2-(2-methoxyphenyl)-2-((tetrahydro-2H-pyran-4-yl) oxy)ethyl)-5-methyl-2,4-dioxo-1,4-dihydrothieno[2,3-d]pyrimidin-3(2H)-yl)benzoate

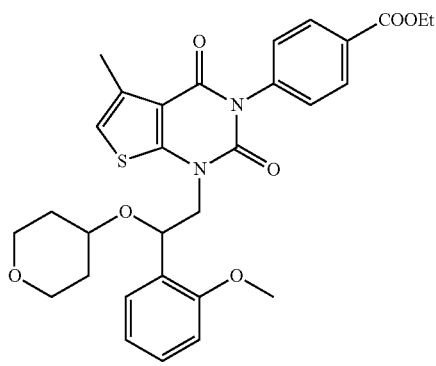 [SMILES: CCOC(=O)c1ccc(-n2c(=O)c3c(C)csc3n(CC(OC3CCOCC3)c3ccccc3OC)c2=O)cc1]

Ethyl 4-(5-methyl-2,4-dioxo-1,4-dihydrothieno[2,3-d]pyrimidin-3(2H)-yl)benzoate (650 mg, 1.97 mmol), (2-methoxyphenyl)-2-((tetrahydro-2H-pyran-4-yl)oxy)ethanol (596 mg, 2.36 mmol), and triphenylphosphine (1.03 g, 3.94 mmol) were dissolved in tetrahydrofuran (10 mL). Under argon protection, a solution of diisopropyl azodicarboxylate in tetrahydrofuran was added dropwise at 0° C., and allowed to react overnight at room temperature. The mixture was washed with water (10 mL), and extracted with ethyl acetate. The organic phase was dried, concentrated and subjected to column chromatography to obtain 200 mg of the title compound. LC-MS m/z [M+H]$^+$=565.

Step 4: Preparation of ethyl 4-(6-bromo-1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)benzoate

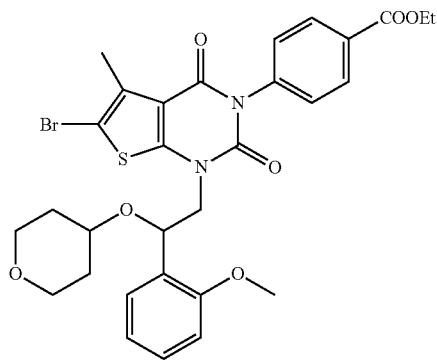 [SMILES: CCOC(=O)c1ccc(-n2c(=O)c3c(C)c(Br)sc3n(CC(OC3CCOCC3)c3ccccc3OC)c2=O)cc1]

Ethyl 4-(1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)benzoate (200 mg, 0.355 mmol) was dissolved in N,N-dimethylformamide (5 mL), and a solution of N-bromosuccinimide in N,N-dimethylformamide was added dropwise at 0° C., and the reaction was carried out at 0° C. for 1 h. The reaction mixture was washed with an equal volume of saturated sodium chloride solution and extracted with ethyl acetate. The organic phase was washed with a saturated solution of sodium chloride, dried, concentrated, and purified by column chromatography to obtain 140 mg of the title compound. LC-MS m/z [M+H]$^+$=643.

Step 5: Preparation of ethyl 4-(1-(2-(2-methoxyphenyl)-2-((tetrahydro-2H-pyran-4-yl) oxy)ethyl)-5-methyl-6-(oxazol-2-yl)-2,4-dioxo-1,4-dihydrothieno[2,3-d]pyrimidin-3(2H)-yl)benzoate

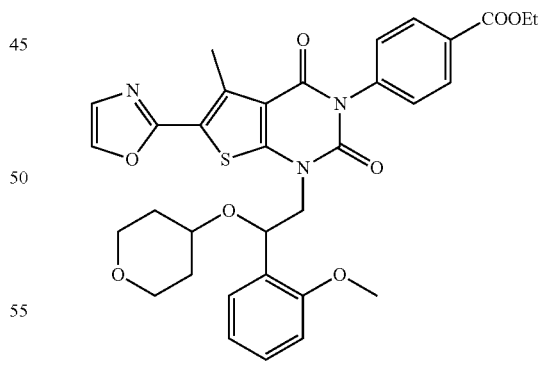

Ethyl 4-(6-bromo-1-(2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)benzoate (140 mg, 0.22 mmol), (tributylstannyl)oxazole (313 mg, 0.87 mmol), tris(dibenzylideneacetone)dipalladium (20 mg, 0.022 mmol) and 2-dicyclohexylphosphino-2,4,6-triisopropylbiphenyl (42 mg, 0.088 mmol) were dissolved in dry toluene (5 mL). Under argon protection, the reaction was carried out overnight. The solvent was removed by spinning and the mixture was worked up by column chromatography to give 100 mg of the title compound. LC-MS m/z [M+H]$^+$=631.

Step 6: Preparation of 4-(1-(2-(2-methoxyphenyl)-2-((tetrahydro-2H-pyran-4-yl) oxy)ethyl)-5-methyl-6-(oxazol-2-yl)-2,4-dioxo-1,4-dihydrothieno[2,3-d]pyrimidin-3(2H)-yl)benzoic Acid

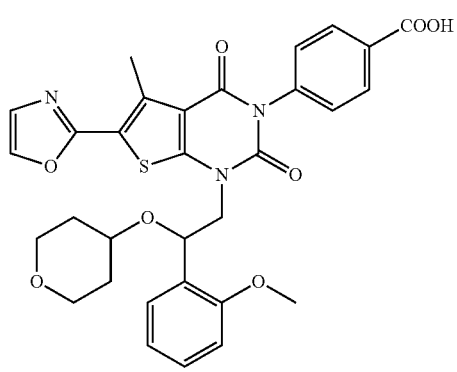 [SMILES: COc1ccccc1C(Cn1c(=O)n(-c2ccc(C(=O)O)cc2)c(=O)c2c(C)c(-c3ncco3)sc21)OC1CCOCC1]

Ethyl 4-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoate (100 mg, 0.158 mmol) was dissolved in a mixed solvent of methanol (15 mL) and water (5 mL), and lithium hydroxide (38 mg, 10 mmol) was added, and the reaction was carried out at room temperature for 24 h. The reaction mixture was acidified with 5% hydrochloric acid to be pH=5-6, extracted with ethyl acetate, dried, concentrated and separated by column chromatography to give 40 mg of the title compound. $^1$H NMR (400 MHz, DMSO-d$_6$) δ 13.00 (s, 1H), 8.26 (s, 1H), 8.08 (d, 2H), 7.51 (d, 1H), 7.42-7.39 (m, 3H), 7.35-7.29 (m, 1H), 7.06-7.01 (m, 2H), 5.34-5.31 (m, 1H), 4.17-4.14 (m, 1H), 4.04-4.02 (m, 1H), 3.80 (s, 3H), 3.60-3.59 (m, 2H), 3.42-3.27 (m, 3H), 2.79 (s, 3H), 1.68-1.65 (m, 2H), 1.30-1.24 (m, 2H). LC-MS m/z [M+H]$^+$=604.

Example 24a: (R)-4-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic Acid

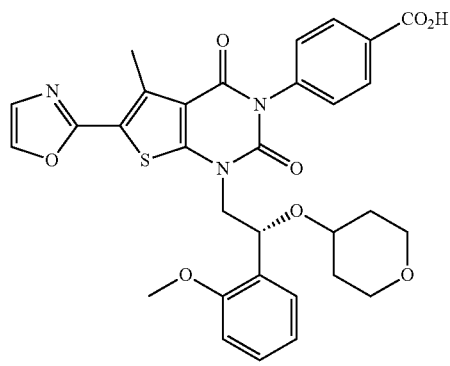 [SMILES: COc1ccccc1[C@H](Cn1c(=O)n(-c2ccc(C(=O)O)cc2)c(=O)c2c(C)c(-c3ncco3)sc21)OC1CCOCC1]

The preparation method was the same as that of Example 24, except that (2-methoxyphenyl)-2-((tetrahydro-2H-pyran-4-yl)oxy)ethanol was replaced with (R)-(2-methoxyphenyl)-2-((tetrahydro-2H-pyran-4-yl)oxy)ethanol, to obtain the title compound. LC-MS m/z [M+H]$^+$=604.

Example 25: Preparation of 3-(1-(2-(2-methoxyphenyl)-2-((tetrahydro-2H-pyran-4-yl) oxy)ethyl)-5-methyl-6-(oxazol-2-yl)-2,4-dioxo-1,4-dihydrothieno[2,3-d]pyrimidin-3(2H)-yl)benzoic Acid

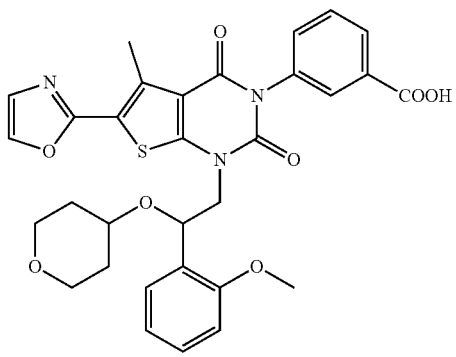 [SMILES: COc1ccccc1C(Cn1c(=O)n(-c2cccc(C(=O)O)c2)c(=O)c2c(C)c(-c3ncco3)sc21)OC1CCOCC1]

Step 1: Preparation of ethyl 2-(3-(3-(tert-butoxycarbonyl)phenyl)ureido)-4-methylthiophene-3-carboxylate

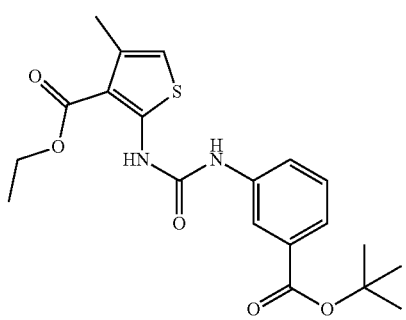 [SMILES: CCOC(=O)c1c(C)csc1NC(=O)Nc1cccc(C(=O)OC(C)(C)C)c1]

The preparation method was the same as that of ethyl 2-(3-(4-(tert-butoxycarbonyl)phenyl)ureido)-4-methylthiophene-3-carboxylate in Step 1 of Example 24, except that the starting material tert-butyl 4-aminobenzoate was replaced with tert-butyl 3-aminobenzoate (5 g, 25.9 mmol) to obtain 8.5 g of the title compound. LC-MS m/z [M+H]$^+$=405.

Step 2: Preparation of 3-(1-(2-(2-methoxyphenyl)-2-((tetrahydro-2H-pyran-4-yl)oxy) ethyl)-5-methyl-6-(oxazol-2-yl)-2,4-dioxo-1,4-dihydrothieno[2,3-d]pyrimidin-3(2H)-yl)benzoic Acid

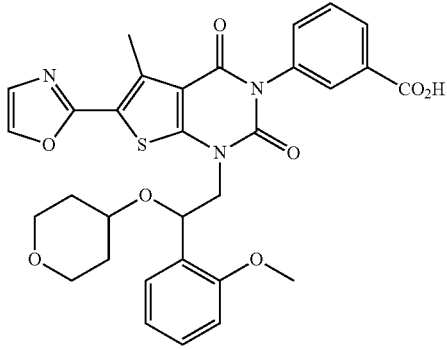 [SMILES: COc1ccccc1C(Cn1c(=O)n(-c2cccc(C(=O)O)c2)c(=O)c2c(C)c(-c3ncco3)sc21)OC1CCOCC1]

The preparation method was the same as that of 4-(1-(2-(2-methoxyphenyl)-2-((tetrahydro-2H-pyran-4-yl)oxy) ethyl)-5-methyl-6-(oxazol-2-yl)-2, 4-dioxo-1,4-dihydrothieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with ethyl 2-(3-(3-(tert-butoxycarbonyl) phenyl)ureido)-4-methylthiophene-3-carboxylate as prepared in Step 1 of Example 25 to obtain 200 mg of the title compound. $^1$H NMR (400 MHz, DMSO-d$_6$) δ 13.11 (s, 1H), 8.25 (s, 1H), 8.04 (d, 1H), 7.83 (d, 1H), 7.67 (t, 1H), 7.52 (t, 2H), 7.42 (s, 1H), 7.32 (t, 1H), 7.04 (dd, 2H), 5.35-5.32 (m, 1H), 4.17-4.14 (m, 1H), 4.04-3.98 (m, 1H), 3.80 (s, 3H), 3.62-3.59 (m, 2H), 3.44-3.41 (m, 1H), 3.31-3.24 (m, 2H), 2.79 (s, 3H), 1.72-1.65 (m, 2H), 1.30-1.24 (m, 2H). LC-MS m/z [M+H]$^+$=604.

Example 26: Preparation of 3-methoxy-4-(1-(2-(2-methoxyphenyl)-2-((tetrahydro-2H-pyran-4-yl)oxy) ethyl)-5-methyl-6-(oxazol-2-yl)-2,4-dioxo-1,4-dihydrothieno[2,3-d]pyrimidin-3(2H)-yl)benzoic Acid

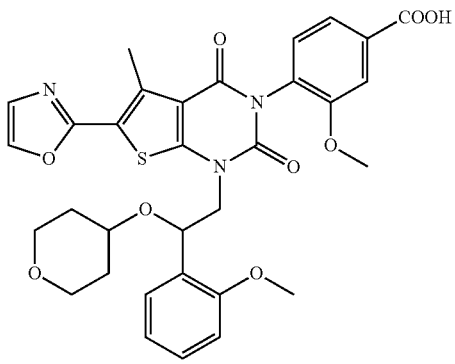 [SMILES: COc1ccccc1C(Cn1c(=O)n(-c2ccc(C(=O)O)cc2OC)c(=O)c2c(C)c(-c3ncco3)sc21)OC1CCOCC1]

Step 1: Preparation of ethyl 2-(3-(2-methoxy-4-(methoxycarbonyl)phenyl)ureido)-4-methylthiophene-3-carboxylate

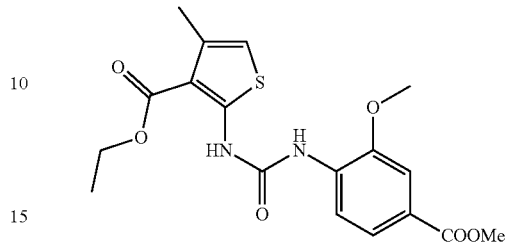

The preparation method was the same as that of ethyl 2-(3-(4-(tert-butoxycarbonyl)phenyl)ureido)-4-methylthiophene-3-carboxylate in Step 1 of Example 24, except that the starting material tert-butyl 4-aminobenzoate was replaced with methyl 4-amino-3-methoxybenzoate (4.7 g, 25.9 mmol) to obtain 3.2 g of the title compound. LC-MS m/z [M+H]$^+$=393.

Step 2: Preparation of 3-methoxy-4-(1-(2-(2-methoxyphenyl)-2-((tetrahydro-2H-pyran-4-yl)oxy) ethyl)-)5-methyl-6-(oxazol-2-yl)-2,4-dioxo-1,4-dihydrothieno[2,3-d]pyrimidin-3(2H)-yl)benzoic Acid

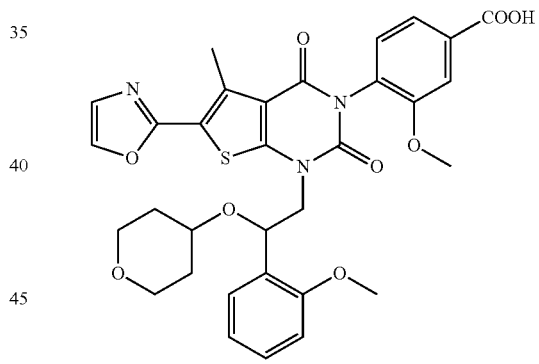

The preparation method was the same as that of 4-(1-(2-(2-methoxyphenyl)-2-((tetrahydro-2H-pyran-4-yl)oxy) ethyl)-5-methyl-6-(oxazol-2-yl)-2, 4-dioxo-1,4-dihydrothieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with ethyl 2-(3-(2-methoxy-4-(methoxycarbonyl)phenyl)ureido)-4-methylthiophene-3-carboxylate as prepared in Step 1 of Example 26 to obtain 48 mg of the title compound. $^1$H NMR (400 MHz, DMSO-d$_6$) δ 13.11 (s, 1H), 8.25 (d, 1H), 7.67-7.64 (m, 2H), 7.53-7.48 (m, 1H), 7.41 (d, 1H), 7.38-7.31 (m, 2H), 7.05-7.03 (m, 2H), 5.35-5.27 (m, 1H), 4.30-4.04 (m, 2H), 3.84 (s, 3H), 3.80 (s, 3H), 3.64-3.48 (m, 4H), 3.26-3.23 (m, 1H), 2.78 (s, 3H), 1.65-1.63 (m, 2H), 1.36-1.34 (m, 2H). LC-MS m/z [M+H]$^+$=634.2.

Example 27: 4-Methoxy-3-(1-(2-(2-methoxyphe-nyl)-2-(tetrahydro-2H-pyran-4-yl)oxy)-ethyl]-5-methyl-6-oxazol-2-yl)-2,4-dioxo-1,4-dihydrothieno[2,3-d]pyrimidin-3(2H)-yl)-benzoic Acid

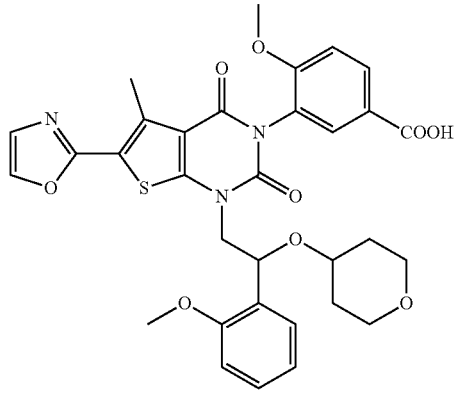 [SMILES: COc1ccccc1C(Cn1c(=O)n(-c2cc(C(=O)O)ccc2OC)c(=O)c2c(C)c(-c3ncco3)sc21)OC1CCOCC1]

Step 1: Preparation of ethyl 2-(3-(2-methoxy-5-(methoxycarbonyl)phenyl)ureido)-4-methylthi-ophene-3-carboxylate

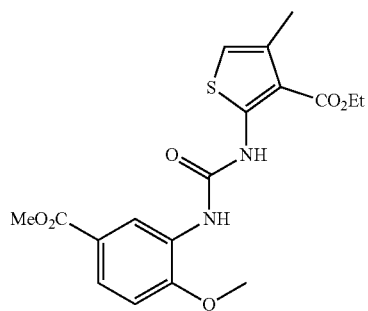 [SMILES: CCOC(=O)c1c(C)csc1NC(=O)Nc1cc(C(=O)OC)ccc1OC]

The preparation method was the same as that of ethyl 2-(3-(4-(tert-butoxycarbonyl)phenyl)ureido)-4-methylthi-ophene-3-carboxylate in Step 1 of Example 24, except that the starting material tert-butyl 4-aminobenzoate was replaced with methyl 3-amino-4-methoxybenzoate (4.7 g, 25.9 mmol) to obtain 8.4 g of the title compound. LC-MS m/z [M+H]⁺=393.

Step 2: Preparation of 4-methoxy-3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic Acid

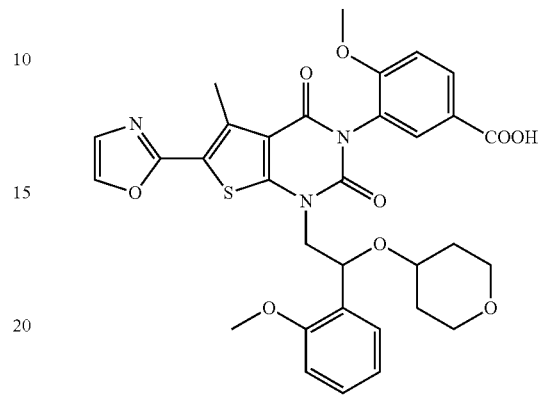

The preparation method was the same as that of 4-(1-(2-(2-methoxyphenyl)-2-((tetrahydro-2H-pyran-4-yl)oxy)ethyl)-5-methyl-6-(oxazol-2-yl)-2, 4-dioxo-1,4-dihydroth-ieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with ethyl 2-(3-(2-methoxy-5-(methoxycarbonyl)phenyl)ureido)-4-methylthiophene-3-carboxylate as prepared in Step 1 of Example 27 to obtain 19 mg of the title compound. $^1$H NMR (400 MHz, DMSO-$d_6$) δ 12.09 (s, 1H), 8.18 (d, 1H), 7.94-7.92 (m, 1H), 7.90 (d, 1H), 7.88 (d, 1H), 7.56 (d, 1H), 7.35-7.69 (m, 1H), 7.21 (d, 1H), 7.06-7.01 (m, 1H), 6.98-6.92 (m, 1H), 5.50-5.44 (m, 1H), 4.35-3.98 (m, 2H), 3.93-3.87 (m, 6H), 3.82-3.65 (m, 2H), 3.54-3.36 (m, 3H), 2.86 (d, 3H), 1.84-1.72 (m, 2H), 1.62-1.44 (m, 2H). LC-MS m/z [M+H]⁺=634.2.

Example 28: 2-Fluoro-3-(1-(2-(2-methoxyphenyl)-2-((tetrahydro-2H-pyran-4-yl)oxy) ethyl)-5-methyl-6-(oxazol-2-yl)-2,4-dioxo-1,4-dihydrothieno[2,3-d]pyrimidin-3(2H)-yl)benzoic Acid

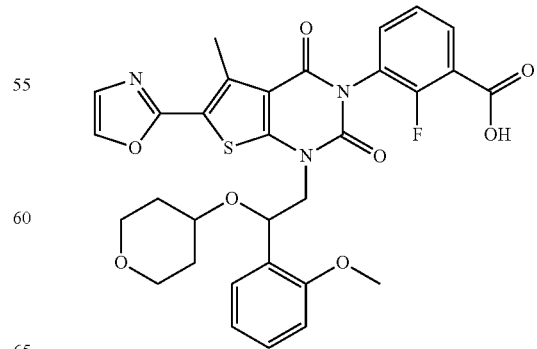

Step 1: Preparation of ethyl 3-amino-2-fluorobenzoate

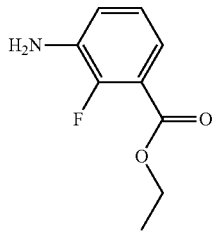

Under argon protection, thionyl chloride (10 mL) was slowly added dropwise to anhydrous ethanol (30 mL) at −10° C. After the dropwise adding, 3-amino-2-fluorobenzoic acid (5 g, 32.3 mmol) was added into the reaction flask and refluxed at 80° C. overnight. After completion of the reaction, the reaction mixture was adjusted to be a pH of weakly alkaline with a saturated solution of sodium hydrogen carbonate and extracted with ethyl acetate. The organic phase was dried and concentrated to obtain 5.7 g of the title compound. LC-MS m/z [M+H]$^+$=184.

Step 2: Preparation of ethyl 2-(3-(3-(ethoxycarbonyl)-2-fluorophenyl)ureido)-4-methylthiophene-3-carboxylate

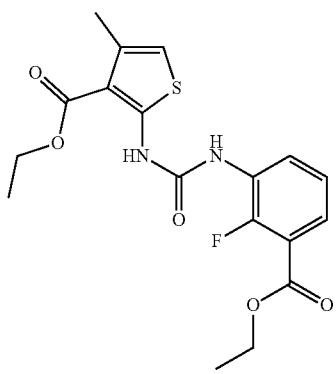 [SMILES: CCOC(=O)c1cccc(NC(=O)Nc2scc(C)c2C(=O)OCC)c1F]

The preparation method was the same as that of ethyl 2-(3-(4-(tert-butoxycarbonyl)phenyl)ureido)-4-methylthiophene-3-carboxylate in Step 1 of Example 24, except that the starting material tert-butyl 4-aminobenzoate was replaced with ethyl 3-amino-2-fluorobenzoate (4.74 g, 25.9 mmol) to obtain 3.75 g of the title compound. LC-MS m/z [M+H]$^+$=395.

Step 3: Preparation of 2-fluoro-3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic Acid

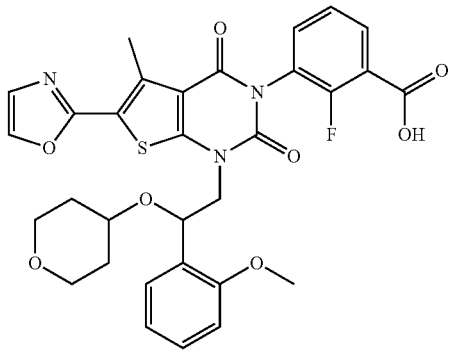 [SMILES: COc1ccccc1C(Cn1c(=O)n(-c2cccc(C(=O)O)c2F)c(=O)c2c(C)c(-c3ncco3)sc21)OC1CCOCC1]

The preparation method was the same as that of 4-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with ethyl 2-(3-(3-(ethoxycarbonyl)-2-fluorophenyl) ureido)-4-methylthiophene-3-carboxylate as prepared in Step 2 of Example 28 to obtain 83 mg of the title compound. $^1$H NMR (400 MHz, DMSO-d$_6$) δ 13.51 (s, 1H), 8.27 (s, 1H), 8.02-7.99 (m, 1H), 7.69 (s, 1H), 7.54-7.46 (m, 2H), 7.43 (s, 1H), 7.33 (dd, 1H), 7.08-7.01 (m, 2H), 5.36-5.30 (m, 1H), 4.34-3.81 (m, 2H), 3.81 (s, 3H), 3.63-3.62 (m, 1H), 3.54-3.46 (m, 1H), 3.40-3.22 (m, 3H), 2.80-2.79 (m, 3H), 1.65 (s, 2H), 1.37-1.24 (m, 2H). LC-MS m/z [M+H]$^+$=622.

Example 29: 2-Methoxy-3-(1-(2-(2-methoxyphenyl)-2-((tetrahydro-2H-pyran-4-yl) oxy)ethyl)-5-methyl-6-(oxazol-2-yl)-2,4-dioxo-1,4-dihydrothieno[2,3-d]pyrimidin-3(2H)-yl)benzoic Acid

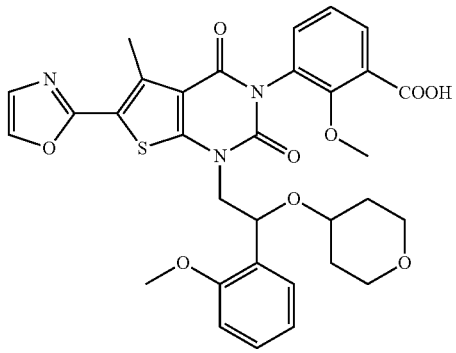 [SMILES: COc1ccccc1C(Cn1c(=O)n(-c2cccc(C(=O)O)c2OC)c(=O)c2c(C)c(-c3ncco3)sc21)OC1CCOCC1]

Step 1: Preparation of methyl 2-methoxy-3-nitrobenzoate

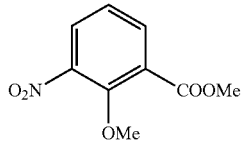 [SMILES: COC(=O)c1cccc([N+](=O)[O-])c1OC]

Methyl 3-nitrosalicylate (6 g, 30.43 mmol), potassium carbonate (16.82 g, 121.73 mmol) and iodomethane (12.96 g, 91.30 mmol) were added to N,N-dimethylformamide. Under argon protection, the reaction was carried out at 60° C. for 4 h. After completion of the reaction, the mixture was quenched with water (20 mL) and extracted with ethyl acetate (40 mL). The organic phase was separated, extracted twice with water (20 mL), dried, concentrated and subjected to column chromatography to give 5 g of the title compound.

Step 2: Preparation of methyl 3-amino-2-methoxybenzoate

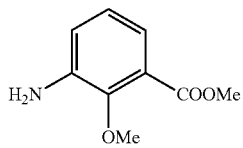

Methyl 2-methoxy-3-nitrobenzoate (5 g, 18.94 mmol), iron powder (4.75 g, 85.18 mmol), ammonium chloride (7 g, 130.31 mmol), water (20 mL), methanol (40 mL) and tetrahydrofuran (20 mL) were added to a reaction flask, and reacted at 70° C. for 5 h. After completion of the reaction, the mixture was filtered and the filtrate was concentrated. And then water (20 mL) was added, and the mixture was extracted twice with ethyl acetate (40 mL). The organic phase was dried and concentrated to obtain 4.2 g of the title compound.

Step 3: Preparation of ethyl 2-(3-(2-methoxy-3-(methoxycarbonyl)phenyl)ureido)-4-methylthiophene-3-carboxylate

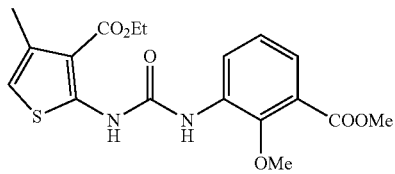 [SMILES: CCOC(=O)c1c(C)csc1NC(=O)Nc1cccc(C(=O)OC)c1OC]

The preparation method was the same as that of ethyl 2-(3-(4-(tert-butoxycarbonyl)phenyl)ureido)-4-methylthiophene-3-carboxylate in Step 1 of Example 24, except that the starting material tert-butyl 4-aminobenzoate was replaced with methyl 3-amino-2-methoxybenzoate (4.7 g, 25.9 mmol) as prepared in Step 2 of Example 29 to obtain 2 g of the title compound. LC-MS m/z [M+H]$^+$=393.15.

Step 4: Preparation of 2-methoxy-3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic Acid

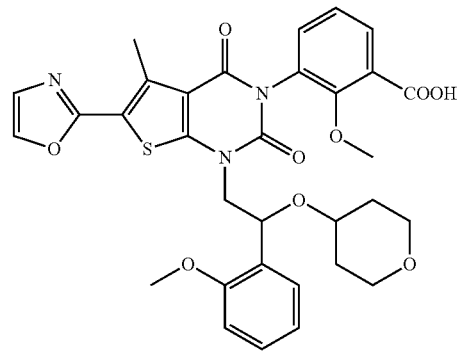 [SMILES: COc1ccccc1C(Cn1c(=O)n(-c2cccc(C(=O)O)c2OC)c(=O)c2c(C)c(-c3ncco3)sc21)OC1CCOCC1]

The preparation method was the same as that of 4-(1-(2-(2-methoxyphenyl)-2-((tetrahydro-2H-pyran-4-yl)oxy)ethyl)-5-methyl-6-(oxazol-2-yl)-2, 4-dioxo-1,4-dihydrothieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with ethyl 2-(3-(2-methoxy-3-(methoxycarbonyl)phenyl)ureido)-4-methylthiophene-3-carboxylate as prepared in Step 3 of Example 29 to obtain 45 mg of the title compound. $^1$H NMR (400 MHz, DMSO-d$_6$) δ 13.00 (s, 1H), 8.25 (s, 1H), 7.80 (d, 1H), 7.53-7.51 (m, 1H), 7.44-7.41 (m, 2H), 7.32-7.30 (m, 2H), 7.03-7.01 (m, 2H), 5.29-5.28 (m, 1H), 4.31 (d, 1H), 4.09 (s, 1H), 3.79 (s, 3H), 3.65 (s, 3H), 3.44-3.26 (m, 5H), 2.78 (s, 3H), 1.65-1.54 (m, 2H), 1.34-1.33 (m, 2H). LC-MS m/z [M+H]$^+$=634.2.

Example 30: 4-Fluoro-3-(1-(2-(2-methoxyphenyl)-2-((tetrahydro-2H-pyran-4-yl)oxy) ethyl)-5-methyl-6-(oxazol-2-yl)-2,4-dioxo-1,4-dihydrothieno[2,3-d]pyrimidin-3(2H)-yl)benzoic Acid

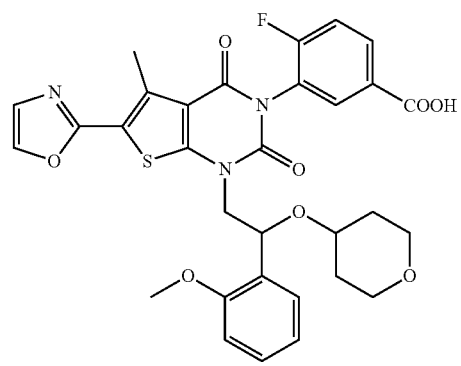 [SMILES: COc1ccccc1C(Cn1c(=O)n(-c2cc(C(=O)O)ccc2F)c(=O)c2c(C)c(-c3ncco3)sc21)OC1CCOCC1]

Step 1: Preparation of ethyl 2-(3-(2-fluoro-5-(methoxycarbonyl)phenyl)ureido)-4-methylthiophene-3-carboxylate

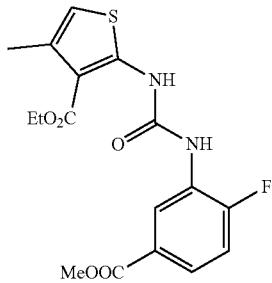 [SMILES: CCOC(=O)c1c(C)csc1NC(=O)Nc1cc(C(=O)OC)ccc1F]

The preparation method was the same as that of ethyl 2-(3-(4-(tert-butoxycarbonyl)phenyl)ureido)-4-methylthiophene-3-carboxylate in Step 1 of Example 24, except that the starting material tert-butyl 4-aminobenzoate was replaced with methyl 3-amino-4-fluorophenylcarboxylate (4.38 g, 25.9 mmol) to obtain 1 g of the title compound. LC-MS m/z [M+H]$^+$=381.2.

Step 2: Preparation of 4-fluoro-3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic Acid

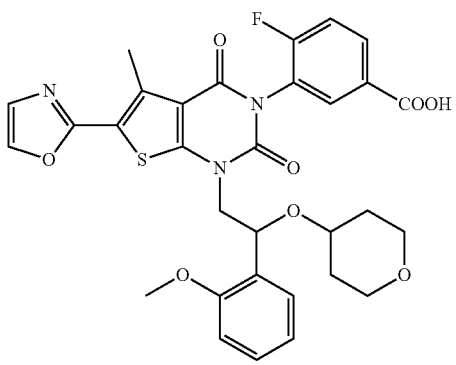 [SMILES: COc1ccccc1C(Cn1c(=O)n(-c2cc(C(=O)O)ccc2F)c(=O)c2c(C)c(-c3ncco3)sc21)OC1CCOCC1]

The preparation method was the same as that of 4-(1-(2-(2-methoxyphenyl)-2-((tetrahydro-2H-pyran-4-yl)oxy)ethyl)-5-methyl-6-(oxazol-2-yl)-2, 4-dioxo-1,4-dihydrothieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with 4-fluoro-3-(1-(2-(2-methoxyphenyl)-2-((tetrahydro-2H-pyran-4-yl)oxy)ethyl)-5-methyl-6-(oxazol-2-yl)-2,4-dioxo-1,4-dihydrothieno[2,3-d]pyrimidin-3(2H)-yl)benzoic acid as prepared in Step 1 of Example 30 to obtain 45 mg of the title compound. $^1$H NMR (400 MHz, DMSO-d$_6$) δ 13.00 (s, 1H), 8.19 (s, 1H), 7.99-7.97 (m, 2H), 7.55-7.54 (m, 1H), 7.44-7.40 (m, 1H), 7.29-7.30 (m, 2H), 6.97-7.04 (m, 2H), 5.50-5.47 (m, 1H), 4.32 (d, 1H), 4.11-4.03 (m, 1H), 3.85 (s, 3H), 3.77-3.73 (m, 2H), 3.48-3.46 (m, 1H), 3.39-3.35 (m, 2H), 2.84-2.83 (m, 3H), 1.76-1.73 (m, 2H),1.53-1.43 (m, 2H). LC-MS m/z [M+H]$^+$=622.2.

Example 31: 3-(3-(2-Fluoroethoxy)cyclobutyl)-1-(2-(2-methoxyphenyl)-2-((tetrahydro-2H-pyran-4-)yl)oxy)ethyl)-5-methyl-6-(oxazol-2-yl)thieno[2,3-d]pyrimidin-2,4(1H,3H)-dione

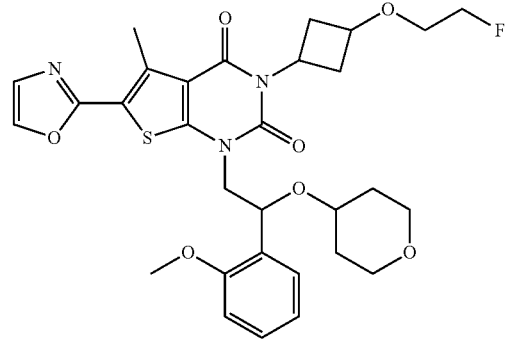 [SMILES: COc1ccccc1C(Cn1c(=O)n(C2CC(OCCF)C2)c(=O)c2c(C)c(-c3ncco3)sc21)OC1CCOCC1]

Step 1: Preparation of tert-butyl 3-hydroxycyclobutylcarbamate

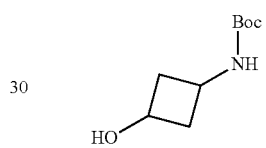

Tert-butyl 3-oxocyclobutylcarbamate (5 g, 26.99 mmol) was dissolved in ethonol (50 mL). At 0° C., sodium borohydride (525 mg, 13.87 mmol) was added, and the mixture was stirred at room temperature for 2 h. After completion of the reaction, the reaction mixture was concentrated, and then aqueous solution of sodium bicarbonate (10 mL) was added and the mixture was extracted with dichloromethane (30 mL) for 3 times. The organic phases were combined, washed with a saturated aqueous solution of sodium chloride, dried over anhydrous sodium chloride, concentrated under reduced pressure to obtain 4.8 g of the title compound.

Step 2: Preparation of tert-butyl (3-(2-fluoroethoxy)cyclobutyl)carbamate

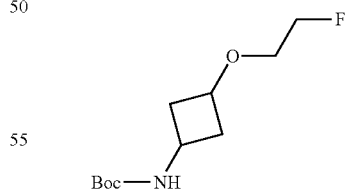

Sodium hydrogen (60%) (1.7 g, 71.2 mmol) was added to a reaction flask and tert-butyl 3-hydroxycyclobutylcarbamate (4 g, 21.36 mmol), 1-bromo-2-ethyl fluoride (4.07 g, 32.04 mmol), anhydrous tetrahydrofuran (40 mL) were added under argon protection. The mixture was stirred at room temperature overnight. After completion of the reaction, the mixture was filtered, the filtrate was concentrated and subjected to column chromatography to obtain 4 g of the title compound.

Step 3: Preparation of 3-(2-fluoroethoxy)cyclobutyl-1-amine

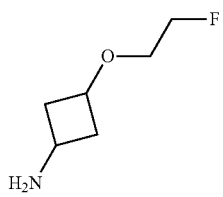

Tert-butyl (3-(2-fluoroethoxy)cyclobutyl)carbamate (4 g, 17.15 mmol) was dissolved in a solution of hydrochloric acid (2 M)/ethyl acetate (43 mL, 85.73 mmol). After completion of the reaction, the mixture was adjusted to pH=6-7 with a saturated solution of sodium bicarbonate, and extracted with ethyl acetate (60 mL) for 3 times. The organic phases were combined, washed with saturated solution of sodium chloride once, dried over anhydrous sodium sulfate and concentrated under a reduced pressure to obtain 2.2 g of the title compound.

Step 4: Preparation of ethyl 2-(3-(3-(2-fluoroethoxy)cyclobutyl)ureido)-4-methylthiophene-3-carboxylate

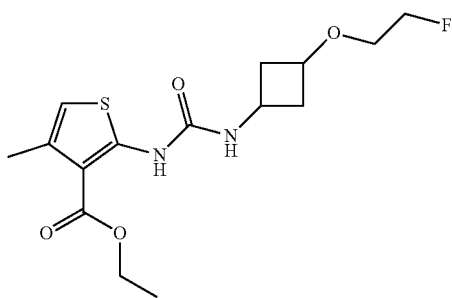 [SMILES: CCOC(=O)c1c(C)csc1NC(=O)NC1CC(OCCF)C1]

The preparation method was the same as that of ethyl 2-(3-(4-(tert-butoxycarbonyl)phenyl)ureido)-4-methylthiophene-3-carboxylate in Step 1 of Example 24, except that the starting material tert-butyl 4-aminobenzoate was replaced with 3-(2-fluoroethoxy)cyclobutyl-1-amine (3.45 g, 25.9 mmol) as prepared in Step 3 of Example 31 to obtain 1 g of the title compound.

Step 5: Preparation of 3-(3-(2-fluoroethoxy)cyclobutyl)-1-(2-(2-methoxyphenyl)-2-((tetrahydro-2H-pyran-4-yl)oxy)ethyl)-5-methyl-6-(oxazol-2-yl)thieno[2,3-d]pyrimidine-2,4(1H, 3H)-dione

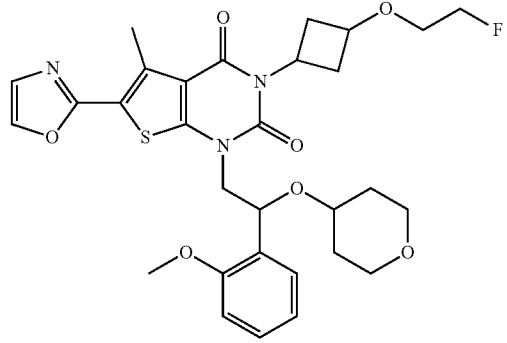 [SMILES: COc1ccccc1C(Cn1c(=O)n(C2CC(OCCF)C2)c(=O)c2c(C)c(-c3ncco3)sc21)OC1CCOCC1]

The preparation method was the same as that of 4-(1-(2-(2-methoxyphenyl)-2-((tetrahydro-2H-pyran-4-yl)oxy)ethyl)-5-methyl-6-(oxazol-2-yl)-2, 4-dioxo-1,4-dihydrothieno[2,3-d]pyrimidin-3(2H)-yl)benzoic acid in steps 2-6 of Example 24, except that the starting material ethyl 2-(3-(4-(tert-butoxycarbonyl)phenyl)ureido)-4-methylthiophene-3-carboxylate was replaced with ethyl 2-(3-(3-(2-fluoroethoxy)cyclobutyl) ureido)-4-methylthiophene-3-carboxylate as prepared in Step 4 of Example 31 to obtain 1.8 g of the title compound. $^1$H NMR (400 MHz, DMSO-$d_6$) δ 8.23 (s, 1H), 7.49 (dd, 1H), 7.38 (d, 1H), 7.30 (m, 1H), 7.03 (dd, 1H), 6.98 (d, 1H), 5.50-5.57 (m, 1H), 5.29-5.32 (m, 1H), 4.60-4.62 (m, 1H), 4.49-4.52 (m, 1H), 4.30-4.33 (m, 1H), 4.41-4.05 (m, 2H), 3.78 (s, 3H), 3.60-3.53 (m, 2H), 3.35-3.58 (m, 1H), 3.20-3.25 (m, 2H), 2.90-2.95 (m, 2H), 2.79 (s, 3H), 2.26-2.30 (m, 2H), 1.61-1.65 (m, 2H), 1.32-1.35 (m, 2H), 1.17-1.20 (m, 2H). LC-MS m/z [M+H]$^+$=600.2

The preparation methods of examples 32 to 55 were carried out in accordance with the preparation methods of examples 1 to 31, and the structures of the compounds of examples 32 to 55 are shown in Table 1:

TABLE 1

| Example number | Compound structure | m/z |
|---|---|---|
| Example 32 | 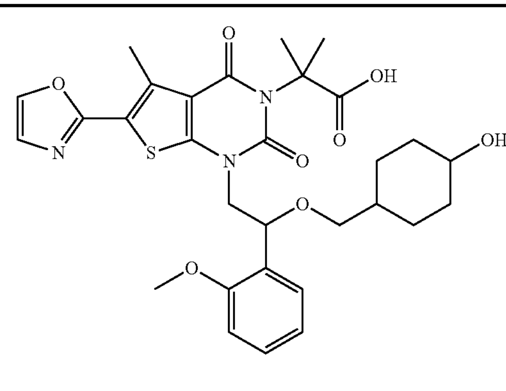 | 598.2 [M + H]$^+$ |

TABLE 1-continued
| Example number | Compound structure | m/z |
|---|---|---|
| Example 33 | 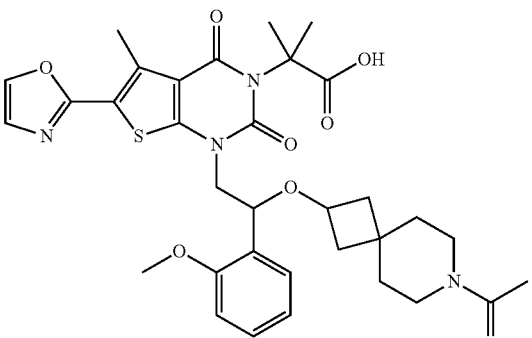 | 651.2 [M + H]+ |
| Example 34 | 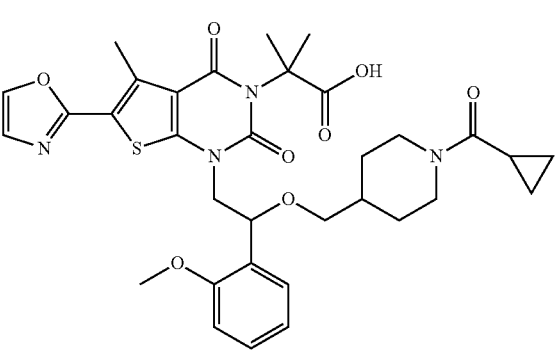 [SMILES: COc1ccccc1C(Cn1c(=O)n(C(C)(C)C(=O)O)c(=O)c2c(C)c(-c3ncco3)sc21)OCC1CCN(C(=O)C2CC2)CC1] | 651.2 [M + H]+ |
| Example 35 | 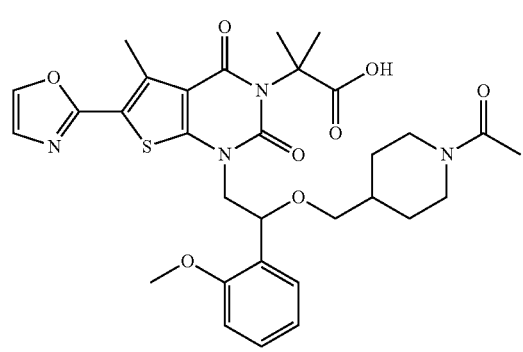 [SMILES: COc1ccccc1C(Cn1c(=O)n(C(C)(C)C(=O)O)c(=O)c2c(C)c(-c3ncco3)sc21)OCC1CCN(C(C)=O)CC1] | 625.2 [M + H]+ |
| Example 36 | 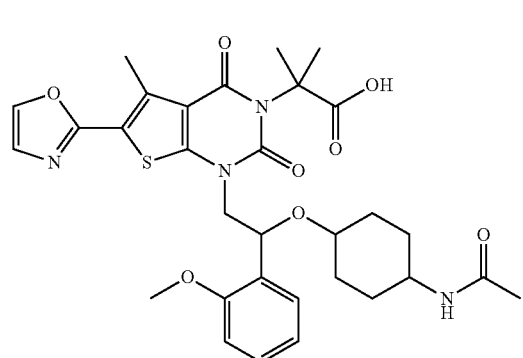 | 625.1 [M + H]+ |

TABLE 1-continued
| Example number | Compound structure | m/z |
|---|---|---|
| Example 37 | 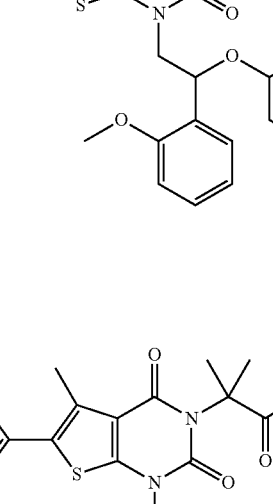 | 609.2 [M + H]+ |
| Example 38 | 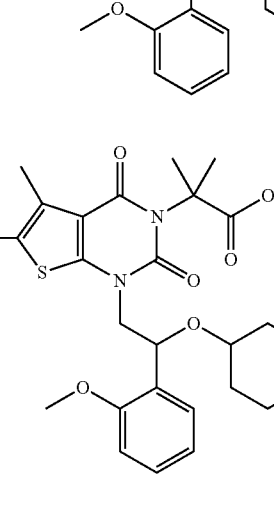 | 606.2 [M + H]+ |
| Example 39 | 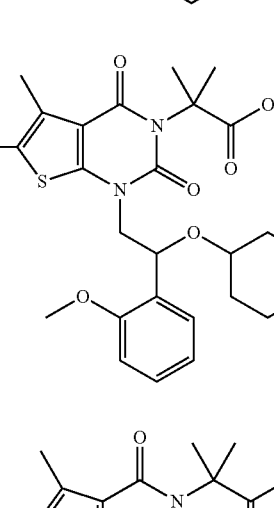 | 634.2 [M + H]+ |
| Example 40 | 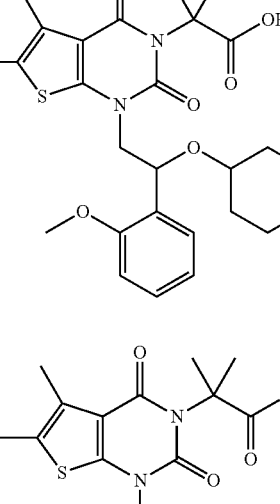 | 623.2 [M + H]+ |

TABLE 1-continued

| Example number | Compound structure | m/z |
|---|---|---|
| Example 41 | 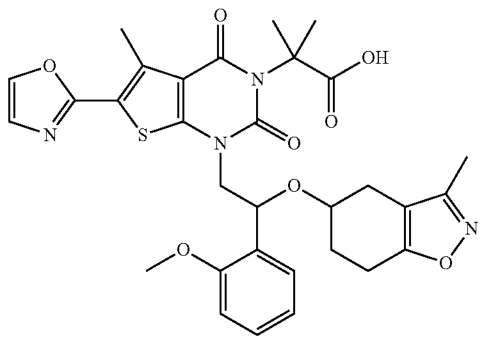 [SMILES: COc1ccccc1C(Cn1c(=O)n(C(C)(C)C(=O)O)c(=O)c2c(C)c(-c3ncco3)sc21)OC1CCc2onc(C)c2C1] | 621.2 [M + H]+ |
| Example 42 | 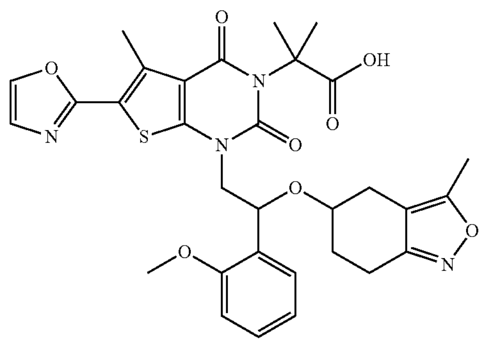 [SMILES: COc1ccccc1C(Cn1c(=O)n(C(C)(C)C(=O)O)c(=O)c2c(C)c(-c3ncco3)sc21)OC1CCc2noc(C)c2C1] | 621.2 [M + H]+ |
| Example 43 | 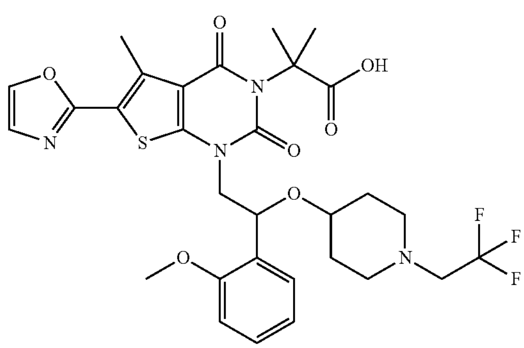 [SMILES: COc1ccccc1C(Cn1c(=O)n(C(C)(C)C(=O)O)c(=O)c2c(C)c(-c3ncco3)sc21)OC1CCN(CC(F)(F)F)CC1] | 651.2 [M + H]+ |
| Example 44 | 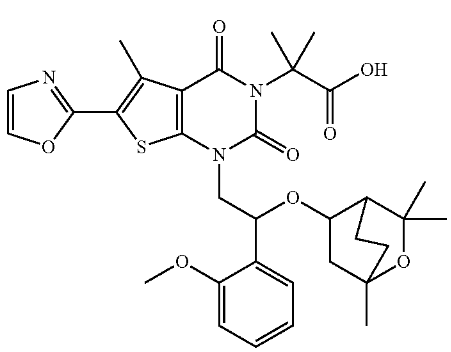 [SMILES: COc1ccccc1C(Cn1c(=O)n(C(C)(C)C(=O)O)c(=O)c2c(C)c(-c3ncco3)sc21)OC1CC2(C)CCC1C(C)(C)O2] | 638.2 [M + H]+ |

TABLE 1-continued

| Example number | Compound structure | m/z |
|---|---|---|
| Example 45 | 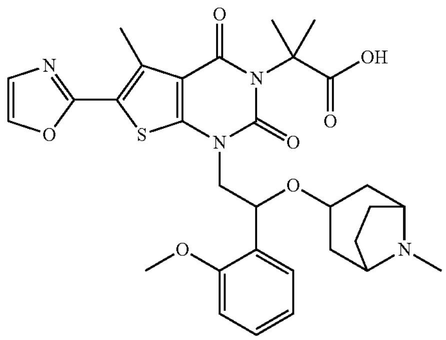 [SMILES: COc1ccccc1C(Cn1c(=O)n(C(C)(C)C(=O)O)c(=O)c2c(C)c(-c3ncco3)sc21)OC1CC2CCC(C1)N2C] | 609.2 [M + H]+ |
| Example 46 | 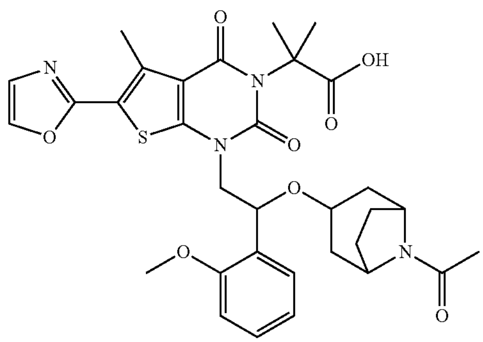 [SMILES: COc1ccccc1C(Cn1c(=O)n(C(C)(C)C(=O)O)c(=O)c2c(C)c(-c3ncco3)sc21)OC1CC2CCC(C1)N2C(C)=O] | 637.2 [M + H]+ |
| Example 47 | 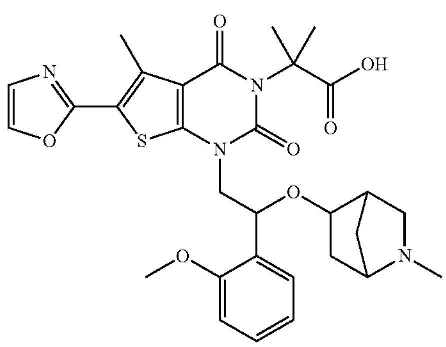 [SMILES: COc1ccccc1C(Cn1c(=O)n(C(C)(C)C(=O)O)c(=O)c2c(C)c(-c3ncco3)sc21)OC1CC2CC1CN2C] | 595.2 [M + H]+ |
| Example 48 | 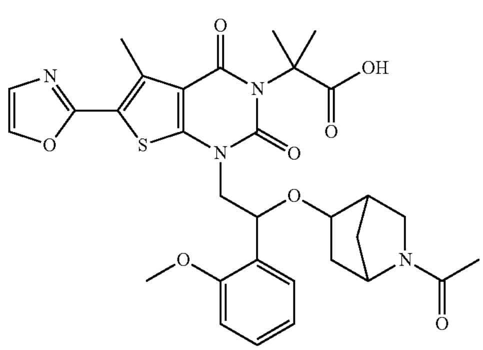 [SMILES: COc1ccccc1C(Cn1c(=O)n(C(C)(C)C(=O)O)c(=O)c2c(C)c(-c3ncco3)sc21)OC1CC2CC1CN2C(C)=O] | 623.2 [M + H]+ |

TABLE 1-continued

| Example number | Compound structure | m/z |
|---|---|---|
| Example 49 | 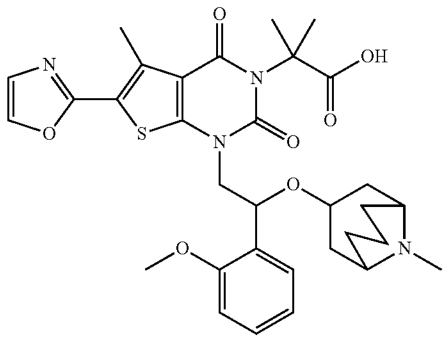 [SMILES: COc1ccccc1C(Cn1c(=O)n(C(C)(C)C(=O)O)c(=O)c2c(C)c(-c3ncco3)sc21)OC1CC2CCCC(C1)N2C] | 623.3 [M + H]+ |
| Example 50 | 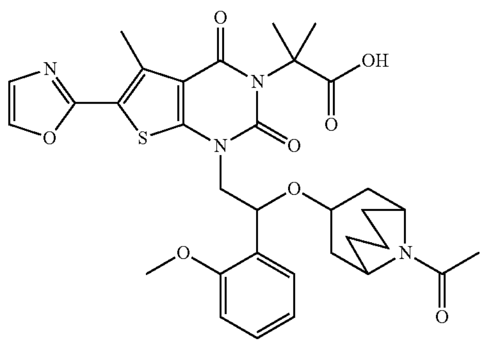 | 651.2 [M + H]+ |
| Example 51 | 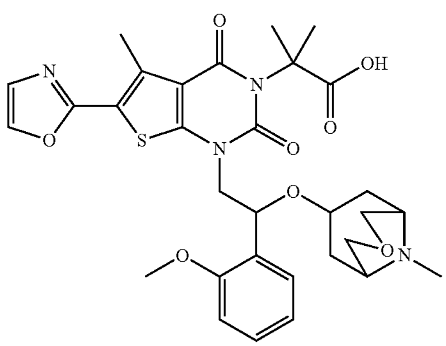 [SMILES: COc1ccccc1C(Cn1c(=O)n(C(C)(C)C(=O)O)c(=O)c2c(C)c(-c3ncco3)sc21)OC1CC2COCC(C1)N2C] | 625.2 [M + H]+ |
| Example 52 | 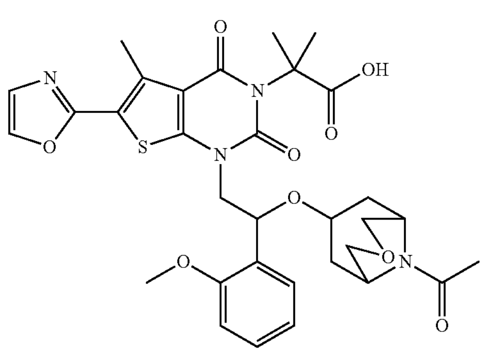 [SMILES: COc1ccccc1C(Cn1c(=O)n(C(C)(C)C(=O)O)c(=O)c2c(C)c(-c3ncco3)sc21)OC1CC2COCC(C1)N2C(C)=O] | 653.2 [M + H]+ |

TABLE 1-continued
| Example number | Compound structure | m/z |
|---|---|---|
| Example 53 | 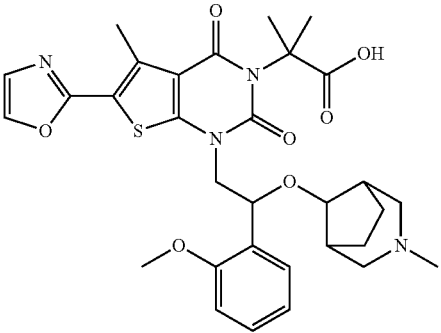 [SMILES: COc1ccccc1C(Cn1c(=O)n(C(C)(C)C(=O)O)c(=O)c2c(C)c(-c3ncco3)sc21)OC1C2CCC1CN(C)C2] | 609.2 [M + H]+ |
| Example 54 | 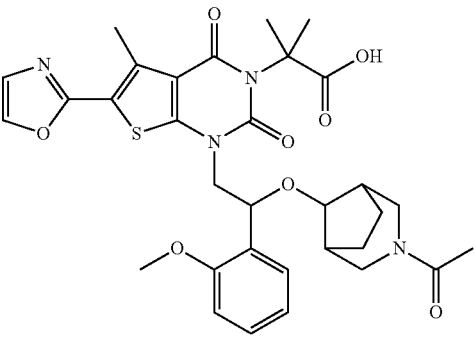 [SMILES: COc1ccccc1C(Cn1c(=O)n(C(C)(C)C(=O)O)c(=O)c2c(C)c(-c3ncco3)sc21)OC1C2CCC1CN(C(C)=O)C2] | 637.2 [M + H]+ |
| Example 55 | 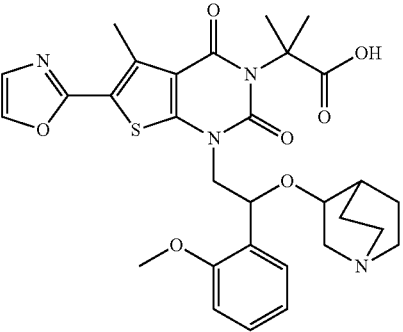 [SMILES: COc1ccccc1C(Cn1c(=O)n(C(C)(C)C(=O)O)c(=O)c2c(C)c(-c3ncco3)sc21)OC1CN2CCC1CC2] | 595.2 [M + H]+ |
| Example 56 | 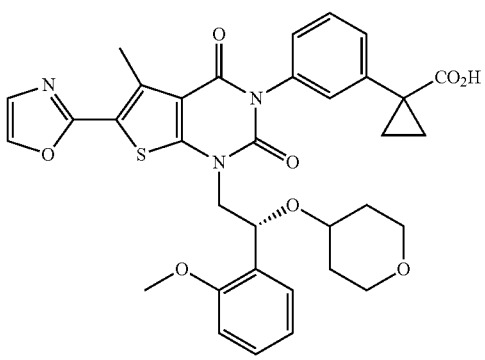 [SMILES: COc1ccccc1[C@H](Cn1c(=O)n(-c2cccc(C3(C(=O)O)CC3)c2)c(=O)c2c(C)c(-c3ncco3)sc21)OC1CCOCC1] | 644.2 [M + H]+ |

Experimental Example 1 In Vitro Inhibition Experiment of Acetyl-CoA Carboxylase (ACC)

1. Experimental Materials 1.1 Compounds

Control compound is compound ND-630 disclosed in Example I-181 of the patent WO2013/071169 (which is currently the most promising drug for such diseases in the clinic), of which the chemical name is (2-[1-[2-(2-methoxyphenyl)-2-(oxecyclo-4-yloxy)ethyl]-5-methyl-6-(1,3-oxazol-2-yl)-2,4-dioxo-1H,2H,3H,4H-thieno[2,3-d]pyrimidin-3-yl]-2-methylpropanoic acid). The control compound was prepared according to the method described in WO2013/071169 and identified by hydrogen spectroscopy and mass spectrometry.

Compound preparation: the compounds of the present disclosure prepared in the above examples and the control compound were respectively formulated into 10 mM with DMSO for use. In the experiments, the above compounds were used from a concentration of 1000 nM and diluted for 3 times successively, i.e., 1000 nM, 333.3 nM, 111.1 nM, and 37.1 nM, 12.3 nM, 4.12 nM, 1.37 nM, 0.46 nM, 0.15 nM and 0.05 nM, respectively.

1.2 Reagents

HEPES buffer was purchased from Invitrogen; $MgCl_2$, potassium citrate buffer solution, DTT, acetyl-CoA and $NaHCO_3$ were purchased from Sigma; BRIJ-35 was purchased from MERCK; ACC1 and ACC2 enzymes each was purchased from BPS; ADP-Glo™ kinase Kit was purchased from Promega.

1.3 Consumables and Instruments

96-Well polypropylene plates were purchased from Nunc; oscillators were purchased from QILINBEIER; centrifuges were purchased from Eppendorf; 384-well white plates and Envision 2104 plate readers were purchased from Perkin Elmer.

2. Experimental Methods 2.1. Reagent Preparation

Preparation of 1× reaction buffer (pH=7.4): HEPES stock solutions (1 M), $MgCl_2$ (1 M), BRIJ-35 (10%), potassium citrate buffer (1 M), BSA (10 mg/mL) and DTT (500 mM) were formulated to enzyme reaction buffer containing HEPES (50 mM), $MgCl_2$ (2 mM), BRIJ-35 (0.01%), potassium citrate buffer (2 mM), BSA (50 Gg/mL) and DTT (2 mM).

2.2. ACC Enzyme Activity Assay

1) ACC1 Enzyme Activity Assay 4.5 µL of 2.2×ACC1 enzyme (2 nM) working solution was added to a 384-well plate; and then 0.5 µL of different concentrations of compound were added. The mixture was incubated at room temperature for 15 min.

2× Substrate (40 µM ATP, 20 µM acetyl CoA, 60 mM $NaHCO_3$) was prepared using the buffer prepared in 2.1; 5 µL of 2× substrate was added to the 384-well plate, and the mixture was incubated at room temperature for 30 min; 10 µL ADP-Glo reagent was added, the mixture was incubated at room temperature for 40 min, and then the reaction was terminated; finally, 20 µL of the enzyme detection reagent was added, the mixture was incubated at room temperature for 40 min, and an Envision 2104 instrument was used to read the relative light units (RLU).

2) ACC2 Enzyme Activity Assay 4.5 µL of 2.2×ACC2 enzyme (1.1 nM) working solution was added to a 384-well plate; and then 0.5 µL of different concentrations of compound were added. The mixture was incubated at room temperature for 15 min.

2× Substrate (40 µM ATP, 40 µM acetyl CoA, 24 mM $NaHCO_3$) was prepared using the buffer prepared in 2.1; 5 µL of 2× substrate was added to the 384-well plate, and the mixture was incubated at room temperature for 30 min; then 10 µL ADP-Glo reagent was added, the mixture was incubated at room temperature for 40 min, and then the reaction was terminated; finally, 20 µL of the enzyme detection reagent was added, the mixture was incubated at room temperature for 40 min, and an Envision 2104 instrument was used to read the relative light units (RLU).

3. Experimental Data Analysis

Negative control group: menstruum containing 5% DMSO; positive control group: menstruum containing 100 nM ND-630. The average values of each concentration and the positive and negative controls were calculated, and the standard deviation was calculated. The inhibition percentage was calculated by using the following formula: inhibition rate $(100\%)=100\times (RLU_{negative\ control}-RLU_{compound})/(RLU_{negative\ control}-RLU_{positive\ control})$. The inhibition rate data was fitted by nonlinear regression equation to calculate $IC_{50}$ of each compound. The nonlinear regression equation was Y=lowest value+(highest value−lowest value)/$(1+10^{((Log\ IC50-X)\times HillSlope)})$, among which X is logarithm of the compound concentration and Y is inhibition percent (%).

4. Experimental Results

TABLE 2

| Test compound | ACC1 $IC_{50}$ (nM) | ACC2 $IC_{50}$ (nM) |
| --- | --- | --- |
| Example 1 | 0.69 | 5.13 |
| Example 2 | 8.7 | — |
| Example 3 | 1 | 11.9 |
| Example 4 | 0.68 | 3.16 |
| Example 5 | 38.5 | — |
| Example 6 | 2.81 | 9.64 |
| Example 7 | 2.23 | 12.4 |
| Example 8 | 1.12 | 13.1 |
| Example 9 | 2.03 | 7.92 |
| Example 10 | 1.35 | 6.85 |
| Example 11 | 4.5 | — |
| Example 12 | 1.22 | 8.04 |
| Example 13 | 2.33 | 11.6 |
| Example 14 | 1.69 | 7.85 |
| Example 15 | 8.79 | — |
| Example 16 | 6.89 | — |
| Example 17 | 7.66 | — |
| Example 18 | >1000 | — |
| Example 19 | 23.3 | — |
| Example 20 | 0.91 | 8.03 |
| Example 21 | 0.70 | — |
| Example 22 | 0.63 | 5.13 |
| Example 23 | 11.5 | — |
| Example 24 | 3.06 | 5.12 |
| Example 25 | 1.57 | 7.57 |
| Example 26 | 0.87 | 10.3 |
| Example 27 | 11.8 | — |
| Example 28 | 1.48 | 7.8 |
| Example 29 | 2.13 | 14.1 |
| Example 30 | 7.97 | — |
| Example 31 | 136 | — |
| ND-630 | 0.5 | 3.56 |

"—" means no assay was performed.

The above experimental results show that the compounds of the present disclosure have a good inhibitory activity against both ACC1 and ACC2.

Experimental Example 2 Evaluation of Compound Distribution in Rat Liver

1. Experimental Material
1.1 Animals

Male SD rats, SPF grade, purchased from Shanghai Sippr-BK Experimental Animal Co., Ltd.; body weight 220-250 g, license number: SCXK (Shanghai) 2013-0016. An acclimation period of 2-3 days was given before the experiments. The rats were fasted for 8-12 h before administration, supplied with water 2 h after administration and foods 4 h after administration.

1.2 Reagents

Methanol and acetonitrile were purchased from Merck; anhydrous ethanol, PEG400 and physiological saline were purchased from Nanjing Kaiji Biotechnology Development Co., Ltd.; orphenadrine was purchased from Shanghai Ziqi Biotechnology Co., Ltd.

1.3 Instruments

API 4000 triple quadrupole liquid chromatograph/mass spectrometer, Analyst QS A01.01 chromatography workstation were purchased from AB SCIEX, USA; Milli-Q ultra-pure water was purchased from Millipore; CF 16R XII desktop high speed refrigerated centrifuge was purchased from Hitachi; Qilinbeier Vortex-5 oscillator was purchased from IKA, Germany; electric thermostatic water bath was purchased from Changzhou Guohua Electric Co., Ltd.; electric pipette was purchased from Thermo, USA; microanalytical balance was purchased from Shanghai METTLER Co., Ltd.

2. Experimental Methods
2.1 Preparation of Test Drugs 6 mg of the test compound (based on free base) was weighed and added to 20 mL of ethanol-PEG400-saline (10:30:60). The mixture was vortexed for 2 min, and sonicated for 3 min, and then used to prepare a solution of test sample solution with a concentration of 0.3 mg/mL for oral administration. 100 µL of the test sample solution was volumed to 10 ng/mL with methanol, and a control sample of the same concentration was prepared. The concentrations of the test sample and control sample were detected by HPLC, and the accuracy was calculated.

2.2 Sample Collection

SD rats were given a single oral administration of 3 mg/kg of test compound at a dose of 10 mL/kg. The rats were bled in femoral artery and ruptured in neck 0.25 h after administration. The liver and blood samples (anticoagulation with heparin sodium) were collected immediately, and placed on ice.

2.3 Liver Sample Processing and Analysis 0.4 g of liver tissue was weighed, chopped, and homogenized in 2 mL of 75% methanol-water. The homogenate was centrifuged (centrifugation conditions: 8000 rpm/min, 5 min, 4° C.). The supernatant was transferred and subjected to cryopreservation. The supernatant was thawed and centrifuged before injection, and the supernatant was collected and subjected to LC-MS/MS for analyzing the content of the compound in the supernatant sample.

2.4 Blood Sample Processing and Analysis

The collected whole blood sample was placed on ice and centrifuged within 30 min (centrifugation conditions: 8000 rpm/min, 5 min, 4° C.). 100 µL of the upper layer of plasma was transferred, and precipitated with 300 µL of methanol. The mixture was shaken and centrifuged, and diluted with mobile phase. The supernatant was collected and subjected to LC-MS/MS for analyzing the content of the compound in the supernatant sample.

3. Experimental Results

TABLE 3

| Compound | Concentration in Liver (ng/g) | Concentration in Plasma (ng/mL) | Liver/plasma distribution ratio |
|---|---|---|---|
| Example 1 | 4180 | 29.1 | 144 |
| Example 4 | 4828 | 72.8 | 67.1 |
| Example 7 | 1457 | 19.3 | 75.5 |
| Example 24 | 3167 | 48.5 | 65.3 |
| Example 25 | 3198 | 21.2 | 151 |
| ND-630 | 6066 | 145 | 41.8 |

The higher the concentration of the compound in the liver, the higher the potency for treating liver disease, the better the efficacy at the same dosage. The higher the liver/plasma ratio, the better the target organ selectivity of the test compound, the better the safety of the compound. From the above results, it can be seen that the compounds of the present disclosure have a high enrichment in the liver, and the selectivity and targeting to liver are good (liver/plasma ratio >50). Therefore, the compounds of the present disclosure are expected to be a more effective and safer drug for the treatment of metabolic liver diseases such as fatty liver and nonalcoholic fatty liver hepatitis (NASH).

Experimental Example 3 Inhibition of Human Hepatic Stellate Cells LX-2 Activation In Vitro 1. Experimental Materials
1.1 Compound Preparation The compounds of the present disclosure prepared in the above examples and the control compound were respectively formulated into 60 mM with DMSO for use.

1.2 Cell Line

Human hepatic stellate cell line LX-2 was established by Professor Xu Lieming at the Hepatology Center of Mount Sinai School of Medicine in the United States, and preserved in the Cell bank of Shanghai hepatology research institute.

1.3 Reagents

DMEM medium, FBS, trypsin, phosphate buffer (DPBS) and penicillin-streptomycin double antibiotics were purchased from GIBCO, USA; recombinant human TGF-β1 cytokine was purchased from PeproTech, Cat: 100-21; TransZOL Up Plus RNA extraction kit was purchased from TransGen Biotech, Cat: ER501-01; cDNA reverse transcription kit was purchased from TransGen Biotech, Cat: AH341-01; 5×SYBR Green qPCR kit was purchased from QuantiNova™, Cat: 154045739).

1.4 Consumables and Instruments:

CKX41 inverted microscope, Olympus, Japan; multifunction microplate reader, Molecular Devices, America; Thermo Nano Drop 2000 nucleic acid quantitative analyzer; ABI 9700 PCR instrument; ABI 7500 PCR fluorescence quantitative; Thermo high-speed centrifuge (MEGAFUGE8); automatic ice machine (Xueke, IMS-30)

2. Experimental Methods
2.1 Reagent Preparation

DMSO stock solution of the compounds of the examples of the present disclosure and the control compound were sequentially diluted with culture medium to 30 µM, 10 µM, and 3 µM. TGF-β1 was dissolved to 1 g/mL with 10 mM citric acid buffer in the kit (PeproTech) according to the instructions, ready for use.

2.2 LX-2 Cell Treatment

LX-2 cells were inoculated into a 6-well culture plate at a density of $2\times10^5$ cells/mL after cell passage. Each well contained 2 mL DMEM with 10% FBS. The cells were cultured at 37° C. in a 5% $CO_2$ incubator, which was recorded as Day 1. After 24 h (Day 2), the cell confluence reached 70-80%, the old culture medium was discarded, and the serum-free DMEM was used to treat the cells as low serum starvation. The old culture medium was discarded at Day 3, and the culture medium or the culture medium containing different concentrations of the drug was added for continuing culture. There were control group (serum-free DMEM culture medium), TGFβ1 group, TGFβ1+ compound group. The TGFβ1 working concentration was 10 ng/mL. 24 h after the drug treatment (Day 4), the cell medium was discarded and the cells were washed once with precooled 1×PBS and then subjected to total RNA extraction.

2.3 Total RNA Extraction 2.3.1 Sample pretreatment: 1 mL of TransZOL Up reagent was added to each well of the 6-well plate, and the well plate was placed horizontally for a while to let the lysis buffer evenly spread on the cell surface and lyse the cells. The cells were blown with a pipette to make the cells completely detached. The lysate was transferred to a 2 mL RNase free centrifuge tube and repeatedly blown and sucked until no significant pieces in the lysate.

2.3.2 Extraction step: according to the manufacturer's protocol of TransZOL Up Total RNA Extraction Kit.

2.4 Determination of Total RNA Concentration and Purity

2 μL of total RNA was added to NanoVue spectrophotometer to detect the absorbance at 260 nm wavelength and calculate the RNA concentration. The purity of the RNA sample was calculated based on the ratio of the absorbance values of 260 nm and 280 nm (A260/A280). If the ratio is in the range of 1.8-2.1, indicating that the RNA sample was not contaminated or degraded, which could be used in subsequent experiments.

2.5 cDNA Synthesis

The extracted RNA was diluted to a concentration of 0.1 μg-0.5 μg (Total RNA ≤1 μg) based on the same mass. The total RNA in the reverse transcription system of each sample in the experiment was about 500 ng.

The following operations were conducted according to the reverse transcription kit instruction (TransScript II All-in-One First-Strand cDNA Synthese kit, Lot: AH341-1). The synthesized cDNA was stored at −70° C. for use.

| Reagent | Amount |
|---|---|
| Template RNA (Total RNA) | about 0.5 μg |
| 5 × TransScript II All-in-One SuperMix for qPCR | 4 μl |
| gDNA Remover | 1 μL |
| Nuclease-free Water | to 20 μL |
| TotaL volume | 20 μL |

The above reaction system was mixed gently, placed in an ABI 9700 PCR machine. Program: 50° C.×15 min→85° C.×5 s→4° C.×10 min. The obtained cNDA was stored at −20° C. or used immediately.

2.6 Real-Time PCR Reaction

Real-Time PCR Primers:

| Gene | | Primer sequences | Gene Bank NO | Length (bp) |
|---|---|---|---|---|
| GAPDH | Forward | 5' TATAAATTGAGCC CGCAGCC 3' | NM 002046.5 | 141 |
| | Reverse | 5' ACCAAATCCGTTG ACTCCG 3' | | |
| Col1A1 | Forward | 5' TGAAGGGACACAG AGGTTTCAG 3' | NM 000088.3 | 193 |
| | Reverse | 5'GTAGCACCATCATT TCCACGA 3' | | |

PCR Reaction System:

| Reagent | Amount |
|---|---|
| SYBRGreen PCR Master Mix (2×) | 10 μL |
| QN ROX Reference Dye | 0.1 μL |
| PCR Forward Primer (10 μM) | 1.4 μL |
| PCR Reverse Primer (10 μM) | 1.4 μL |
| RNase-free water | 6.1 μL |
| cDNA template | 1 μL |
| Total | 20 μL |

After adding the reagents, the mixture was mixed gently, centrifuged, and the PCR tube was placed in a PCR machine. The PCR program was set as follow.

PCR Cycle Settings:

| Stage | Cycle | Cycle Point |
|---|---|---|
| Stage1 | Hold | 95° C., 2 min |
| Stage2 | Cycling (45 repeats) | Step 1 95° C., 5 secs |
| | | Step 2 60° C., 30 secs |
| Stage3 | Melt | 95° C., 15 secs; 60° C., 1 min; 95° C., 15 secs |

Two replicates were set for each sample, and the relative expression of the target gene was calculated by the program in the PCR machine.

3. Experimental Data Analysis

The threshold of the Real Time PCR result was automatically set by the Real Time PCR detector system. The relative expression of the Col1A1 gene was calculated as follows.

ΔCt (Col1A1 in drug treatment group)=Avg. Ct (Col1A1 in drug treatment group)−Avg. Ct (GAPDH in drug treatment group)

ΔCt (Col1A1 in TGF group)=Avg. Ct (Col1A1 in TGF group)−Avg. Ct (GAPDH in TGF group)

ΔCt (Col1A1 in Control group)=Avg. Ct (Col1A1 in Control group)−Avg. Ct (GAPDH in Control group)

ΔΔCt=Average value of ΔCt (Col1A1 in TGF group/ drug treatment group)−ΔCt (Col1A1 in Control group)

Formula for calculating the relative expression of Col1A1 gene: $RQ = 2^{-\Delta\Delta Ct}$ Relative quantification results were obtained by automatically analysis of ABI 7500 real-time quantitative PCR machine.

4. Experimental Results

TABLE 4

Calculation of the relative expression of the Col1A1 gene

| Compound | Inhibition rate (%) |
|---|---|
| Example 4 | 78.54 |
| Example 24a | 24.50 |
| Example 25 | 62.94 |
| Example 56 | 105.01 |
| ND-630 | 42.06 |

Collagen 1 was a key signaling factor in the formation of liver fibrosis, and its expression was represented by the expression of the Col1A1 gene. The experimental results showed that the compounds of the present disclosure have significant inhibitory activity on the expression of the Collagen 1 gene in TGF-β1-induced LX-2 cells. Compared with ND-630, some compounds of the present disclosure have stronger inhibitory activity on liver fibrosis formation, and can be used for ACC-mediated fibrotic diseases, proliferative diseases, and the like.

Experimental Example 4 Evaluation of the Drug Efficacy on NASH and Liver Fibrosis Induced by HFD-CCL4

High-fat diet (HFD) was used to induce liver steatosis in animals, and then carbon tetrachloride (CCL4) was used to induce liver inflammation, necrosis, and liver fibrosis. This model was similar to the human NASH disease process and pathological phenomenon. The purpose of this experiment was to evaluate the efficacy of the compound of the disclosure in a NASH model of C57BL/6 mice induced by HFD-CCL4, with ND-630 as a control compound. HFD-CCL4 inducement was performed for 10 weeks and drug intervention was performed for 4 weeks. The therapeutic effects of the drug on NASH and liver fibrosis were observed.
1. Experimental Material
1.1 Instruments
Dehydrator Leica HistoCore PEARL; paraffin embedder Leica HistoCore Arcadia C&H; paraffin slicer Leica RM2235; automatic staining machine Leica ST5020; scanner HAMAMATSU NANO Zoomer S210; SR staining analysis software Visiopharm VIS 6.6.0.2516.
1.2 Animals
C57BL/6 mice (male, 18-20 g) were purchased from Beijing Weitong Lihua Co., Ltd. All experimental protocols of the laboratory animal were approved by the KCI Institutional Animal Care and Use Committee (IACUC). The conditions for breeding mice were as follows: temperature 20-25° C., humidity 40%-70%, day and night alternate time 12 hours/12 hours. The bedding material was changed twice a week.
2. Experimental Methods
2.1 Compound Formulation
The test compounds in the examples of the present disclosure and ND-630 were diluted to 0.3 mg/mL, 1 mg/mL, 3 mg/mL with PEG200:0.2M Na2HPO4-NaH2PO4 buffer (35:65), which was prepared just before use.
2.2 Animal Modeling
HFD-CCL4 induced NASH model in C57BL/6 mice: the animals were first housed in the SPF barrier of the KCI Experimental Animal Center for 3-7 days, and then the animals were changed to HFD feeding in a cycle of 10 weeks. At the end of the $6^{th}$ week of HFD feeding, the HFD mice were randomly grouped according to the weight, 10 mice each group. CCL4 was orally administered (three times a week, at 9-10 am) for 4 weeks. Detailed modeling method was based on establishment of HFD-CCL4 induced NASH model in male C57BL/6 mice according to the method established by KCI. The modeling reagent was Olive Oil+CCL4 solution (prepared by KCI). The remaining 10 animals were given normal maintenance feed as normal control animals.

The animals were divided into a normal control group, a HFD-CCL4 model group (model group) and a compound group (test compound group of the present disclosure, ND-630 group).
2.3 Administration of the Compound
After 6 weeks of HFD feeding, the test compound of the present disclosure and ND-630 were administered intragastrically once a day for 4 weeks, and the administration was terminated at the $10^{th}$ week. The dose of the test compound group of the present disclosure was 10 mg/kg/d, and the dose of the ND-630 group was 30 mg/kg/d. That is, the dosage of the test compound group of the present disclosure was one third of the dosage of the ND-630 group.
2.4 Experimental Sample Collection
In the next day after the last administration, i.e., 48 h after the last administration of CCL4, the animals in each group were fasted for six hours, and the animals were euthanized according to KCI standard protocol. The animals were dissected according to the KCI animal dissection experimental operating procedures. After the animals were perfused with PBS throughout the body at low temperature, the livers (left liver lobe of each animal) were collected. The liver samples were quickly frozen with liquid nitrogen and stored at low temperature of −80° C. The remaining animal livers were fixed with formalin (the volume ratio of the liver to the fixation solution was 1:10), and pathological tests were performed.
2.5 Hematoxylin-Eosin Staining
The left liver lobe sample was fixed with 10% formalin and embedded in paraffin to prepare 5 μm sections for haematoxylin-eosin (H&E) staining. Hematoxylin-eosin staining can detect tissue inflammation, fat deposition, vacuolar degeneration and tissue fibrosis, giving semi-quantitative analysis for the lesion.
2.6 Sirius Red Staining
Liver tissue was cut into 5 m sections and dried for 2 h. After rehydration, the sections were stained with Sirius red (Beijing Head, article number: 26357) at room temperature for 30 min, and then dehydrated and sealed for image analysis. Sections were scanned with Aperio ScanScope CS2 (Leica) at 200× magnification, and the scanned images were opened in the Aperio ImageScope program to remove blood vessel signals. The remaining target images were algorithm analyzed by Color Deconvolution v9. The fibrotic parts stained red was identified by the software as a positive signal and used to calculate the percentage of fibrosis.
3. Statistical Analysis
The data were expressed as mean±standard error. The significance analysis used student t-test, one way ANOVA or two way ANOVA and post-hoc Dunnett's test.
4. Experimental Result
4.1 Hepatic Steatosis
The experimental animals were given a high-fat diet for 10 weeks. Compared with the normal control group, hepatic steatosis in the model group was significantly worse. The steatosis in compound group of Example 25 (10 mg/kg/d) was significantly less than the model group, and the effect was also significantly better than the ND-630 group (30 mg/kg/d). The experimental results are shown in Table 5.

TABLE 5

| Hepatic steatosis | |
| --- | --- |
| Group | Hepatic steatosis score Mean + standard deviation (Mean± SD) |
| Normal control group | 0.00 ± 0.00 |
| Model group | 0.37 ± 0.48 |
| Example 25 (10 mg/kg/d) | 0.03 ± 0.11 |
| ND-630 (30 mg/kg/d) | 0.13 ± 0.32 |

4.2 Hepatocyte Degeneration

Compared with the normal control group, the hepatocyte degeneration in the model group was significantly worse. After treatment of compounds, compared with the model group, the hepatocyte degeneration in the compound group of Example 25 (10 mg/kg/d) was significantly reduced. The experimental results are shown in Table 6.

TABLE 6

| Hepatocyte necrosis | |
| --- | --- |
| Group | Hepatocyte necrosis score Mean + standard deviation (Mean ± SD) |
| Normal control group | 0.00 ± 0.00 |
| Model group | 0.74 ± 0.49 |
| Example 25 (10 mg/kg/d) | 0.56 ± 0.48 |
| ND-630 (30 mg/kg/d) | 1.00 ± 0.61 |

It can be seen that the compounds of the present disclosure has a certain therapeutic effect on the HFD-CCL4 induced NASH mouse model; in terms of histopathology, compared with the model group, the compounds of the present disclosure can effectively reduce hepatic steatosis and hepatocyte degeneration.

Although the present disclosure has been described in detail above, those skilled in the art understand that various modifications and changes can be made to the present disclosure without departing from the spirit and scope of the present disclosure. The scope of rights of the present disclosure is not limited to the detailed description made above, but should be attributed to the claims.

What is claimed is:

1. A compound or pharmaceutically acceptable salt, solvate, crystal or prodrug thereof, wherein the compound is selected from:

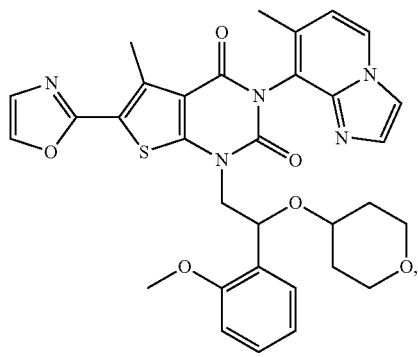

-continued

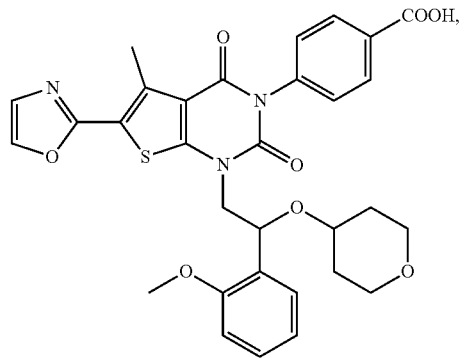

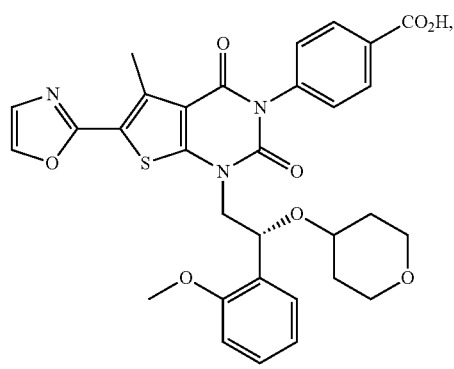

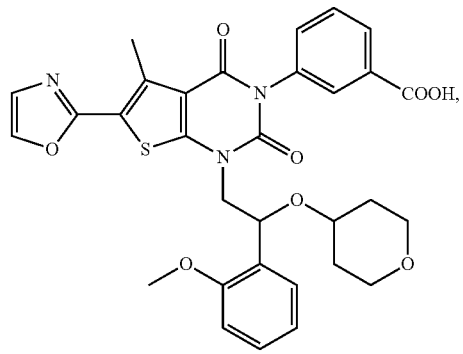

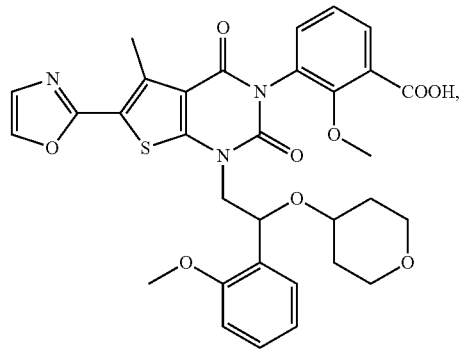

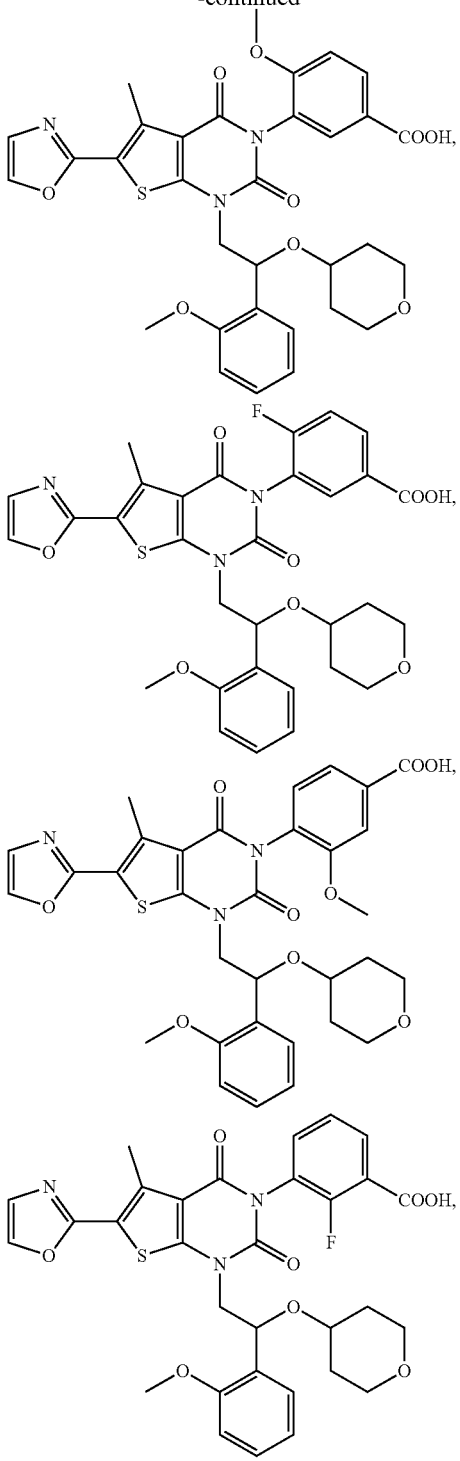

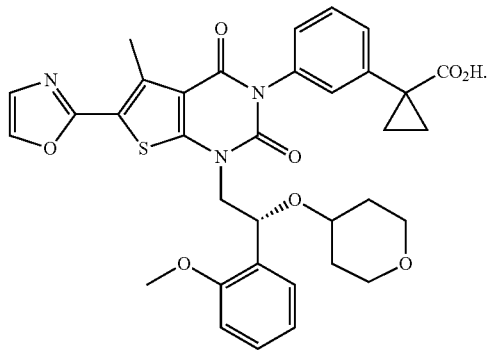 [SMILES: COc1ccccc1[C@H](Cn1c(=O)n(-c2cccc(C3(C(=O)O)CC3)c2)c(=O)c2c(C)c(-c3ncco3)sc21)OC1CCOCC1]

2. A pharmaceutical composition comprising the compound or pharmaceutically acceptable salt, solvate, crystal or prodrug thereof according to claim 1 and a pharmaceutically acceptable carrier.

3. A method of treating diseases associated with ACC expression, comprising administering the compound or pharmaceutically acceptable salt, solvate, crystal or prodrug thereof according to claim 1 to a subject in need thereof.

4. The method according to claim 3, wherein the disease is selected from fibrotic disease, metabolic disease, tumor and proliferative disease.

5. The method according to claim 3, wherein the disease is selected from liver fibrosis, obesity, diabetes, nonalcoholic fatty liver disease, nonalcoholic steatohepatitis, liver cancer, kidney cancer, lung cancer, breast cancer, melanoma, papillary thyroid tumor, cholangiocarcinoma, colon cancer, ovarian cancer, malignant lymphoma, cancer and sarcoma of bladder, prostate and pancreas, and primary or recurrent solid tumor of skin, colon, thyroid or ovary.

6. A method of treating diseases associated with ACC expression, comprising administering the pharmaceutical composition according to claim 2 to a subject in need thereof.

7. The method according to claim 6, wherein the disease is selected from fibrotic disease, metabolic disease, tumor and proliferative disease.

8. The method according to claim 6, wherein the disease is selected from liver fibrosis, obesity, diabetes, nonalcoholic fatty liver disease, nonalcoholic steatohepatitis, liver cancer, kidney cancer, lung cancer, breast cancer, melanoma, papillary thyroid tumor, cholangiocarcinoma, colon cancer, ovarian cancer, malignant lymphoma, cancer and sarcoma of bladder, prostate and pancreas, and primary or recurrent solid tumor of skin, colon, thyroid or ovary.

* * * * *